(12) United States Patent
Kath et al.

(10) Patent No.: US 6,284,764 B1
(45) Date of Patent: Sep. 4, 2001

(54) SUBSTITUTED BICYCLIC DERIVATIVES USEFUL AS ANTICANCER AGENTS

(75) Inventors: John Charles Kath; Norma Jacqueline Tom; Zhengyu Liu, all of Waterford; Eric David Cox, Mystic; Joel Morris, East Lyme; Samit Kumar Bhattacharya, Groton, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/488,350

(22) Filed: Jan. 20, 2000

Related U.S. Application Data

(62) Division of application No. 09/488,350, filed on Jan. 20, 2000.
(60) Provisional application No. 60/117,346, filed on Jan. 27, 1999.

(51) Int. Cl.[7] ............ A61K 31/517; C07D 239/72
(52) U.S. Cl. ............ 514/259; 544/283; 544/293
(58) Field of Search ............ 514/259; 544/283, 544/293

(56) References Cited

U.S. PATENT DOCUMENTS

| | | | |
|---|---|---|---|
| 5,256,781 | 10/1993 | Primeau et al. | 544/293 |
| 5,283,242 | 2/1994 | Elingboe | 514/186 |
| 5,360,809 | 11/1994 | Axelsson | 514/338 |
| 5,736,534 | 4/1998 | Arnold | 514/63 |
| 5,747,498 | 5/1998 | Schnur et al. | 514/259 |
| 5,866,572 | 2/1999 | Barker et al. | 514/234.5 |

FOREIGN PATENT DOCUMENTS

| | | |
|---|---|---|
| 2225366 | 6/1998 | (CA) . |
| 0520722 | 12/1992 | (EP) . |
| 0566226 | 10/1993 | (EP) . |
| 0602851 | 6/1994 | (EP) . |
| 0635498 | 1/1995 | (EP) . |
| 0635507 | 1/1995 | (EP) . |
| 0882717 | 12/1998 | (EP) . |
| 9220642 | 11/1992 | (WO) . |
| 9307146 | * 4/1993 | (WO) . |
| 9730034 | * 4/1993 | (WO) . |
| WO9519774 | 7/1995 | (WO) . |
| 9609294 | 3/1996 | (WO) . |
| 9616960 | 6/1996 | (WO) . |
| WO9628430 | 9/1996 | (WO) . |
| WO9640142 | 12/1996 | (WO) . |
| 9721701 | 6/1997 | (WO) . |
| WO9722596 | 6/1997 | (WO) . |
| 9730034 | 8/1997 | (WO) . |
| WO9730044 | 8/1997 | (WO) . |
| 9802438 | 1/1998 | (WO) . |
| 9802434 | * 1/1998 | (WO) . |
| 9802437 | 1/1998 | (WO) . |
| 9924440 | * 5/1999 | (WO) . |

OTHER PUBLICATIONS

Spada et al., "Small Molecule Inhibitors of Tyrosine Kinase Activity," Expert Opinion on Therapeutic Patents, GB, Ashley Publications, vol. 5, No. 8, Jan. 1, 1995.

Craciunescu et al., "Study of the "in vivo" Dueal (Antitumor and Trypanocidal) Pharmacological Effects Displayed By Dimeric and Neutral New Complexes of Iridium (II) and Rhodium (II) With Classical Antimalarial Drugs," An. R. Acad. Farm., 1991, 57(1), 15–35.

Nomoto et al., "Studies on Cardiotonic Agents. VI. Potent Cardiotonic Agent KF15232 With Myofribrillar Calcium Sensitizing Effect," Chem. Pharm. Bull., 1991, 39(4), 900–910.

Nomoto, Yuji et al. "Studies on cardiotonic agts."VII Jap.Chem.Pharm.Bull. 411, 39/4, 900–10, Apr. 1991.*

D.G. Craciunescu et al."Study of the in vivo dual–antitumor/trypanocidal. . . "An.R.Aca.Fa.57/1/15, Apr. 1991.*

* cited by examiner

Primary Examiner—Richard L. Raymond
Assistant Examiner—Sudhaker B. Patel
(74) Attorney, Agent, or Firm—Peter C. Richardson; Paul H. Ginsburg; Adrian G. Looney

(57) ABSTRACT

The invention relates to compounds of the formula 1

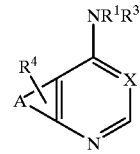

and to pharmaceutically acceptable salts and solvates thereof, wherein A, X, $R^1$, $R^3$ and $R^4$ are as defined herein. The invention also relates to methods of treating abnormal cell growth in mammals with administering the compounds of formula 1 and to pharmaceutical compositions for treating such disorders which contain the compounds of formula 1. The invention also relates to methods of preparing the compounds of formula 1.

21 Claims, No Drawings

SUBSTITUTED BICYCLIC DERIVATIVES USEFUL AS ANTICANCER AGENTS

This is a division of application Ser. No. 09/488,350 filed Jan. 20, 2000, which claims the benefit of U.S. Provisional Application No. 60/117,346, filed Jan. 27, 1999, both which are incorporated herein by reference.

BACKGROUND OF THE INVENTION

This invention relates to novel bicyclic derivatives that are useful in the treatment of abnormal cell growth, such as cancer, in mammals. This invention also relates to a method of using such compounds in the treatment of abnormal cell growth in mammals, especially humans, and to pharmaceutical compositions containing such compounds.

It is known that a cell may become cancerous by virtue of the transformation of a portion of its DNA into an oncogene (ie., a gene which, on activation, leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. Other receptor tyrosine kinases include c-erbB-2, c-met, tie-2, PDGFr, FGFr, and VEGFR. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR), which possesses tyrosine kinase activity, is mutated and/or overexpressed in many human cancers such as brain, lung, squamous cell, bladder, gastric, breast, head and neck, oesophageal, gynecological and thyroid tumors.

Accordingly, it has been recognized that inhibitors of receptor tyrosine kinases are useful as selective inhibitors of the growth of mammalian cancer cells. For example, erbstatin, a tyrosine kinase inhibitor, selectively attenuates the growth in athymic nude mice of a transplanted human mammary carcinoma which expresses epidermal growth factor receptor tyrosine kinase (EGFR) but is without effect on the growth of another carcinoma which does not express the EGF receptor. Thus, the compounds of the present invention, which are selective inhibitors of certain receptor tyrosine kinases, are useful in the treatment of abnormal cell growth, in particular cancer, in mammals. In addition to receptor tyrosine kinases, the compounds of the present invention can also display inhibitory activity against a variety of other non-receptor tyrosine kinases (eg: lck, src, abl) or serine/threonine kinases (e.g.: cyclin dependent kinases).

Various other compounds, such as styrene derivatives, have also been shown to possess tyrosine kinase inhibitory properties. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98102434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose.

SUMMARY OF THE INVENTION

The present invention relates to compounds of the formula 1

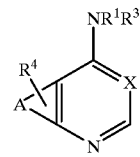

and to pharmaceutically acceptable salts and solvates thereof, wherein:

X is N or CH;

A represents a fused 5, 6 or 7-membered ring optionally containing 1 to 4 heteroatoms which may be the same or different and which are selected from —N($R^1$)—, O, and S(O)$_j$, wherein j is an integer from 0 to 2, the fused ring containing a total of 1, 2 or 3 double bonds inclusive of the bond in the pyridine or pyrimidine ring to which it is fused wherein the $R^1$ group attached to the nitrogen is absent if a double bond includes the foregoing optional nitrogen moiety —N($R^1$)—, with the proviso that the fused ring does not form part of a purine and that the fused ring does not contain two adjacent O or S(O)$_j$ atoms, and wherein the carbon atoms of the A moiety are optionally substituted with 1 to 3 $R^5$ groups;

each $R^1$ and $R^2$ is independently H or $C_1$–$C_6$ alkyl;

$R^3$ is —$(CR^1R^2)_m$—$R^8$ wherein m is 0 or 1;

or $R^1$ and $R^3$ are taken together to form a group of the formula

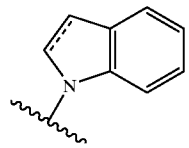

wherein said group is optionally substituted with 1 to 3 $R^5$ groups;

$R^4$ is —$(CR^1R^2)_m$—C≡C—$(CR^1R^2)_tR^9$, —$(CR^1R^2)_m$—C=C—$(CR^1R^2)_t$—$R^9$, —C=NOR$^{12}$, or —$X^1$—$R^{12}$ wherein m is an integer from 0 to 3, t is an integer from 0 to 5, and $X^1$ is a divalent group derived from azetidine, oxetane or a $C_3$–$C_4$ carbocyclic group;

or $R^4$ is —$(CR^1R^2)_m$—C≡C—$(CR^1R^2)_kR^{13}$ or —$(CR^1R^2)_m$—C=C—$(CR^1R^2)_kR^{13}$ wherein k is an integer from 1 to 3 and m is an integer from 0 to 3;

or $R^4$ is —$(CR^1R^2)_tR^9$, wherein t is an integer from 0 to 5 and the attachment point to $R^9$ is through a carbon atom of the $R^9$ group;

each $R^5$ is independently selected from halo, hydroxy, —$NR^1R^2$, $C_1$–$C_6$ alkyl, trifluoromethyl, $C_1$–$C_6$ alkoxy, trifluoromethoxy, —$C(O)R^6$, —$CO_2R^6$, —$NR^6C(O)R^1$, —$C(O)NR^6R^7$, —$SO_2NR^6R^7$, —$NR^8C(O)NR^7R^1$, and —$NR^6C(O)OR^7$;

each $R^6$ and $R^7$ is independently selected from H, $C_1$–$C_6$ alkyl, —$(CR^1R^2)_t(C_6$–$C_{10}$ aryl), and —$(CR^1R^2)_t$(4–10 membered heterocyclic), wherein t is an integer from 0 to 5, 1 or 2 ring carbon atoms of the heterocyclic group are optionally substituted with an oxo (=O) moiety, and the alkyl, aryl and heterocyclic moieties of the foregoing $R^6$ and $R^7$ groups are optionally substituted with 1 to 3 substituents independently selected from halo, cyano, nitro, —$NR^1R^2$, trifluoromethyl, trifluoromethoxy, $C_1$–$C_6$ alkyl, $C_2$–$C_6$ alkenyl, $C_2$–$C_6$ alkynyl, hydroxy, and $C_1$–$C_6$ alkoxy;

$R^8$ is independently selected from —$(CR^1R^2)_t(C_6$–$C_{10}$ aryl) and —$(CR^1R^2)_t$(4–10 membered heterocyclic), wherein t is an integer from 0 to 5, 1 or 2 ring carbon atoms of the heterocyclic group are optionally substituted with an oxo (=O) moiety, and each of the foregoing $R^6$ groups is optionally substituted with 1 to 5 $R^{10}$ groups;

$R^9$ is a non-aromatic mono-cyclic ring, a fused or bridged bicyclic ring, or a spirocyclic ring, wherein said ring contains from 3 to 12 carbon atoms in which from 0 to 3 carbon atoms are optionally replaced with a hetero moiety independently selected from N, O, S(O)j wherein j is an integer from 0 to 2, and —$NR^{12}$—, provided that two O atoms, two S(O)j moieties, an O atom and a S(O)j moiety, an N atom and an S atom, or an N atom and an O atom are not attached directly to each other within said ring, and wherein the carbon atoms of said ring are optionally substituted with 1 to 2 $R^{11}$ groups;

each $R^{10}$ is independently selected from halo, cyano, nitro, trifluoromethoxy, trifluoromethyl, azido, hydroxy, $C_1$–$C_6$ alkoxy, $C_1$–$C_{10}$ alkyl, $C_2$–$C_6$ alkenyl, $C_2$–$C_6$ alkynyl, —$C(O)R^6$, —$C(O)OR^6$, —$OC(O)R^6$, —$NR^6C(O)R^7$, —$NR^6C(O)NR^1R^7$, —$NR^6C(O)OR^7$, —$C(O)NR^6R^7$, —$NR^6R^7$, —$NR^6OR^7$, —$SO_2NR^6R^7$, —$S(O)_j(C_1$–$C_6$ alkyl) wherein j is an integer from 0 to 2, —$(CR^1R^2)_t(C_6$–$C_{10}$ aryl), —$(CR^1R^2)_t$(4–10 membered heterocyclic), —$(CR^1R^2)_qC(O)(CR^1R^2)_t(C_6$–$C_{10}$ aryl), —$(CR^1R^2)_qC(O)(CR^1R^2)_t$(4–10 membered heterocyclic), —$(CR^1R^2)_tO(CR^1R^2)_q(C_6$–$C_{10}$ aryl), —$(CR^1R^2)_tO(CR^1R^2)_q$(4–10 membered heterocyclic), —$(CR^1R^2)_qS(O)_j(CR^1R^2)_t(C_6$–$C_{10}$ aryl), and —$(CR^1R^2)_qS(O)_j(CR^1R^2)_t$(4–10 membered heterocyclic), wherein j is 0, 1 or 2, q and t are each independently an integer from 0 to 5, 1 or 2 ring carbon atoms of the heterocyclic moieties of the foregoing $R^{10}$ groups are optionally substituted with an oxo (=O) moiety, and the alkyl, alkenyl, alkynyl, aryl and heterocyclic moieties of the foregoing $R^{10}$ groups are optionally substituted with 1 to 3 substituents independently selected from halo, cyano, nitro, trifluoromethyl, trifluoromethoxy, azido, —$OR^6$, —$C(O)R^6$, —$C(O)OR^6$, —$OC(O)R^6$, —$NR^6C(O)R^7$, —$C(O)NR^6R^7$, —$NR^6R^7$, —$NR^6OR^7$, $C_1$–$C_6$ alkyl, $C_2$–$C_6$ alkenyl, $C_2$–$C_6$ alkynyl, —$(CR^1R^2)_t$ $(C_6$–$C_{10}$ aryl), and —$(CR^1R^2)_t$(4–10 membered heterocyclic), wherein t is an integer from 0 to 5;

each $R^1$ is independently selected from —$R^{12}$, —$OR^1$, —$NR^1R^2$, —$NR^6C(O)R^7$, —$NR^6C(O)NR^7R^1$, —$NR^6C(O)OR^7$, and —$NR^6SO_2NR^7R^1$, or $R^{11}$ replaces two hydrogen atoms on a carbon to form an oxo (C=O) group;

$R^{12}$ is $R^6$, —$C(O)R^6$ or —$SO_2R^6$, —$C(O)NR^6R^7$, —$SO_2NR^6R^7$, or —$CO_2R^6$;

$R^{13}$ is —$NR^1R^{12}$ or —$OR^{12}$;

and wherein any of the above-mentioned substituents comprising a $CH_3$ (methyl), $CH_2$ (methylene), or CH (methine) group which is not attached to a halogeno, SO or $SO_2$ group or to a N, O or S atom optionally bears on said group a substituent selected from hydroxy, halo, $C_1$–$C_4$ alkyl, $C_1$–$C_4$ alkoxy and —$NR^1R^2$.

In a specific embodiment of the present invention, the A moiety of the compounds of formula 1 is selected from

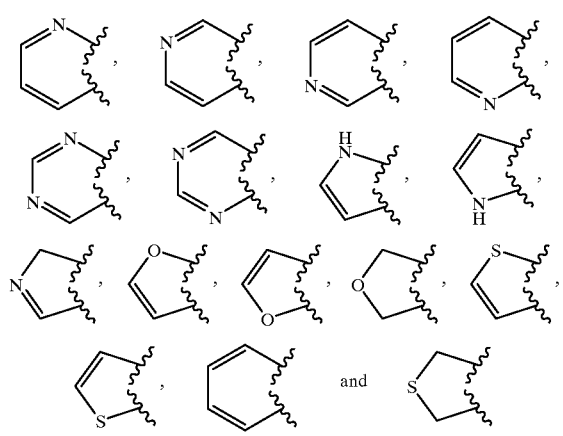

wherein the above A moieties bear an $R^4$ group as a substituent and optionally bear 1 to 3 $R^5$ groups as substituents.

Other specific embodiments of the compounds of formula 1 include those wherein A is selected from

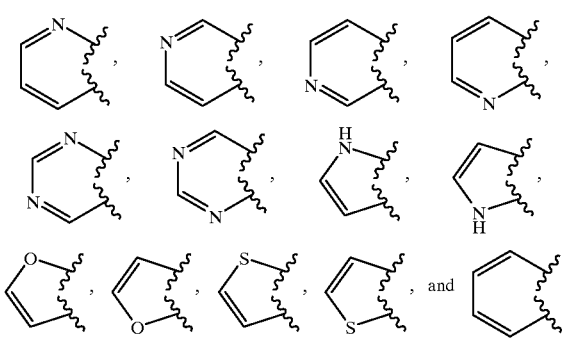

wherein the above A moieties bear an $R^4$ group as a substituent and optionally bear 1 to 3 $R^5$ groups as substituents.

Other specific embodiments of the compounds of formula 1 include those wherein A is selected from

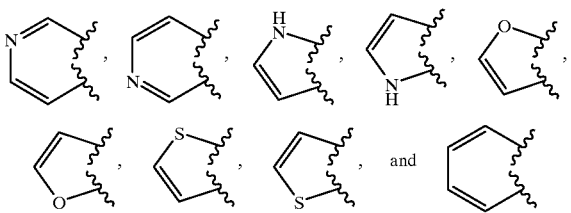

wherein the above A moieties bear an $R^4$ group as a substituent and optionally bear 1 to 3 $R^5$ groups as substituents.

Other specific embodiments of the compounds of formula 1 include those wherein A is selected from

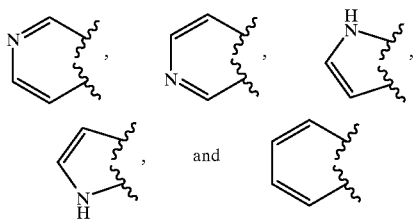

wherein the above A moieties bear an $R^4$ group as a substituent and optionally bear 1 to 3 $R^5$ groups as substituents.

Other specific embodiments of the compounds of formula 1 include those wherein A is

wherein the above A moieties bear an $R^4$ group as a substituent and optionally bear 1 to 3 $R^5$ groups as substituents.

Other specific embodiments of the compounds of formula 1 include those wherein $R^4$ is —$(CR^1R^2)_m$—C≡C—$(CR^1R^2)_t R^9$ wherein m is an integer from 0–3 and t is an integer from 0–5.

Other specific embodiments of the compounds of formula 1 include those wherein $R^4$ is —$(CR^1R^2)_m$—C≡C—$(CR^1R^2)_t$—$R^9$ and m is an integer from 0 to 3 and t is an integer from 0–5.

Other specific embodiments of the compounds of formula I include those wherein $R^4$ —$(CR^1R^2)_m$C≡C—$(CR^1R^2)_k R^{13}$ or —$(CR^1R^2)_m$—C≡C—$(CR^1R^2)_k R^{13}$ wherein m is an integer from 0–3 and k is an integer from 1 to 3

Other specific embodiments of the compounds of formula 1 include those wherein $R^4$ is is C=$NOR^{12}$, or —$X^1$—$R^{12}$ wherein $X^1$ is a divalent group derived from azetidine, oxetane or a $C_3$–$C_4$ carbocyclic group; or $R^4$ is —$(CR^1R^2)_t R^9$, wherein the attachment point to $R^9$ is through a carbon atom of $R^9$.

Other specific embodiments of the compounds of formula 1 include those wherein $R^8$ is selected from —$(CR^1R^2)_t$ (phenyl), —$(C^{R1}R^2)_t$(pyridyl), —$(CR^1R^2)_t$(pyrimidinyl), —$(CR^1R^2)_t$(indolyl), —$(CR^1R^2)_t$(indazolyl) and —$(CR^1R^2)_t$(benzimidazolyl), wherein t is an integer from 0 to 5, and each of the foregoing $R^6$ groups is optionally substituted with 1 to 5 $R^{10}$ groups.

Other specific embodiments of the compounds of formula 1 include those wherein $R^9$ is a 4 to 10 membered heterocyclic group having 1 to 3 hetero moieties as indicated in formula 1 above and wherein said $R^9$ is optionally substituted with 1 to 2 $R^{11}$ groups.

Preferred compounds include those selected from the group consisting of:

Acetic acid 3-[4-(1-benzenesulfonyl-1H-indol-5-ylamino)-quinazolin-6-yl]-allyl ester;

(1-Benzenesulfonyl-1H-indol-5-yl)-{6-[3-(4-methyl-piperazin-1-yl)-prop-1-ynyl]-quinazolin-4-yl}amine;

(1-Benzenesulfonyl-1H-indol-5-yl)-[6-(3-pyrrolidin-1-yl-prop-1-ynyl)quinazolin4-yl]-amine;

4-[4-(1-Benzenesulfonyl-1H-indol-5-ylamino)-quinazolin-6-ylethynyl]-piperidin-4-ol;

(1-Benzenesulfonyl-1H-indol-5-yl)-(6-piperidin-4-ylethynyl-quinazolin-4-yl)-amine;

[6-(4-Amino-tetrahydro-pyran-4-ylethynyl)-quinazolin4-yl]-(1-benzenesulfonyl- 1H-indol-5-yl)-amine;

1-Methyl-4-{4-[3-methyl-4-(pyridin-2-ylmethoxy)-phenylamino]- quinazolin6-ylethynyl}-piperidin-4-ol;

1-[4-(1-Benzenesulfonyl-1H-indol-5-ylamino)-quinazolin-6-yl]-4-methyl-pent-1-yn-3-ol:

4-{4-[4-(1-Phenyl-ethoxy)-phenylamino]-quinazolin-6-ylethynyl}-tetrahydro-pyran-4-ol;

1-[4-(1-Benzenesulfonyl-1H-indol-5-ylamino)-quinazolin-6-yl]-4,4-dimethyl-pent-1-yn-3-ol;

4,4-Dimethyl-1-{4-[4-(1-phenyl-ethoxy)-phenylamino]-quinazolin-6-yl)-pent-1-yn-3-ol;

3-{4-[1-(Propane-2-sulfonyl)-1H-indol-5-ylamino]-quinazolin-6-ylethynyl}-piperidin-3-ol;

1-Methyl-3-(4-(4-phenoxy-phenylamino)-quinazolin-6-ylethynyl]- piperidin-3-ol;

3-[4-(3-Methyl4-phenoxy-phenylamino)-quinazolin-6-ylethynyl]- piperidin-3-ol;

3-[4-(3-Chloro-4-phenoxy-phenylamino)-quinazolin-6-yl]-1-pyrrolidin-2-yl-prop-2-yn-1-ol;

5-[4(1-Benzyl-1H-indazol-5-ylamino)-quinazolin-6-ylethynyl]-4,4-dimethyl-oxazolidin-2-one;

4-Amino-1-[4-(3-chloro-4-phenoxy-phenylamino)-quinazolin-6-yl]-pent-1-yn-3-ol;

4-Amino-1-[4-(3-chloro-4-phenoxy-phenylamino)-quinazolin-6-yl]-4-methyl-pent-1-yn-3ol;

3-{2-[4-(3-Methyl-4-phenoxy-phenylamino)-quinazolin-6-yl]-ethyl}piperidin-3-ol;

and the pharmaceutically acceptable salts and solvates of the foregoing compounds.

In accordance with the present invention, the most preferred compounds include those selected from the group consisting of (+)-(3-Methyl-4-phenoxy-phenyl)-(6-piperidin-3(R)-ylethynyl-quinazolin-4-yl)-amine;

(−)-(3-Methyl-4-phenoxy-phenyl)-(6-piperidin-3(S)-ylethynyl-quinazolin-4-yl)-amine;

3-(S)-[4-(3-Methyl-4-phenoxy-phenylamino)-quinazolin-6-ylethynyl]-piperidine-1-carboxylic acid methylamide;

3-(S)-[4-(3-Methoxy-4-phenoxy-phenylamino)-quinazolin -ylethynyl]-piperidine-1-carboxylic acid methylamide;

(3-Methyl-4-phenoxy-phenyl)-(6-pyrrolidin-3-ylethynyl-quinazolin-4-yl)-amine;

3-[4-(5-Methyl-6-phenoxy-pyridin-3-ylamino)-quinazolin-6-ylethynyl]-piperidin-3-ol;

(−)-3-[4-(3-Methyl-4-phenoxy-phenylamino)-quinazolin-6-ylethynyl]-piperidin-3-ol;

(+)-3-[4-(3-Methyl-4-phenoxy-phenylamino)-quinazolin-4-ylethynyl]-piperidin-3-ol;

4-[4-(3-Methyl-4-phenoxy-phenylamino)-quinazolin-6-ylethynyl]-tetrahydro-pyran4ol;

{6-[1-(2-Methoxy-ethyl)-piperidin-3-ylethynyl]-quinazolin-4-yl}-(3-methyl-4-phenoxy-phenyl)-amine;

[4-(2-Fluoro-phenoxy)-3-methyl-phenyl]-(6-piperidin-3-ylethynyl-quinazolin-4-yl)-amine;

[4-(3-Fluoro-phenoxy)-3-methyl-phenyl]-(6-piperidin-3-ylethynyl-quinazolin-4-yl)-amine.

(6-Azetidine-3-ylethynyl-quinazolin-4-yl)-(3-methyl-4-phenoxy-phenyl)-amine;

3-{4-[4-(2-Fluoro-phenoxy)-3-methyl-phenylamino]-quinazolin-6-ylethynyl}-piperidin-3-ol;

3-{4-[4-(3-Fluoro-phenoxy)-3-methyl-phenylamino]-quinazolin-6-ylethynyl}-piperidin-3-ol;

4-[4-(3-Methyl-4-phenoxy-phenylamino)-quinazolin-6-ylethynyl]-piperidin4-ol;

(3-Chloro4-phenoxy-phenyl)-(6-piperidin-3-ylethynyl-quinazolin-4-yl)-amine;

3-[4-(3-Methyl-4-phenoxy-phenylamino)-quinazolin-6-ylethynyl]-8-aza-bicyclo[3.2.1]octan-3-ol;

(3-Chloro-4-phenoxy-phenyl)-(6-piperidin-4-ylethynyl-quinazolin-4-yl)-amine;

3-[4-(3-Methyl-4-phenoxy-phenylamino)-quinazolin-6-ylethynyl]-pyrrolidin-3-ol;

3-[4-(3-Methyl-4-phenoxy-phenylamino)-quinazolin-7-ylethynyl]-piperidin-3-ol;

and the pharmaceutically acceptable salts and solvates of the foregoing compounds.

Other preferred compounds include those selected from the group consisting of:

N-{3-[4-(3-Chloro-4-phenoxy-phenylamino)-quinazolin 6-yl]-prop-2-ynyl}-acetamide;

N-{3-[4-(3-Methyl-4-phenoxy-phenylamino)-quinazolin-6-yl]-prop-2-ynyl}-acetamide;

(3-{3-[4-(3-Methyl-4-phenoxy-phenylamino)-quinazolin-6-yl]-prop-2-ynyl}-3-aza-bicyclo[3.1.0]hex-6-yl)-methanol;

4-{3-[4-(3-Methoxy-4-phenoxy-phenylamino)-quinazolin-6-yl]-prop-2-ynyl}-piperazine-carboxylic acid methylamide;

{6-[3-(1,1-Dioxo-1-thiomorpholin-4-yl)-prop-1-ynyl]-quinazolin-4-yl}-(3-methyl-4-phenoxy-phenyl)-amine;

1-{3-[4-(3-Methyl-4-phenoxy-phenylamino)-quinazolin-6-yl)-prop-2-ynyl}-piperidin-4-ol;

N-{1-Methyl-3-[4-(3-methyl-4-phenoxy-phenylamino)-quinazolin-6-yl]-prop-2-ynyl}-acetamide;

N-{3-[4-(3-Chloro4-phenoxy-phenylamino)-quinazolin-yl]-1-methyl-prop-2-ynyl}-acetamide;

N-{1,1-Dimethyl-3-[4-methyl-4-phenoxy-phenylamino)-quinazolin-6-yl]-prop-2-ynyl}-acetamide;

4-[4-(1-Benzenesulfonyl-1H-indol-5-ylamino)-quinazolin-ylethynyl]-1-methyl-piperidin-4-ol;

3-[4-(1-Benzenesulfonyl-1H-indol-5-ylamino)-quinazolin-6-ylethynyl]-piperidin-3-ol;

3-[4-(3-Bromo-4-phenoxy-phenylamino)quinazolin-6-ylethynyl]-piperidin-3-ol;

3-[4-(4-Benzenesulfonyl-3-methyl-phenylamino)quinazolin-6-ylethynyl]-piperidin-3-ol;

3-[4-(4-Cyclohexyloxy-3-methyl-phenylamino)-quinazolin-6-ylethynyl]-piperidin-3-ol;

2-Methyl-4-(4-(3-methyl-4-phenoxy-phenylamino)-quinazolin-6-yl]-but-3-yn-2-ol;

2-Amino-4(3-methyl-4-phenoxy-phenylamino)-quinazolin-6-yl]-but-3-yn-1-ol;

3-[4-(3-Methyl-4-phenylsulfanyl-phenylamino)-quinazolin-6-ylethynyl]-piperidin-3-ol:

and the pharmaceutically acceptable salts and solvates of the foregoing compounds.

Other preferred compounds of the present invention include those selected from the group consisting of:

3-[4-(3-Chloro-4-fluoro-phenylamino)-quinazolin-6-ylethynyl]-piperidin-3-ol:

3-[4-(3-Ethynyl-phenylamino)-quinazolin-6-ylethynyl]-piperidin-3-ol;

(3-Methyl-4-phenoxy-phenyl)-[6-(1-methyl-piperidin-3-ylethynyl)-quinazolin-4-yl]-amine;

(3-Methyl-4-phenoxy-phenyl)-[6-(2-piperidin-3-yl-ethyl)-quinazolin-4-yl]-amine;

3-{2-[4-(3-Methyl-4-phenoxy-phenylamino)-quinazolin-6-yl]-ethyl}-piperidin-3-ol;

3-[4-(4-Phenoxy-phenylamino)-quinazolin-6-ylethynyl]-piperidin-3-ol;

3-Oxo-5-(4-pyrrolidin-1-yl-butyl)-1,2,3,5-tetrahydro-benzo-[4,5]imidazo-[1,2-a]pyridine-4-carboxylic acid benzylamide;

and the pharmaceutically acceptable salts and solvates of the foregoing compounds.

This invention also relates to a method for the treatment of abnormal cell growth in a mammal, including a human, comprising administering to said mammal an amount of a compound of the formula 1, as defined above, or a pharmaceutically acceptable salt or solvate thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostate hypertrophy or restinosis.

This invention also relates to a method for the treatment of abnormal cell growth in a mammal which comprises administering to said mammal an amount of a compound of formula 1, or a pharmaceutically acceptable salt or solvate thereof, that is effective in treating abnormal cell growth in combination with an ant-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

This invention also relates to a pharmaceutical composition for the treatment of abnormal cell growth in a mammal, including a human, comprising an amount of a compound of the formula 1, as defined above, or a pharmaceutically acceptable salt or solvate thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

The invention also relates to a pharmaceutical composition for the treatment of abnormal cell growth in a mammal, including a human, which comprises an amount of a compound of formula 1, as defined above, or a pharmaceutically acceptable salt or solvate thereof, that is effective in treating abnormal cell growth in combination with a pharmaceutically acceptable carrier and an ant-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and ant-androgens.

The invention also relates to a method of preparing a compound of the formula 1

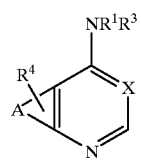

and pharmaceutically acceptable salts and solvates thereof, wherein A, X, $R^1$, $R^4$ and $R^3$ are as defined above, which comprises either (a) reacting a compound of the formula 11 or 2 with a compound of the formula 3

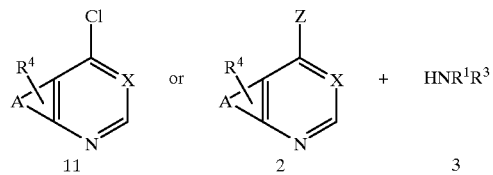

wherein Z is a leaving group and A, X, $R^1$, $R^4$ and $R^3$ are as defined above, or (b) reacting a compound of the formula 7 with a compound of the formula 3

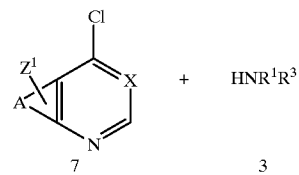

wherein X, $R^1$, A, $R^1$ and $R^3$ are as defined above and $Z^1$ is an activating group, to provide an intermediate of the formula 5

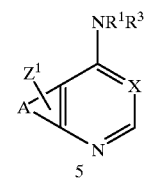

wherein $Z^1$, X, $R^1$, A, and $R^3$ are as defined above and $Z^1$ is converted to an $R^4$ group.

"Abnormal cell growth", as used herein, unless otherwise indicated, refers to cell growth that is independent of normal regulatory mechanisms (e.g., loss of contact inhibition). This includes the abnormal growth of (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "alkenyl", as used herein, unless otherwise indicated, includes alkyl moieties having at least one carbon—carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes O-alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one to four heteroatoms each selected from O, S and N, wherein each heterocyclic group has from 4–10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromic heterocyclic groups are pyrrolidinyl, tetrahydrofuranyl, dihydrofuranyl, tetrahydrothienyl, tetrahydropyranyl, dyhdropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo]3.1.0]hexanyl, 3-azabicyclo[4.1.0]heptanyl, azabicyclo[2.2.2]hexanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl.

The phrase "pharmaceutically acceptable salt(s)", as used herein, unless otherwise indicated, includes salts of acidic or basic groups which may be present in the compounds of formula 1. The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, ie, salts containing pharmacologically acceptable anions, such as the acetate, benzenesulfonate, benzoate, bicarbonate, bisulfate, bitartrate, borate. bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts. Since a single compound of the present invention may include more than one acidic or basic moieties, the compounds of the present invention may include mono, di or tri-salts in a single compound.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

In the compounds of formula 1, where terms such as $(CR^1R^2)_q$ or $(CR^1R^2)_t$ are used, $R^1$ and $R^2$ may vary with each iteration of q or t above 1. For instance, where q or t is 2, the terms $(CR^1R^2)_q$ or $(CR^1R^2)t$ may equal —$CH_2CH_2$—, or —$CH(CH_3)C(CH_2CH_3)(CH_2CH_2CH_3)$—, or any number of similar moieties falling within the scope of the definitions of $R^1$ and $R^2$. Further, as noted above, any substituents comprising a $CH_3$ (methyl), $CH_2$ (methylene), or CH (methine) group which is not attached to a halogeno, SO or $SO_2$ group or to a N, O or S atom optionally bears on said group a substituent selected from hydroxy, $C_1$–$C_4$ alkoxy and —$NR^1R^2$.

In the above compounds of formula 1, where $R^4$ is —$(CR^1R^2)_r$—$CR^1R^{11}R^{12}$, the $R^{12}$ group is preferably linked through a carbon atom if it is a mono-cyclic ring, and it may be linked through either a carbon atom or a nitrogen if it is a bicyclic ring.

Certain compounds of formula 1 may have asymmetric centers and therefore exist in different enantiomeric forms. All optical isomers and stereoisomers of the compounds of formula 1, and mixtures thereof, are considered to be within the scope of the invention. With respect to the compounds of formula 1, the invention includes the use of a racemate, one or more enantiomeric forms, one or more diastereomeric forms, or mixtures thereof. The compounds of formula 1 may also exist as tautomers. This invention relates to the use of all such tautomers and mixtures thereof.

The subject invention also includes isotopically-labelled compounds, which are identical to those recited in Formula 1, but for the fact that one or more atoms are replaced by an atom having an atomic mass or mass number different from the atomic mass or mass number usually found in nature.-

Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

SCHEME 1

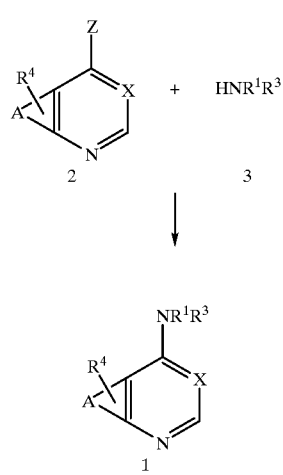

SCHEME 2

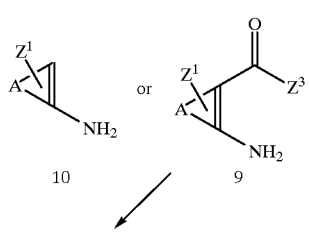

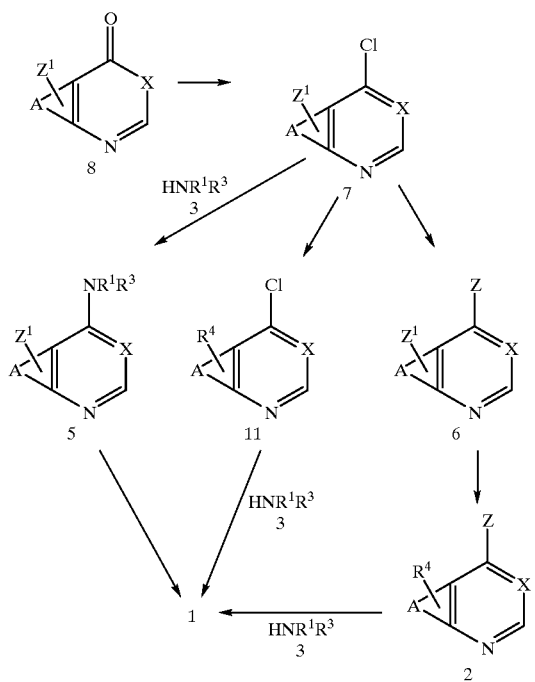

DETAILED DESCRIPTION OF THE INVENTION

General synthetic methods which may be referred to for preparing the compounds of the present invention are provided in U.S. Pat. No. 5,747,498 (issued May 5, 1998) U.S. patent application Ser. No. 08/953078 (filed Oct. 17, 1997), WO 98/02434 (published Jan. 22, 1998), WO 98/02438 (published Jan. 22, 1998), WO 96/40142 (published Dec. 19, 1996), WO 96/09294 (published Mar. 6, 1996), WO 97/03069 (published Jan. 30, 1997), WO 95/19774 (published Jul. 27, 1995) and WO 97/13771 (published Apr. 17, 1997). The foregoing patents and patent applications are incorporated herein by reference in their entirety. Certain starting materials may be prepared according to methods familiar to those skilled in the art and certain synthetic modifications may be done according to methods familiar to those skilled in the art. A standard procedure for preparing 6-iodoquinazolinone is provided in Stevenson, T. M., Kazmierczak, F., Leonard, N. J., J. Org. Chem. 1986, 51, 5, p. 616. Palladiumatalyzed boronic acid couplings are described in Miyaura, N., Yanagi, T., Suzuki, A. Syn. Comm. 1981, 11, 7, p. 513. Palladium catalyzed Heck couplings are described in Heck et. al. Organic Reactions, 1982, 27, 345 or Cabri et. al. in Acc. Chem. Res. 1995, 28, 2. For examples of the palladium catalyzed coupling of terminal alkynes to aryl halides see: Castro et. al. J. Org. Chem. 1963, 28, 3136. or Sonogashira et al. Synthesis, 1977, 777. For formation of alkyl and cycloalkylzinc reagents, those skilled in the art may refer to Rieke, R. D., Hanson, M. V., Brown, J. D., Niu, Q. J., J. Org. Chem., 1996, 61, 8, p. 2726. Azetidinyl zinc chemistry may be carried out using methods found in Billotte, S. Synlett, 1998, 379. Terminal alkyne synthesis may be performed using appropriately substituted/protected aldehydes as described in: Colvin, E. W. J. et. al. Chem. Soc. Perkin Trans. I, 1977, 869; Gilbert, J. C. et. al. J. Org. Chem., 47, 10, 1982; Hauske, J. R. et al. Tet. Lett., 33, 26, 1992, 3715; Ohira, S. et. al. J. Chem. Soc. Chem. Commun., 9, 1992, 721; Trost, B. M. J. Amer. Chem.

Soc., 119, 4, 1997, 698; or Marshall, J. A. et. al. J. Org. Chem., 62, 13, 1997, 4313.

Alternatively terminal alkynes may be prepared by a two step procedure. First, the addition of the lithium anion of TMS (trimethylsilyl) acetylene to an appropriately substituted/protected ketone or aldehyde as in: Nakatani, K. et. al. Tetrahedron, 49, 9, 1993, 1901. Subsequent deprotection by base may then be used to isolate the intermediate terminal 35 alkyne as in Malacria, M.; Tetrahedron, 33, 1977, 2813; or White, J. D. et. al. Tet. Lett., 31, 1, 1990, 59. Preparation of aryl amines such as phenoxyanilines, benzyloxyanilines, phenylsulfonylindoles, benzylindoles or benzylindazoles may be carried out by reduction of the corresponding nitro intermediates. Reduction of aromatic nitro groups may be performed by methods outlined in Brown, R. K., Nelson, N. A. J. Org. Chem. 1954, p. 5149; Yuste, R., Saldana, M, Walls, F., Tet. Lett. 1982, 23, 2, p. 147; or in WO 96/09294, referred to above. Nitro substituted N1-phenylsulfonylindoles/indazoles may be prepared by the methods found in Sundberg, R. J., Bloom, J. D., J. Org. Chem. 1980, 45, 17, p. 3382; Ottoni, O. et al. Tetrahedron, 1998, 54, 13915; or Boger, Dale L. et. al.; J. Org. Chem. 55, 4, 1990, 1379. Substituted nitro N-benzylindoles/indazoles may be prepared by methods found in Makosza, M.; Owczarczyk, Z.; J. Org. Chem., 54, 21,1989, 5094; Adebayo, Adelaide T. O. M. et al., J. Chem. Soc. Perkin Trans. 1,1989, 1415; or WO 98/02434, referred to above. Benzyloxy-nitrobenzene intermediates may prepared by methods found in WO 98/02434, referred to above. Alternatively, arylmethoxy, or aryloxy nitrobenzene derivatives may be prepared from halo nitrobenzene precursors by nucleophilic displacement of the halide with an appropriate alcohol as described in Dinsmore, C.J. et. al., Bioorg. Med. Chem. Lett., 7, 10, 1997, 1345; Loupy, A. et. al., Synth. Commun., 20, 18, 1990, 2855; or Brunelle, O. J., Tet. Lett., 25, 32, 1984, 3383.

Starting materials, the synthesis of which is not specifically described above, are either commercially available or can be prepared using methods well known to those of skill in the art.

In each of the reactions discussed or illustrated in the Schemes above, pressure is not critical unless otherwise indicated. Pressures from about 0.5 atmospheres to about 5 atmospheres are generally acceptable, and ambient pressure, ie., about 1 atmosphere, is preferred as a matter of convenience.

Where the compound of formula $HNR^1R^3$ is an optionally substituted indole or indoline moiety, such compounds can be prepared according to one or more methods known to those skilled in the art Such methods are described in PCT international patent application publication number WO 95/23141 and in W. C. Sumpter and F. M. Miller, "Heterocyclic Compounds with Indole and Carbazole Systems," in volume 8 of "The Chemistry of Heterocyclic Compounds", Interscience Publishers Inc., New York (1954). Optional substituents may be included as appropriate before or after the coupling step illustrated in Scheme 1. Prior to the coupling step, primary and secondary amino moieties (other than said amine of formula $HNR^1R^3$) are preferably protected using a nitrogen protecting group known to those skilled in the art. Such protecting groups and their use are described in T. W. Greene and P. G. M. Wuts, "Protective Groups in Organic Synthesis," Second Edition, John Wiley & Sons, New York, 1991.

With reference to Scheme 1 above, the compound of formula 1 may be prepared by coupling the compound of formula 2, wherein X, A, and $R^4$ are as defined above and Z is a leaving group, such as a substituted phenoxy derivative (such substituents may include halo, cyano, nitro, and/or $C_1$–$C_6$ alkyl groups) or chloro, with an amine of formula 3, wherein $R^1$ and $R^3$ are as defined above, in an anhydrous solvent solvent, in particular a solvent selected from DMF (N,N-dimethylformamide), DME (ethylene glycol dimethyl ether), DCE (dichloroethane), t-butanol, and phenol, or a mixture of the foregoing solvents, a temperature within the range of about 50–150° C. for a period ranging from 1 hour to 48 hours. The compound of formula 3 may be prepared by methods known to those skilled in the art, such as reduction of nitrites, reduction of imines or enamines, reduction of oximes, primary and secondary amides, reduction of a nitro group or reductive amination of either $R^1NH_2$ and $R^3CH(O)$ or $R^3NH_2$ and $R^3CH(O)$. The compound of formula 2 may be prepared by treating a compound of formula 4, referred to in Scheme 2, wherein $Z^1$ is an activating group, such as bromo, iodo, —$N_2$, or —OTF (which is —$OSO_2CF_3$), or the precursor of an activating group such as $NO_2$, $NH_2$ or OH., with a coupling partner, such as a terminal alkyne, terminal alkene, vinyl halide, vinyl stannane, vinylborane, alkyl borane, or an alkyl or alkenyl zinc reagent.

In the alternative, compounds of the formula 1 may be prepared according to the synthesis outlined in Scheme 2. In Scheme 2, a compound of formula 8 wherein X is NH may be prepared from a compound of formula 9, wherein A and $Z^1$ are as defined above and $Z^3$ is $NH_2$, $C_1$–$C_6$ alkoxy or OH, according to one or more procedures described in WO 95/19774, referred to above, and a compound of formula 8 wherein X is CH may be prepared from a compound of formula 10, wherein A and $Z^1$ are as defined above, according to the procedure described in WO 95/19774, referred to above. The compound of formula 8 may be converted to the compound of formula 7 by treating the starting compound with a chlorinating reagent, such as $POCl_3$ or ClC(O)C(O) Cl/DMF in a halogenated solvent at a temperature ranging from about 60° C. to 150° C. for a period ranging from about 2 to 24 hours. The compound of formula 7 may be converted to the compound of formula 6 wherein Z is a substituted phenoxy derivative by treating the starting compound with an appropriate metal phenyl oxide, such as sodium phenolate, in a solvent, such as DMF or phenol, at a temperature ranging from about 0° C. to 100° C. for a period ranging from about 2 to 24 hours. The compound of formula 6 may be reacted with a coupling partner such as a terminal alkyne, terminal alkene, vinyl halide, vinyl stannane, vinylborane, alkyl borane, or an alkyl or alkenyl zinc reagent, to provide a compound of the formula 2. The compound of formula 2 can then be transformed into a compound of formula 1 by coupling with an amine of the formula. Alternatively, the compound of formula 1 may be prepared by reaction of a terminal alkyne, terminal alkene, vinyl halide, vinyl stannane, vinylborane, alkyl borane, or an alkyl or alkenyl zinc reagent with a compound of the formula 7 to provide an intermediate of formula 11. Intermediate 11 can subsequently be coupled with an amine of the formula 3 to provide the compound of formula 1. Yet another alternative method for the synthesis of derivatives of formula 1 involves the coupling of chloro-quinazoline 7 with amine 3 followed by subsequent coupling of intermediate 5 with a terminal alkyne, terminal alkene, vinyl halide, vinyl stannane, vinylborane, alkyl borane, or an alkyl or alkenyl zinc reagent.

The compounds of the present invention may have asymmetric carbon atoms. Diasteromeric mixtures can be separated into their individual diastereomers on the basis of their physical chemical differences by methods known to those skilled in the art, for example, by chromatography or fractional crystallization. Enantomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of formulas 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula 1 that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula 1. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product. Since a single compound of the present invention may include more than one acidic or basic moieties, the compounds of the present invention may include mono, di or tri-salts in a single compound.

The compounds of the present invention are potent inhibitors of the erbB family of oncogenic and protooncogenic protein tyrosine kinases such as epidermal growth factor receptor (EGFR), erb82, HER3, or HER4 and thus are all adapted to therapeutic use as antiproliferative agents (ec.o, anticancer) in mammals, particularly in humans. In particular, the compounds of the present invention are useful in the prevention and treatment of a variety of human hyperproliferative disorders such as malignant and benign tumors of the liver, kidney, bladder breast, gastric, ovarian, colorectal, prostate, pancreatic, lung, vulval, thyroid, hepatic carcinomas sarcomas, glioblastomas, head and neck, and other hyperplastic conditions such as benign hyperplasia of the skin (ec.a, psoriasis) and benign hyperplasia of the prostate (eq., BPH) It is, in addition, expected that a compound of the present invention may possess activity against a range of leukemias and lymphoid malignancies.

The compounds of the present invention may also be useful in the treatment of additional disorders in which aberrant expression ligand/receptor interactions or activation or signalling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

The in vitro activity of the compounds of formula 1 may be determined by the following procedure.

The c-erbB2 kinase assay is similar to that described previously in Schrang et. al. Anal. Biochem. 211, 1993, p233–239. Nunc MaxiSorp 96-well plates are coated by incubation overnight at 37° C. with 100 mL per well of 0.25 mg/mL Poly (Glu, Tyr) 4:1 (PGT) (Sigma Chemical Co., St. Louis, Mo.) in PBS (phosphate buffered saline). Excess PGT is removed by aspiration, and the plate is washed three times with wash buffer (0.1% Tween 20 in PBS). The kinase reaction is performed in 50 mL of 50 mM HEPES (pH 7.5) containing 125 mM sodium chloride, 10 mM magnesium chloride, 0.1 mM sodium orthovanadate, 1 mM ATP, 0.48 mg/mL (24 ng/well) cerbB2 intracellular domain. The intracellular domain of the erbB2 tyrosine kinase (amino acids 674–1255) is expressed as a GST fusion protein in Baculovirus and purified by binding to and elution from glutathione coated beads. The compound in DMSO (dimethylsulfoxide) is added to give a final DMSO concentration of about 2.5%. Phosphorylation was initiated by addition of ATP (adenosine triphosphate) and proceeded for 6 minutes at room temperature, with constant shaking. The kinase reaction is terminated by aspiration of the reaction mixture and subsequent washing with wash buffer (see above). Phosphorylated PGT is measured by 25 minutes of incubation with 50 mL per well HRP-conjugated PY54 (Oncogene Science Inc. Uniondale, N.Y.) antiphosphotyrosine antibody, diluted to 0.2 mg/mL in blocking buffer (3% BSA and 0.05% Tween 20 in PBS). Antibody is removed by aspiration, and the plate is washed 4 times with wash buffer. The calorimetric signal is developed by addition of TMB Microwell Peroxidase Substrate (Kirkegaard and Perry, Gaithersburg, Md.), 50 mL per well, and stopped by the addition of 0.09 M sulfuric acid, 50 mL per well. Phosphotyrosine is estimated by measurement of absorbance at 450 nm. The signal for controls is typically 0.6–1.2 absorbance units, with essentially no background in wells without the PGT substrate and is proportional to the time of incubation for 10 minutes. Inhibitors were identified by reduction of signal relative to wells without inhibitor and $IC_{50}$ values corresponding to the concentration of compound required for 50% inhibition are determined.

The activity of the compounds of formula 1, in vivo, can be determine by the amount of inhibition of tumor growth by a test compound relative to a control. The tumor growth inhibitory effects of various compounds are measured according to the method of Corbett T. H., et al., "Tumor Induction Relationships in Development of Transplantable Cancers of the Colon in Mice for Chemotherapy Assays, with a Note on Carcinogen Structure", Cancer Res. 35, 2434–2439 (1975) and Corbett T. H., et al., "A Mouse Colon-tumor Model for Experimental Therapy", Cancer Chemother. Rep. (Part 2)", 5, 169–186 (1975), with slight modifications. Tumors are induced in the left flank by subcutaneous (sc) injection of 1–5 million log phase cultured tumor cells (murine FRE-ErbB2 cells or human SK-OV3 ovarian carcinoma cells) suspended in 0.1 ml RPMI 1640 medium. After sufficient time has elapsed for the tumors to become palpable (100–150 mm3 in size/5–6 mm in diameter) the test animals (athymic female mice) are treated with test compound (formulated at a concentration of 10 to 15 mg/ml in 5 Gelucire) by the intraperitoneal (ip) or oral (po) route of administration once or twice daily for 7 to 10 consecutive days. In order to determine an anti-tumor effect, the tumor is measured in millimeters with a Vernier caliper across two diameters and the tumor size (mm3) is calculated using the formula: Tumor size (mm3)=(length× [width]2)/2, according to the methods of Geran, R. I., et al. "Protocols for Screening Chemical Agents and Natural Products Against Animal Tumors and Other Biological Systems", Third Edition, Cancer Chemother. Rep., 3, 1–104 (1972). Results are expressed as percent inhibition, according to the formula: Inhibition (%)=(TuW$_{control}$−TuW$_{test}$) ITuW$_{control}$×100%. The flank site of tumor implantation provides reproducible doselresponse effects for a variety of chemotherapeutic agents, and the method of measurement (tumor diameter) is a reliable method for assessing tumor growth rates.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cis-platin, carboplatin and cyclophosphamide; antimetabolites, for example 5-fluorouracil, cytosine arabinoside and hydroxyurea, or, for example, one of the preferred anti-metabolites disclosed in European Patent Application No. 239362 such as N-(5-LN3, 4-dihydro-2-methyl-4-oxoquinazolin-6-ylmethyl)—N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifylng agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences,* Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers.

Single enantiomersldiastereomers may be obtained by methods known to those skilled in the art.

Where HPLC chromatography is referred to in the preparations and examples below, 20 the general conditions used, unless otherwise indicated, are as follows. The column used is a ZORBAX™ RXC$_{18}$ column (manufactured by Hewlett Packard) of 150 mm distance and 4.6 mm interior diameter. The samples are run on a Hewlett Packard-1100 system. A gradient solvent method is used running 100 percent ammonium acetate/acetic acid buffer (0.2M) to 100 percent acetonitrile over 10 minutes. The system then proceeds on a wash cycle with 100 percent acetonitrile for 1.5 minutes and then 100 percent buffer solution for 3 minutes. The flow rate over this period is a constant 3 ml/minute.

In the following examples and preparations, "Et" means ethyl, "Ac" means acetyl, "Me" means methyl, and "Bu" means butyl.

Preparation of 3methyl-4-phenoxynitrobenzene

Sodium hydride (95% dry powder) (83.62 g, 3.31 moles, 1.3 eq.) was charged under nitrogen atmosphere to a clean and dry 12 L four neck flask equipped with a condenser, a dropping funnel, a mechanical stirrer and two nitrogen inlet-outlet bubblers (Caution: sodium hydride is pyrophoric, avoid contact with water or moisture). The reaction flask was cooled to 0° C. (ice bath) then anhydrous DMF (1280 mL) was carefully added using a dropping funnel. The reaction mixture was stirred for 30 minutes at 0° C., then a solution of phenol (263.5 g, 2.8 moles, 1.1 eq.) in anhydrous DMF (1280 mL) was added using a dropping funnel over 2 hours (Caution: exothermic, vigorous hydrogen evolution). After complete addition, the reaction mixture was stirred for 40 minutes at 0° C. (the reaction mixture turned to a white slurry), then a solution of 3-methyl-4-fluoronitrobenzene (390.0 g, 2.51 moles, 1.0 eq.) in anhydrous DMF (dimethylformamide)(1280 mL) was added dropwise over 1 hour. The reaction mixture was slowly warmed to room temperature and stirred at room temperature for 15–22 hours (dark-brown viscous solution) until all the starting material was converted to the phenoxynitrotoluene (TLC, 2% ethyl acetate in hexanes). Again the reaction mixture was cooled to 0° C. (ice bath), then carefully quenched with cold water (5000 mL) over 2 hours (Caution: exothermic, hydrogen evolution; first 100 ml water was added over 90 minutes). The reaction mixture was stirred for 1 h, then transferred to a two 50 L carboys, each containing 40 L of water. The contents was stirred and left at room temperature for 24 hours to afford the phenoxynitrotoluene, as a yellow solid. The yellow solid was filtered, washed with excess of water and air dried to afford 3-methyl-4-phenoxynitrobenzene (552 g, 96% yield). The crude 3-methyl-4-phenoxynitrobenzene was found to be pure by $^1$H and $^{13}$C NMR spectra, and used as such in the next reaction; m p 51–52° C.; FT-IR (cm$^{-1}$): 1582, 1509, 1480, 1339, 1242, 1204, 1091 and 796; $^1$H NMR (300 MHz, CDCl$_3$) δ 2.41 (s, 3 H), 6.78 (d, 1H, J =8.7 Hz), 7.02–7.08 (m, 2 H), 7.19–7.29 (m, 1H), 7.38–7.46 (m, 2 H), 7.99 (dd, 1H, J =9.15 Hz, 2.7 Hz); $^{13}$C NMR (75.45 MHz, CDCl$_3$) 16.22, 115.93, 119.11, 123.17, 124.9, 126.79, 129.53, 130.28, 142.66, 155.44 and 161.4.

Preparation of 3-methyl-4-phenoxyanlline hydrochloride

To a stirred solution of 3-methyl-4-phenoxynitrobenzene (2) (548 g, 2.39 moles, 1.0 eq.) in methanol (5 L) was added 10% Pd/C (100 g, 50% wet, 46.98 mmol, 0.02 eq.). Then the reaction mixture was stirred under a hydrogen atmosphere (60–80 psi) for 15–16 hours at room temperature in a 2 gallon Parr hydrogenator. The progress of the reaction was monitored by TLC (50% ethyl acetate in hexanes, sm Rf=0.69, pr Rf=0.47, UV visible). Then the reaction mixture was filtered through Celite, and the solid was washed with excess methanol. The filtrate was concentrated under reduced pressure to give 3-methyl-4-phenoxyaniline as a pale brown viscous liquid (451.0 9, 95%). The 3-methyl-4-phenoxyaniline was found to be pure by $^1$H and $^{13}$C NMR spectra, and used as such in the next reaction.

To a cooled (0° C.) and stirred solution of 3-methyl-4-phenoxyaniline (451.0 g, 2.26 moles, 1.0 eq.) in anhydrous ether (12 L) was bubbled dry HCl gas for 40–90 minutes until all the starting material was converted to the aniline hydrochloride salt. The off-white solid was filtered, washed with ether and dried in a vacuum oven for 6 hours at 60° C. to afford 3-methyl-4-phenoxyaniline hydrochloride (511.8 g, 96%); m p 173–174° C.; FT-IR (cm$^{-1}$): 3058, 3019, 2840, 2573, 1485, 1253, 1223 and 691; $^1$H NMR (300 MHz, CDCl$_3$) δ 2.22 (s, 3 H), 6.81–6.9 (m, 3 H), 7.04–7.11 (m, 1H), 7.25–7.37 (m, 3 H), 7.43 (d, 1H, J =2.4 Hz), 10.45 (s, 3 H); $^{13}$C NMR (75.45 MHz, CDCl$_3$) 16.03, 118.01, 119.9, 122.12, 123.35, 124.78, 126.13, 129.93, 131.89, 155.5 and 158.96; APCI (negative FAB) 200.3 (100%); Anal. Calcd for $C_{13}H_{14}ClNO$: C, 66.24; H, 5.99; N, 5.94. Found: C, 60.05; H, 6.01; N, 5.98.

Examples of other amines prepared by the above methods are:

3-Chloro4-phenoxy-phenylamine
3-Methoxy-4-phenoxy-phenylamine
4-Phenoxy-3-trifluoromethyl-phenylamine
3-Fluoro4-phenoxy-phenylamine
5-Amino-2-phenoxy-benzonitrile
4-(2-Methoxy-phenoxy)-3-methyl-phenylamine
4-(3-Methoxy-phenoxy)-3-methyl-phenylamine
4-(4-Methoxy-phenoxy)-3-methyl-phenylamine
4-(2-Fluoro-phenoxy)-3-methyl-phenylamine
4-(3-Fluoro-phenoxy)-3-methyl-phenylamine
4-(4-Fluoro-phenoxy)-3-methyl-phenylamine
4-(2-Methyl-phenoxy)-3-methyl-phenylamine
4-(3-Methyl-phenoxy)-3-methyl-phenylamine
4-(4-Methyl-phenoxy)-3-methyl-phenylamine
4-(2,6-Difluoro-phenoxy)-3-methyl-phenylamine
3,5-Dichloro-4-phenoxy-phenylamine
3,Methyl-4-phenylsulfanyl-phenylamine
4- phenylsulfanyl-phenylamine
4-Cyclohexyloxy-3-methyl-phenylamine
4-Cyclopentyloxy-3-methyl-phenylamine
4-Cyclobutyloxy-3-methyl-phenylamine
2-Fluoro-4-phenoxymeamine
4-Fluoro-2-phenoxyamine
3-Bromo-4-phenoxy-phenylamine
4-(2-Chloro-phenoxy)-3-methyl-phenylamine
4-(2-Methoxy-phenoxy)-3-methyl-phenylamine
4-(2-Ethyl-phenoxy)-3-methyl-phenylamine
4-(2-Trifluoromethyl -phenoxy)-3-methyl-phenylamine
1-(5-amino-2-phenoxy-phenyl)-ethanone
(+/−)-4-Benzenesulfinyl-3-methyl-phenylamine, (+/−) 4-Benzenesulfinyl-phenylamine, 4-Benzenesulfonyl-3-methyl-phenylamine, 4-Benzenesulfonyl-phenylamine were prepared from 3-Methyl-4-phenylsulfanyl-phenylamine and 4-phenylsulfanyl-phenylamine by oxidation methods known to those skilled in the art
3-Ethyl-4-phenoxy-phenylamine To a solution of 1-(5-amino-2-phenoxy-phenyl)ethanone (0.5 g, 2.20 mmol ) in THF (15 ml) was added sodium borohydride(0.4 g, 10.5 mmol ) and AlCl$_3$ (anhydrous) (0.803 g, 6.02 mmol ) under nitrogen. The resulting reaction mixture was heated under reflux for 4 hours. Th e mixture was then cooled and iced-water added. The resultant mixture was extracted with EtOAc and dried over Na$_2$SO$_4$. Removal of the solvent afforded a brownish residue which was chromatographed with 4:1 hexane/EtOAc to afford (15 mg, 10%) product 3-ethyl-4-phenoxy-phenylamine.

3-Hydroxy-4-phenoxy-phenylamine 3-methoxy-4-phenoxynitrobenzene(2 g, 8.15 mmol) was treated with 48% HBr (20 ml) and HOAc (20 ml), The reaction mixture was heated to 110° C. for 24 hours and then the reaction mixture was poured into ice and extracted with EtOAc, the organic layer was washed with brine, dried over $Na_2SO_4$. Removal of the solvent provided a brownish residue 5—Nitro-2-phenoxy-phenol which was taken to next step without further purification. (almost quantitative yield). $^1H$ NMR($CDCl_3$): δ 7.91(d,1H, 2.7 Hz), 7.72(dd, 1H, J1=8.8 Hz, J2=2.4 Hz), 7.43(t, 2 H, J=7.9 Hz), 7.28(d, 1H, 7.9 Hz), 7.10(d, 1H, J=8.3 Hz), 6.78(d, 2H, J=8.9 Hz).

Ethoxy-4-phenoxy-phenylamine

To a solution of 5-nitro-2-phenoxy-phenol (500 mg,2.16 mmol ) in acetone(20 ml) was added bromoethane (0.353 g, 3.26 mmol ) and potassium carbonate (0.447 g, 3.26 mmol). The resulting reaction mixture was stirred at room temperature for 2 hours and then the reaction was heated to 50° C. for 4 hours. Water was added and aqueous layer extracted with EtOAc (3×30 ml), the organic layer washed with brine and dried over $Na_2SO_4$. Removal of the solvent provided (0.3 g, 53%) 3-ethoxy-4-pheoxy-nitrobenzene. The product was subjected to hygrogenation over % Pd-C in methanol to afford (0.1 g, 38% ) of 3-Ethoxy-4-phenoxy-phenylamine. M/z, 230.0, $^1H$ NMR($CDCl_3$): 7.91(d,1H, 2.7 Hz), 7.72(dd, 1H, J1=8.8 Hz, J2=2.4 Hz), 7.43(app t, 2 H, J=7.9 Hz), 7.28(d, 1H, 7.9 Hz), 7.10(d, 1H, J=8.3 Hz), 6.78(d, 2H, J=8.9 Hz), 4.17 (dd, 2H, J1=13. 9 HZ, J2=7.1 Hz), 1.42(t, 3H, J=7.1 Hz).

3-isopropoxy-4-phenoxy-phenylamine was also prepared by the above alkylation protocol.

3-Phenyl-1H-lndazol-6-ylamine

To a solution of 2-chloro-5-nitro-benzophenone(1.0 g) in THF (tetrahydrofuran) (15 ml) was added anhydrous hydrazine(120 mg). The resulting reaction mixture was kept stirring at room temperature for 2–4 hours. The solvent was removed in vacuo and the residue dissolved in EtOAc, washed with water and brine, dried over $Na_2SO_4$. Removal of the solvent afforded (0.8 g, 88%) product 6-Nitro-3-phenyl-1H-indazole(5). 6-Nitro-3-phenyl-1H-indazole was hydrogenated over $H_2$/Pd and gave 0.5 9 of 3-phenyl-1H-indazol-6-ylamine (71.5%). M/z: 210.0. $^1H$ NMR($CD_3OD$): 7.86(d, 2H, J=7.9 Hz), 7.47( t, J=8.1 Hz), 7.35(t, 3H, J=8.7 Hz), 7.01 (d, 1H, J=8.7 Hz).

General Procedure for the Addition of 1-Lithio-2-trimethylsilylacetylene to a Carbonyl A cold (−78 ° C.), stirred solution of (trimethylsilyl) acetylene (1.2 eq) in anhydrous THF was treated with nBuLi (1.2 eq) under nitrogen (In the case of BOC-protected amino aldehydes containing a free NH, the amount of (trimethylsilyl)acetylene and n-BuLi is doubled.). The colorless solution was stirred for 30 to 40 minutes, followed by the addition of carbonyl compounds (1.0 eq) in anhydrous THF. The reaction was warmed up to room temperature, stirred for 2 to 4 hours, and quenched with water. After removal of THF, the residue was partitioned between ether or EtOAc and water. The separated organic layer was washed with brine, dried over sodium sulfate, and concentrated to give the crude TMS protected propargyl alcohol. Subsequently, a mixture of the crude propargyl alcohol (1.0 eq) and $K_2CO_3$ (2.0 eq) in methanol was stirred at room temperature for 0.5 to 1 hour. The solids was filtered off and washed with ether. The filtrate was concentrated, dissolved in ether, washed with water and brine, and dried over sodium sulfate. Solvent removal gave the crude terminal acetylene product, which was purified by distillation or chromatography (Ethyl Acetate/Hexanes). Overall yields for this procedure range from 62–97%.

Examples of terminal alkynes prepared by above method are:

3-Ethynyl-3-hydroxy-piperidine-1-carboxylic acid tert-butyl ester

4-Ethynyl-4-hydroxy-piperidine-1-carboxylic acid tert-butyl ester

3-Ethynyl-3-hydroxy-pyrrolidine-1-carboxylic acid tert-butyl ester endo-α-3-Ethynyl-3-hydroxy-8-aza-bicyclo[3.2. 1]octane-8-carboxylic acid tert-butyl ester exo-β-3-Ethynyl-3-hydroxy-8-aza-bicyclo[3.2.1]octane-8-carboxylic acid tert-butyl ester 2-(1-Hydroxy-prop-2-ynyl)-pyrrolidine-1-carboxylic acid tert-butyl ester 1-Cyclobutyl-prop-2-yn-1-ol Pent-1-yn-3-ol 4-Amino-pent-1-yn-3-ol 1-(3-Aza-bicyclo(3.1.0]hex-8-yl)-prop-2-yn-1-ol 4-Ethynyl-tetrahydro-pyran-4-ol (4-Ethynyl-tetrahydro-pyran4-yl)arbamic acid tert-butyl ester 2-(1-Hydroxy-prop-2-ynyl)-piperidine-1-carboxylic acid tert-butyl ester 3-(1-Hydroxy-prop-2-ynyl)-piperidine-1-carboxylic acid tert-butyl ester 4-Ethynyl-1-methyl-piperidin-4-ol (2-Hydroxy-but-3-ynyl)-methyl-carbamic acid tert-butyl ester (2-Ethynyl-2-hydroxy-cyclohexyl)arbamic acid tert-butyl ester R and S-3-Ethynyl-1-aza-bicyclo[2.2.2]octan-3-ol General Procedure Homologating Aldehydes to Terminal Alkynes To a cold (−78 ° C.), stirred solution of LDA (lithium diisopropylamide) (1.3 eq) in anhydrous THF was added a solution of (trimethylsilyl)diazomethane in hexane (1.3 eq) dropwise under nitrogen (In the case of BOC-protected amino aldehydes containing a free NH, the amount of (trimethylsilyl)diazomethane and LDA is doubled.). After 1 hour, aldehyde (1.0 eq) in anhydrous THF was introduced and cooling bath was removed. The reaction was stirred at rt for 1 to 2 hours, quenched with water, concentrated, and partitioned between ether and water. The separated organic layer was washed with brine, dried over sodium sulfate, and concentrated to give the crude product, which was purified by distillation or chromatography (Ethyl Acetate/Hexanes). Overall yields for this procedure range from 37–72%.

Examples of terminal alkynes prepared by this method are:

4-Ethynyl-piperidine-1-carboxylic acid tert-butyl ester

3(S)-Ethynyl-piperidine-1-carboxylic acid tert-butyl ester

3(R)-Ethynyl-piperidine-1-carboxylic acid tert-butyl ester

2-Ethynyl-piperidine-1-carboxylic acid tert-butyl ester

3-Ethynyl-pyrrolidine-1-carboxylic acid tert-butyl ester

3-Ethynyl-azetidine-1-carboxylic acid tert-butyl ester (4-Ethynyl-tetrahydro-pyran4-yl)-carbamic acid tert-butyl ester

[1-(tert-Butyl-dimethyl-silanyloxymethyl)-prop-2-ynyl] carbamic acid tert-butyl ester 4-Prop-2-ynyl-oiperazine-1-carboxylic acid tert-butyl ester To a solution of N-t-butoxycarbonypiperazine (5.0 g, 26.8 mmol) in acetone (40 ml) was added potassium carbonate (3.70 g, 26.8 mmol). Propargyl bromide (2.39 ml, 26.8 mmol) in acetone (10 ml) was added dropwise to the above reaction mixture. The resultant mixture was allowed to stir at room temperature for overnight. Water was added, the aqueous layer extracted with ether and combined organic layer washed with brine, dried over sodium sulfate and concentrated in vacuo to afford 4-prop-2-ynyl-piperazine-1-carboxylic acid tert-butyl ester which as crude material is taken on into a Pd coupling reaction with the appropriate anilinoquinazoline.

Examples of terminal alkynes prepared by this method are:

1-Prop-2-ynyl-pyrrolidine

3-Methyl-4-prop-2-ynyl-piperazine-1-carboxylic acid tert-butyl ester 3,5-Dimethyl-4-prop-2-ynyl-piperazine-1-carboxylic acid tert-butyl ester 1-Methyl-4-prop2-ynyl-piperazine 4-Prop-2-ynyl-morpholine (3-Prop-2-ynyl-3-aza-bicyclo[3.1.0]hex8-yl)-methanol 1-Prop-2-ynyl-piperldin-4-ol 1-Prop-2-ynyl-piperidin-3-ol 1-Prop-2-ynyl-pyrrolidin-3-ol (1-Prop-2-ynyl-piperidin-4-yl)-methanol (1-Prop-2-ynyl-piperidin-3-yl)-methanol (1-Prop-2-ynyl-piperidin-2-yl)-methanol (1-Prop-2-ynyl-pyrrolidin-2-yl)-methanol 2-(1-Prop-2-ynyl-piperidin-4-yl)-ethanol 2-(4-Prop-2-ynyl-piperazin-1-yl)-ethanol 4,4-Dimethoxy-1-prop-2-ynyl-piperidine 1-Prop-2-ynyl-piperidin-4-ylamine 2-(Methyl-prop-2-ynyl-amino)-ethanol 4-Prop-2-ynyl-piperazine-1-carboxylic acid methylamide 1-(4-Prop-2-ynyl-piperazin-1-yl)-ethanone 4-Prop-2-ynyl-piperazine-1-carboxamide 1-Methanesulfonyl-4-prop-2-ynyl-piperazine 2-Chloro-N-prop-2-ynyl-acetamide Propargyl amine (250 mg; 0.34 ml; 4.6 mmol) was dissolved in dichloromethane (10 ml) and cooled to 0° C. Chloro-acetyl chloride (256 mg; 0.18 ml; 2.3 mmol) was added to this solution dropwise and the solution was stirred for 30 minutes and allowed to warm up to room temperature. The solution was washed with 2×H$_2$O, dried over Na$_2$SO$_4$ and the solvent removed. 2-Chloro-N-prop-2-ynyl-acetamide (385 mg) was obtained as white crystals. $^1$H NMR (400 MHz; CDCl$_3$) δ 2.27 (1H, m), 4.07 (2H, s), 4.09 (2H, q, J=2.5 Hz), 6.78 (1H, br s).

Examples of terminal acetylenes prepared by the above method are:

N-Prop-2-ynyl-acetamide

N-Prop-2-ynyl-propionamide

Cyclopropanecarboxylic acid prop-2-ynylamide 2,2-Dimethyl-N-prop-2-ynyl-propionamide N-Prop-2-ynyl-methanesulfonamide N-Methyl-N-prop-2-ynyl-acetamide N-(1-Methyl-prop-2-ynyl)-acetamide N-(1,1-Dimethyl-prop-2-ynyl)-acetamide 2-Methoxy-N-prop-2-ynyl-acetamide 2-(tert-Butoxycarbonylamino)-2-methyl-1-propanol A mixture of 2-amino-2-methyl-1-propanol (8.9 g, 0.1 mol), di-tert-butyldicarbonate (22.0 g, 0.1 mol), and N3$_2$CO$_3$ (21.0 g, 0.2 mol) in water/THF (150/150 mL) was refluxed for 1 hour. After removal of THF, the residue was partitioned between ether (200 mL) and water (150 mL). The separated organic layer was washed with brine (100 mL), dried over sodium sulfate, and concentrated to give 17.97 g (95%) of 2-(tert-butoxycarbonylamino)-2-methyl-1-propanol as waxy, white solid: $^1$H NMR (CDCl$_3$) δ 1.23 (s, 6H), 1.41 (s, 9H), 3.56 (s, 2H).

2-(tert-butoxycarbonylamino)-2-methyl propionaldehyde

To a solution 2-(tert-Butoxycarbonylamino)-2-methyl-1-propanol (5.7 g, 30.0 mmol) in triethylamine (42 mL) was added a mixture of sulfur trioxide pyridine complex (14.3 g, 90.0 mmol) in anhydrous DMSO (dimethylsulfoxide) (50 mL) at room temperature. The reaction was stirred for 1 hour under nitrogen and concentrated. The residue was dissolved in EtOAc (200 mL), washed with water (100 mL) and brine (100 mL), dried over sodium sulfate and concentrated to give crude 2-(tert-butoxycarbonylamino)-2-methyl propionaldehyde as yellow oil. Purification by distillation afforded 4.90 9 (87%) of waxy, white solid: $^1$H NMR (ODCl$_3$) δ 1.30 (s, 6H), 1.41 (s, 9H), 4.97 (br, 1H), 9.40 (s, 1H).

4,4-Dimethyl-5-trimethylsilylethynyl-2-oxazolidinone

A cold (−78 ° C.), stirred solution of (trimethylsilyl) acetylene (4.42 g, 45.0 mmol) In anhydrous THF (20 mL) was treated with nBuLi (18 mL, 45.0 mmol) under nitrogen. The colorless solution was stirred for 30 minutes and followed by the addition of 2(tert-butoxycarbonylamino)-2-methyl propionaldehyde (2.80 g, 15 mmol) in anhydrous THF (20 mL). The reaction was warmed up to room temperature, stirred for 2 hours, and quenched with water. After removal of THF, tne residue was partitioned between ether (150 mL) and water (100 mL). The separated organic layer was washed with brine (100 mL), dried over sodium sulfate, and concentrated to give the crude 4,4-Dimethyl-5-trimethylsilylethynyl-2-oxazolidinone (100%) as yellow oil which was carried to the next step.

4,4Dimethyl-5-ethynyl-2-oxazolidinone

A mixture of 4,4-Dimethyl-5-trimethylsilylethynyl-2-oxazolidinone (15.0 mmol) and K$_2$CO$_3$ (4.1 g, 30.0 mmol) in methanol (30.0 mL) was stirred at room temperature for 30 min. The solid was filtered off and washed with ether. The filtrate was concentrated, dissolved in ether (100 mL), washed with water (50 mL) and brine (50 mL), and dried over sodium sulfate. Solvent removal afforded 1.10 g (53%) of 4,4-Dimethyl-5-ethynyl-2-exazolidinone as a yellow oil: $^1$H NMR (CDCl$_3$) δ 1.37 (s, 3H), 1.39 (s, 3H), 2.68 (s, 1H), 4.82 (s, 1H), 6.00 (br s, 1H).

Preparation of 4-Ethynyl-4-hydroxy-tetrahydro-pyran-2-carboxylic acid amide

4-Oxo-3,4-dihydro-2H-pyran-2-carboxylic acid ethyl ester: ZnCl (0.63 g, 4.6 mmol) was dissolved in anhydrous THF (15 mL) and added to a solution of 1-methoxy-3-(trimethylsilyloxy)-1,3-butadiene (7.94 g, 46.0 mmol) and ethyl glyoxalate (7.05 g, 69.0 mmol) in totuene (30 mL) at room temperature. After stirring for 30 minutes, water (30 mL) and TFA (trifluoracetic acid) (2 mL) were added and the mixture was stirred vigorously for 20 min. After concentration, the residue was partitioned between EtOAc (200 mL) and water (100 mL). The separated organic layer was washed with brine, dried over sodium sulfate, and concentrated to give 8.0 g (100%) of brown oil which was carried to the next step without further purification. $^1$H NMR (CDCl$_3$) δ 1.30 (t, 3H), 2.85 (d, 2H), 4.26 (q 2H), 5.00 (t, 1H), 5.48 (d, 1H), 7.39 (d, 1H).

4-Oxo-tetrahydro-pyran-2-carboxylic acid ethyl ester: A mixture of 4-oxo-3,4-dihydro-2H-pyran-2-carboxylic acid ethyl ester (8.0 g, 46.0 mmol) and Pd/C (10%, 0.20 g) in EtOAc (70 mL) was shaken in a Parr bottle with hydrogen at 50 psi overnight and filtered through a pad of Celite. The filtrate was concentrated and the residue was distilled to give 2.62 g (33%) of yellowish oil: $^1$H NMR (CDCl$_3$) δ 1.29 (t, 3H), 2.40 (d, 1H), 2.58–2.75 (m 3H), 3.79 (tt, 1H), 4.23 (q, 2H), 4.28 (m 1H), 4.40 (m, 1H).

4-Hydroxy-4-trimethylsilanylethynyl-tetrahydro-pyran-2-carboxyllc acid ethyl ester: A cold (−78° C.), stirred solution of (trimethylsilyl)acetylene (1.80 g, 18.24 mmol) in anhydrous THF (30 mL) was treated with nBuLi (7.3 mL in hexane, 18.24 mmol) under nitrogen. The colorless solution was stirred for 30 minutes and followed by the addition of 4-oxo-tetrahydro-pyran-2-carboxylic acid ethyl ester (2.62 g, 15.2 mmol) in anhydrous THF (30 mL). The reaction was warmed up to room temperature, stirred for 2 hours, and quenched with water (30 mL). After removal of THF, the product was extracted with EtOAc (2×60 mL). The combined organic layer was washed with brine, dried over sodium sulfate, and concentrated to give 2.50 g (61%) of yellow oil: $^1$H NMR (CDCl$_3$) δ 0.17 (s, 9H), 1.30 (t, 3H), 1.76–1.90 (m, 3H), 2.25 (m, 1H), 3.66 (tt, 1H), 4.11–4.21 (m, 2H), 4.24 (q, 2H).

4-Ethynyl-4-hydroxy-tetrahydro-pyran-2-carboxylic acid amide: 4-Hydroxy-4-trimethylsilanylethynyl-tetrahydro-pyran-2-carboxylic acid ethyl ester (2.50 g, 9.25 mmol) was dissolved in MeOH (20 mL) in a pressure reaction tube and NH$_3$ gas was passed through the solution for 10 minutes with stirring. The tube was tightly capped and the reaction was stirred for 3 days. After solvent removal, 1.53 g (97%) of yellow oil was obtained: $^1$H NMR (CD$_3$OD) δ 1.48 (t, 1H), 1.70 (td, 1H), 1.85 (d, 1H), 2.30 (d, 1H), 3.04 (s, 1H), 3.29 (s, 1H), 3.71(t, 1H), 3.98 (d, 1H), 4.06 (dt, 1H).

Preparation of 2-(tert-Butyl-dimethyl-silanyloxymethyl)-4-ethynyl-tetrahydro-pyran-4-ol 2-Hydroxymethyl-tetrahydro-pyranol: To a cooled (0° C.), stirred suspension of LiAlH$_4$ (3.42 g, 90.0 mmol) in anhydrous THF (50 mL) was added dropwise a solution of 4-oxo-tetrahydro-pyran-2-carboxylic acid ethyl ester (5.17 g, 30.0 mmol). After stirring for 1 hour, the reaction was quenched by the slow, sequential addition of water (3.4 mL), 15% NaOH (3.4 mL), and water (10.0 mL). The inorganic salt was filtered off and extracted with EtOAc repeatedly since the product was absorbed on the solid. Solvent removal afforded 2.42 g (61%) of yellow oil. The crude mixture was carried to the next step without purification.

2-(tert-Butyl-dimethyl-silanyloxymethyl)-tetrahydro-pyran-4-ol: To a solution of 2-hydroxymethyl-tetrahydro-pyran-4-ol (2.42 g, 18.3 mmol), DMAP (4-dimethylaminopyridine) (90 mg, 0.74 mmol), and Et$_3$N (2.04 g, 20.1 mmol) in anhydrous CH$_2$Cl$_2$ (50 mL) was added tert-butyldimethylsilyl chloride (2.76 g, 18.3 mmol) at room temperature. After stirring overnight, the reaction solution was quenched with brine (30 mL) and the separated aqueous layer was extracted with CH$_2$Cl$_2$ (40 mL). The combined organic extract was dried over sodium sulfate and concentrated. Purification by silica gel column using 30% EtOAc in hexane gave 2.27 g (50%) of colorless oil: 1H NMR (CDCl$_3$) δ 0.04 (s, 6H), 0.88 (s, 9H), 1.21 (m, 1H), 1.43 (m, 1H), 1.82 (dt, 1H), 2.00 (dt, 1H), 3.35 (m, 1H), 3.51 (q, 1H), 3.66 (q, 1H). 3.79 (m, 1H), 4.01 (m, 1H).

2-(tert-Butyl-dimethyl-silanyloxymethyl)-tetrahydro-pyran4-one: A solution of 2-(tert-butyl-dimethyl-silanyloxymethyl)-tetrahydro-pyran-4-ol (2.27 g, 9.21 mmol) in anhydrous DMSO/Et$_3$N (15/13 mL) was treated with sulfur trioxide pyridine complex (7.33 g, 46.1 mmol) portionwise at room temperature. After stirring for 1 hour, the reaction was concentrated and the residue was partitioned between EtOAc (100 mL) and water (50 ml). The separated organic layer was washed with brine (70 mL), dried over sodium sulfate, and concentrated. Purification by silica gel column using 10–20% of EtOAc in hexane afforded 1.48 g (66%) of colorless oil: $^1$H NMR (CDCl$_3$) δ 0.05 (s, 6H), 0.88 (s, 9H), 2.32 (dt, 1H), 2.41 (m, 2H), 2.58 (m, 1H), 3.62 (m, 2H), 3.70 (d, 2H), 4.31 (m, 1H).

2-(tert-Butyl-dimethyl-silanyloxymethyl)-4-trimethylsilanylethynyltetrahydro-pyran-4-ol: A cold (−78 ° C.), stirred solution of (trimethylsilyl)acetylene (1.01 g, 10.3 mmol) in anhydrous THF (25 mL) was treated with nBuLi (4.12 mL in hexane, 10.3 mmol) under nitrogen. The colorless solution was stirred for 30 minutes and followed by the addition of 2-(tert-butyl-dimethyl-silanyloxymethyl)-tetrahydro-pyran-4-one (1.48 g, 6.06 mmol) in anhydrous THF (25 mL). The reaction was warmed up to room temperature, stirred for 2 hours, and quenched with water (30 mL). After removal of THF, the product was extracted with EtOAc (2×50 mL). The combined organic layer was washed with brine, dried over sodium sulfate, and concentrated to give 1.75 g (84%) of yellow oil: $^1$H NMR (CDCl$_3$) δ 0.05 (s, 6H), 0.16 (s, 9H), 0.89 (s, 9H), 1.43 (m, 1H), 1.78 (td, 1H), 1.83 (d, 1H), 1.94 (d, 1H), 3.52–3.70 (m, 4H), 4.00 (m 1H).

4-(tert-Butyl-dimethyl-silanyloxymethyl)-4-ethynyl-tetrahydro-pyran-4-ol: A mixture of 2-(tert-butyl-dimethyl-silanyloxymethyl)-4-trimethylsilanylethynyl-tetrahydro-pyran-4-ol (1.75 g, 5.1 mmol) and K$_2$CO$_3$ (1.4 g, 10.2 mmol) was stirred at room temperature for 30 minutes. After concentration, the residue was partitioned between EtOAc (50 mL) and water (30 mL) and the separated aqueous layer was extracted with EtOAc. The combined organic extract was dried over sodium sulfate and concentrated to give 1.33 g (96%) of light yellow oil: $^1$H NMR (CDCl$_3$) δ 0.05 (s, 6H), 0.88 (s, 9H), 1.50 (m, 1H), 1.78 (m, 1H), 1.84 (d, 1H), 2.01 (m, 1H), 2.55 (s, 1H), 3.55–3.70 (m, 4H), 4.00 (m, 1H).

6-iodo-4-quinazolinone

A solution of 2-amino-5-iodobenzoic acid (26.3 g, 100 mmol) and formamidine acetate (13.5 g, 130 mmol) in ethanol (400 mL) was refluxed for 20 hours. After cooling to 0° C., the solid product was collected by filtration. Further drylng in vacuo provided 6-iodo-4-quinazolinone (22.0 g, 81%) as a grey crystalline solid. 1H NMR (400 MHz; DMSO-d6) δ: 12.38 (br. s, 1H), 8.35 (d, 1H), 8.05–8.10 (m, 2H), 7.43 (dd, 1H). LRMS: 272.9 (MH+).

6-iodo4-chloroquinazoline (12): To a stirred solution of DMF (6.3 mL) in DCE (20 mL) cooled to 0° C. was added dropwise a solution of oxalyl chloride (60 mL of a 2M solution in DCE). After addition was complete, the cooling bath was removed and 6-iodo-3H-quinazolinone (10 g, 36.8 mmol) was added as a solid. The resulting mixture was heated to reflux under nitrogen for 3 hours. Upon cooling to room temperature, the reaction was quenched cautiously with H$_2$O. CH$_2$Cl$_2$ was added and the bilayer transferred to a separatory funnel. The aqueous layer was extracted with CH$_2$Cl$_2$ (2×50 mL) and the combined organic layers dried (Na$_2$SO$_4$). The solvent was removed in vacuo to provide a yellow solid which was triturated with diethyl ether to remove any remaining impurities. The resulting yellow solid obtained by filtration was shown to be pure by NMR. $^1$HNMR (CDCl$_3$, 400 MHz): δ: 9.05 (s, 1H), 8.65 (d, 1H), 8.21 (dd, 1H), 7.78 (d, 1H).

6-iodo-4-phenoxyyuinazoline (13): A suspension of NaH (washed free of mineral oil) in DMF (40 mL) was cooled to 0° C. and a solution of phenol (5.65 g, 60 mmol) in DMF (20 mL) was added dropwise. Upon completion of addition, 6-iodo-4chloroquinazoline (14.6 g, 50.3 mmol) was added as a solid in small portions. The cooling bath was moved and the reaction mixture was stirred at room temperature for 2 hours. The mixture was then quenched with water (200 mL), diluted with EtOAc (300 mL) and transferred to a separatory funnel. The organic layer was washed with dilute aqueous NaOH, water and brine and dried over $Na_2SO_4$. Filtration of the solids and removal of the solvent provided quinazoline 13 (17.2 g, 98%) as a yellow solid. $^1$H NMR (400 MHz; $CDCl_3$) δ: 8.74 (d, 1H), 8.14 (s, 1H), 8.12 (dd, 1H), 7.71 (d, 1H), 7.49 (dd, 2H), 7.32 (t, 1H), 7.22 (m, 2H).

Method A: (1-Benzenesulfonyl-1H-indol-5-yl)-[6-(3-imidazol-1-yl-prop-1-ynyl)-quinazolin-4-yn]-amine (15)..

(1-Benzenesulfonyl-1H-indol-5-yl)-(6-iodo-quinazolin-4-yl)-amine (14): 6-iodo-4-chloroquinazoline (2.38 g, 8.20 mmol) and 5-amino-1-benzenesulfonylindole (2.46 g, 9.00 mmol) were combined in DCE (20 mL) and t-butanol (20 mL). The resulting mixture was heated at reflux under nitrogen for 18 hours to form a bright yellow suspension. Upon cooling the solids were filtered and rinsed with $CH_2Cl_2$ and placed under high vacuum to remove any excess solvent. Quinazoline 14 (3.23 g, 75%) was obtained as a yellow solid. $^1$H NMR (DMSO d6; 400 MHz): δ: 9.24 (s, 1H, NH), 8.84 (s, 1H), 8.33 (dd, 1H, 8.9 Hz, 1.7 Hz), 8.01 (m, 4H), 7.90 (m, 2H), 7.70 (m, 2H), 7.60 (m, 3H), 6.92 (dd, 1H, J=3.7 Hz, 0.6 Hz).

(1-Benzenesulfonyl-1H-indolyl)-5-yl)-[6-(3-imidazol-1-yl-prop-1-ynyl)-quinazolin-4-yl]-amine. (15): Quinazoline 14 (150 mg, 0.28 mmol), 1-N-2-propynylimidazole (200 mg, 1.89 mmol), $Pd(OAc)_2$ (4 mg, 0.016 mmol) and $PPh_3$ (9 mg, 0.033 mmol) were mixed in $NEt_3$ (1.25 mL) and DMF (0.5 mL). The mixture was heated at 80° C. under $N_2$ for 16 hours. Upon cooling the black suspension was concentrated under reduced pressure and the residue dissolved in MeOH. Silica gel (1 g) was added and the methanol removed in vacuo. The resulting silica gel was placed atop a silica gel (40 g) column which was then eluted with 200 mL 50:1 $CH_2Cl_2$:MeOH, the 300 mL 25:1 $CH_2Cl_2$ to provide alkyne 15 (72 mg, 51%) as a yellow foam. $^1$H NMR ($CDCl_3$; 400 MHz): δ: 8.95 (br, 1H, NH), 8.63 (s, 1H), 8.62 (s, 1H), 8.24 (s, 1H), 7.96 (d, 1H, J=1.7 Hz), 7.84 (m, 3H), 7.71 (m, 2H), 7.51 (m, 3H), 7.41 (m, 2H), 7.14 (s, 1H), 7.10 (s, 1H), 6.55 (d, 1H, J=3.5 Hz), 5.01 (s, 2H).

Method A': (3-Methyl-4-phenoxy-phenyl)-[6-(3-piperazin-1-yl-prop-1-ynyl)-quinazolin-4-yl]-amine (6-iodo-quinazolin-4-yl)-(3-methyl-4-phenoxy-phenyl)-amine: The 4-chloro-6-iodo-quinazoline (5.0 g, 17.2 mmol) and the 3-methyl-4-phenoxyaniline (17.2 mmol) were mixed together in 1:1 dichloroethane and t-butanol (50 ml). The reaction mixture was heated at 90° C. for 4 hours whereupon a yellow precipitate was observed. The reaction was cooled down and the precipitate was collected and afforded (6-iodoquinazolin-4-yl)-(3-methyl-4-phenoxy-phenyl)-amine. (8.0 g, 94%). M/z, 454. $^1$H NMR ($CD_3OD$): δ: 9.12(s, 1H), 8.83(s, 1H), 8.39(d, 1H, J=8.8 Hz), 7.63(d, 1H, J=8.8 Hz), 7.55 (d, 1H, J=2.1 Hz), 7.35(dd,1H, J1=J2=8.5 Hz), 7.28(t, 2H, J=8.1 Hz,), 7.05 (t, J=8.5 Hz), 6.87(d, 1H, J=8.1 Hz), 3.81(s, 3H).

3-(methyl-4phenoxy-phenyl)-[6-(3-piperazin-1-yl-prop-1-ynyl)quinazolin-4-yl]-amine: The 4-prop-2-ynyl-piperazine-carboxylic acid tert-butyl ester (2.37 g, crude) and (6-iodo-quinazolin-4-yl)-(3-methyl-4-phenoxy-phenyl)-amine (800 mg, 1.76 mmol) , $Pd(OAc)_2$ (23,7 mg, 0.105 mmol,), $PPh_3$(55.3 mg,0.21 mmol) in $Et_3N$ (8 ml) and DMF (3 ml) were mixed together. The resulting reaction mixture was heated at 80° C. for overnight. After cooling, methylene chloride was added to the reaction mixture and the dark mixture was washed with brine and dried over sodium sulfate. The solvent was removed and the residue was chromatographed on silica gel (1:1 hexane+ethyl acetate) to give product 2. 2 was dissolved in methyene chloride and HCl gas was bubbled through for 5 minutes, precipitate was collected and afforded (400 mg , 46.7%) product (3-methyl-4-phenoxy-phenyl)-[6-(3-piperazin-1-yl-prop-1-ynyl)-quinazolin-4-yl]-amine.

M/z, 450, $^1$H NMR (DMSO), δ (ppm), 9.52(s, 1H), 8.84(s, 1H), 8.20(dd, 1H, J1=8.7 Hz, J2=1.3 Hz), 7.99 ( d, 1H, J=2.5 Hz), 7.60(dd, J=8.7 Hz, J2=2.7 Hz), 7.36(app t, 2H, J=8.5 Hz), 7.11(t, 1H, J=7.5 Hz), 6.92(d, 1H, J=8.8 Hz), 6.91(d, 1H, J=7.9 Hz). 3.55 (br, 4H), 3.44(br, 4H), 3.30(s, 2H), 2.19(s, 3H).

Method B: (6-Cyclobutyl-quinazolin-4yl)-(4-phenoxy-phenyl)amine (17).

6-cyclobutyl-4-phenoxyquinazoline (16): To a stirred solution of naphthalene (3.85 g, 30 mmol) in dry THF (tetrahydrofuran)(20 mL) at room temperature was added finely cut lithium metal (0.21 g, 30 mmol) in small portions. The mixture turned dark green and stirring was continued for 2 hours. A solution of $ZnCl_2$ (33 mL of a 0.5M solution in THF, 16.5 mmol) was then added dropwise via syringe imparting a black color. After 3 hours, stirring was discontinued and the fine Zn dust was allowed to settle. The supernatant (~40 mL) was removed with a dry pipet and replaced with fresh THF (10 mL). Cyclobutyl bromide (2.0 g, 14.8 mmol) was then added and the resulting dark mixture allowed to stir at room temparature for 16 hours. Stirring was again stopped and the supernatant organozinc reagent used immediately in the next reaction.

To a solution of 6-iodo4-phenoxyquinazoline (1.75 g, 5.03 mmol), $Pd_2(dba)_3$ [tris(dibenzylideneacetamide) dipalladium(0)] (90 mg, 0.1 mmol) and trifurylphosphine (185 mg, 0.8 mmol) in THF (10 mL) was added cyclobutyl zinc prepared as above. The resulting mixture was stirred for 6 hours, then diluted with THF (30 mL) and quenched with saturated $NH_4Cl$ solution (40 mL). The two layers were separated and the organic layer washed with water and brine then dried ($Na_2SO_4$). Removal of the solids and removal of the solvent in vacuo provided a brown oil. Purification by silica gel chromatography eluting with 1:1 EtOAc:hexanes provided 6-cyclobutyl4-phenoxyquinazoline (0.78 g, 56%) as a yellow oil. $^1$H NMR (400 MHz: $CDCl_3$): δ: 8.71 (s, 1H), 8.14 (s, 1H), 7.92 (d, 1H), 7.78 (dd, 1H), 7.50 (t, 2H), 7.31 (t, 1H), 7.25 (d, 2H), 3.78 (m, 1H), 2.43 (m, 2H), 2.25 (m, 2H), 2.11 (m, 1H), 1.92 (m, 1H).

(6-Cyclobutylquinazolin-4-yl)-(4-phenoxy-phenyl)amino (17): Quinazoline 16 (50 mg, 0.18 mmol) was combined with 4-phenoxyaniline (67 mg, 0.36 mmol) in phenol (0.45 g). The mixture was heated at 100° C. for a total of 17 hours. Excess phenol was removed by distillation under reduced pressure to provide a residue which was triturated with $CH_2Cl_2$ to provide the desired quinazoline 17 (20 mg, 30%) as a yellow solid. $^1$H NMR (DMSO d6, 400 MHz): δ: 9.76 (s, 1H), 8.47 (s, 1H), 8.31 (s, 1H), 7.77 (d, 2H), 7.69 (m, 2H), 7.36 (t, 2H), 7.11 (t, 1H), 7.03 (d, 2H), 6.98 (d, 2H), 3.69 (m, 1H), 2.35 (m, 2H), 2.23 (m, 2H), 2.01 (m, 1H), 1.86 (m, 1H).

Method C: cis- and trans-3-[4-(1-Benzenesulfonyl-1H-indol-5-ylamino)-quinazolin-6-yl]-cyclobutanecarboxylic acid ethyl ecter (19a/19b).

cis- and trans-3-(4-Phenoxy-quinazolin-6-yl)-clobutanecarboxylic acid ethyl ester (18a,b): To a solution of naphthalene (1.92 g, 15 mmol) in dry THF under $N_2$ was added finely cut Li metal (104 mg, 15 mmol) in small portions resulting in a green mixture which was stirred for 2 hours. Zinc Chloride (16 mL of a 0.5M solution in THF, 8 mmol) was then added dropwise via syringe and the mixture stirred at room temperature for 3 hours. Stirring was stopped and the supernatant removed and replaced with a solution of ethyl-3-iodocyclobutane-1-carboxylate (790 mg, 3 mmol). The resulting suspension was stirred for 20 hours when stirring was stopped and the remaining Zn metal allowed to settle. The remaining solution was then transferred to a dry flask containing quinazoline 13 (520 mg, 1.5 mmol), $Pd_2(dba)_3$ (27 mg, 0.03 mmol) and tri-2-furylphosphine (56 mg, 0.24 mmol). The mixture was stirred at room temperature for 16 hours. The mixture was concentrated, and the residue taken up in EtOAc (30 mL) and washed with saturated aqueous $NH_4Cl$, brine and $H_2O$ and dried ($Na_2SO_4$). The solvent was removed in vacuo and the resulting residue purified by silica gel chromatography to provide cyclobutyl esters 18a and 18b as a mixture of cis and trans isomers (300 mg, 57%). LRMS: 349.2 (MH+). HPLC: 7.31 min (28%); 7.44 min (72%).

cis- and trans-3-[4-(1-Benzenesulfonyl-1H-indol-5-ylamino)-quinazolin-6-yl-cyclobutanecarboxylic acid ethyl ester (19a,b): Esters 18a and 18b (300 mg, 0.86 mmol) were combined with 5-amino-1-phenylsulfonylindole (270 mg, 1.0 mmol) and phenol (1.0 g). The mixture was heated to 100° C. for 48 hours. The excess phenol was removed by distillation and the residue dissolved in $CH_2Cl_2$, transferred to a separatory funnel and washed with $H_2O$ and brine. The organic layer was dried ($Na_2SO_4$) and the solvent removed to provide a dark residue which was purified by preparative TLC eluting with EtOAc to provide esters 19a and 19b (0.20 g, 44%) as a waxy solid. LRMS: 527.2 (MH+). HPLC: 7.54 min (16%); 7.64 min (84%).

Method D: cis- and trans-{3-[4(1-Benzenesulfonyl-1H-indol-5-ylamino)-quinazolin-6-yl]-cyclobutyl}-methanol (20a,b):

To a cold (−78° C.), stirred solubon of ethyl esters 19a/19b (70 mg, 0.13 mmol) in anhydrous toluene (5 mL) was added 0.78 mL of DIBAL-H (diisobutylaluminum hydride) (1M in toluene) dropwise via syringe. The reaction was then warmed up to 0° C., stirred for 3 hours, then quenched by dilution with aqueous $NH_4Cl$. The mixture was transferred to a separatory funnel and extracted with ethyl acetate. The organic layer was dried ($Na_2SO_4$), the solids removed and the remaining filtrate concentrated to provide an oil which was purified by preparative TLC (elute wi ethyl acetate) to give 7 mg (11%) of alcohols 20a/20b as a yellow solid: MS m/z (MH+) 485.2; HPLC 5.97 min.

Method E: cis- and trans-{3-[4(1-Benzenesulfonyl-1H-indol-5-ylamino)-quinazolin-6-yn]-cyclobutyl}pyrrolidin-1-yl-methanone (21a. b)

The ethyl esters 19a/19b (60 mg, 0.11 mmol) were dissolved in methanol (5 mL) and refluxed for 1 hour to convert the ethyl ester to methyl ester. After removal of methanol, the residue was dissolved in pyrrolidine (5 mL) and heated at reflux for 20 hours. Removal of pyrrolidine gave a oily, brown product mixture which was purified by preparative TLC (ethyl acetate elution) to give 22 mg (36%) of amides 21a/21b as a waxy, yellow solid: MS m/z (MH+) 552.2; HPLC 6.447 min.

Method F: 4-[4-(1-Benzyl-1H-indol-5-ylamino-quinazolin-6-ylethynyl]-1-methyl-piperidin-4-ol (23).

1-Methyl-4-(4-phenoxy-quinazolin-6-ylethynyl)-piperidin-4-ol (22): To a 100 mL round bottom flask under nitrogen were added, quinazoline 13 (1.32 g, 3.80 mmol), 4-ethynyl-1-methyl-piperidin-4-ol (1.06 g, 7.6 mmol), $Pd(OAc)_2$ (51mg, 0.23 mmol), $PPh_3$ (120 mg, 0.46 mmol) and triethylamine (18 mL). The flask was equipped with a reflux condenser and the mixture heated to 100° C. for 16 hours. The dark solution was then cooled and the triethylamine removed under reduced pressure. The resulting residue was diluted with EtOAc (75 mL) and $H_2O$ (25 mL) and transferred to a separatory funnel. The organic layer was washed successively with $H_2O$ (2×25 mL) and the combined aqueous washes back extracted with EtOAc (25 mL). The combined organic layers were dried ($MgSO_4$) and the solvent removed under reduced pressure. The resulting black foam was purified on silica gel (50 g) eluting with 250 mL 30:1 $CH_2Cl_2$:MeOH, then 400 mL 30:1:1 $CH_2Cl_2$:MeOH:$NEt_3$ to provide the desired product as a yellow foam (930 mg, 68%). $^1$H NMR: (CDCl3; 400 MHz) δ: 8.71 (s, 1H), 8.36 (d, 1H, J=1.9 Hz), 7.89 (d, 1H, J=8.7 Hz), 7.80 (dd, 1H, J=8.7 Hz, 1.9 Hz), 7.45 (t, 2H, J=8.3 Hz), 7.31 (m, 1H), 7.21 (m, 2H), 2.72 (br, 2H), 2.47 (br, 2H), 2.31 (s, 3H), 2.09 (m, 2H), 2.00 (m, 2H).

4-[4-(1-Benzyl-1H-indol-5-ylamino-quinazolin-6-ylethynyl]-1-methyl-piperidin-4-ol (23): In a 1 mL Wheaton vial quinazoline 22 (80 mg, 0.22 mmol) was combined with 5-amino-1-benzylindole (54 mg, 0.24 mmol), pyridinium hydrochloride (5 mg, 0.04 mmol) and phenol (104 mg, 1.11 mmol). The vial was capped and heated at 100° C. for 16 hours. After cooling the contents of the Wheaton vial were solvated in a minimal amount of EtOAc and placed atop a silica gel (5 g) column. Elution of the column with 1:1:0.1Hexanes:EtOAc/$NEt_3$ removed high $R_f$ impurities. The desired product 23 ($R_f$ 0.05, 10:1 $CH_2Cl_2$:MeOH) was eluted off with 10:1 $CH_2Cl_2$:MeOH and gave a yellow solid (65 mg, 60%). 1H NMR (DMSO d6; 400 MHz): δ: 9.88 (s, 1H, NH), 8.67 (s, 1H), 8.45 (s, 1H), 7.92 (d, 1.7 Hz), 7.76 (d, 1H, J=8.5 Hz), 7.67 (d, 11H, J=8.5 Hz), 7.50 (d, 1H, J=3.1 Hz), 7.42 (d, 1H, J=8.9 Hz), 7.35 (dd, 1H, J=8.9 Hz, 1.9 Hz), 7.31–7.18 (m, 6H), 6.48 (dd, 1H, J+3.1 Hz, 0.8 Hz), 5.41 (s, 2H), 2.97 (br, 2H), 2.67 (br, 2H), 2.47 (s, 3H), 1.92 (br, 2H), 1.82 (br, 2H). LRMS: 488.2 (MH+), 126.1.

Method G: Acetic acid 3-[4-(1-benzonesulfonyl-1H-indol-5-ylamino)-quinazoin-6-yl]-allyl ester (27)

3-(4-Phenoxquinazolin-6-yl)acryllc acid methyl ester (24): A pressure bottle was charged with quinazoline 13 (3.5 g, 10.0 mmol), methyl acrylate (6.0 g, 70.0 mmol), $Pd(OAc)_2$ (140 mg, 0.62 mmol), $PPh_3$ (320 mg, 1.22 mmol), DMF (4mL) and $NEt_3$ (15 mL). The tube was purged with nitrogen, sealed and heated at 110° C. with stirring for 3 hours. The mixture was cooled and diluted with EtOAc and transferred to a separatory funnel then washed with $H_2O$ and brine and dried ($MgSO_4$). After filtration the filtrate was concentrated under reduced pressure to provide a yellow solid which was recrystallized (EtOAc) to yield ester 24 as a pale yellow solid (2.2 g, 72%). $^1$HNMR (CDCl$_3$: 400 MHz): δ 8.76 (s, 1H), 8.47 (s, 1H), 8.08 (d, 1H), 8.06 (d, 1H), 7.87 (dd, J=16 Hz, 1 Hz), 7.48 (t, 2H), 7.35 (t, 1H), 7.25 (m, 2H), 6.60 (d, J=16 Hz, 1 Hz), 3.83 (s, 3H).

3-(4-Phenoxy-quinazolin-6-yl)-prop-2-en-1-ol (25): To a solution of ester 24 (1.35 g, 4.41 mmol) in toluene (60 mL) under $N_2$ at −78° C. was added DIBAL-H (8.8 mL of a 1M solution in toluene, 8.8 mmol) dropwise. The reaction was then warmed to 0° C. and stirred for 30 minutes, then quenched with 30 mL of saturated Rochelle's salt and the mixture stirred overnight. The bilayer was transferred to a separatory funnel and the organic layer washed with $H_2O$ and brine and dried ($MgSO_4$). After filtration the organic layer was concentrated under reduced pressure to provide a yellow oil which was purified by silica gel chromatography eluting with 1:1 hexanes:EtOAc, then EtOAc. The allylic alcohol 25 (900 mg, 73%) was isolated as a pale yellow oil. $^1$H NMR (CDCl$_3$; 400 MHz): δ: 8.72 (s, 1H), 8.27 (s, 1H), 7.66 (m, 2H), 7.62 (m, 1H), 7.47 (m, 3H), 7.34 (m, 1H), 7.24 (m, 2H), 6.82 (dd, 1h), 6.56 (m, 1H), 4.41 (dd, 1H).

Acetic acid 3-(4-phenoxy-quinazolin-6-yl)-allyl ester (26): To alcohol 25 (900 mg, 3.23 mmol) and pyridine (0.8 mL, 10 mmol) in dry CH$_2$Cl$_2$ (15 mL) at 0° C. was added acetyl chloride (0.3 mL, 4.2 mmol). The resulting mixture was stirred for 2 hours, the diluted with CH$_2$Cl$_2$ (10 mL) and 5% HCl (10 mL). The mixture was transferred to a separatory funnel and the organic layer washed with H$_2$O and brine. The organic layer was dried (Na$_2$SO$_4$), solids filtered and the solvent removed in vacuo to provide the desired acetate 26 as a yellow waxy solid (1.04 g, 100%).$^1$H NMR (CDCl$_3$; 400 MHz): δ: 8.72 (s, 1H), 8.30 (d, 1H, J=1.7 Hz), 7.98 (m, 2H), 7.49 (m, 2H), 7.30 (m, 1H), 7.25 (m, 2H), 6.84 (d, 1H, J=16.0 Hz), 6.46 (m, 1H), 4.79 (dd, 2H, J=6.2 Hz, 1.2 Hz), 2.11 (s, 3H).

Acetic acid 3-]4-(1-benzenesulfonyl-1H-indol-5-ylamino)-quinazolin-6yl]-allyl ester (27). A mixture of ester 23 (630 mg, 1.97 mmol) and 5-amino-1-phenylsulfonylindole in phenol (3.0 g) was heated at 100° C. for 20 hours. Excess phenol was removed by distillation and the resulting brown oil was purified by silica gel chromatography eluting with 1:1 ethyl acetate:hexanes then ethyl acetate. Quinazoline 27 (430 mg, 43%) was obtained as an off-white waxy solid. $^1$H NMR (CDCl$_3$; 400 MHz): δ: 8.61 (s, 1H), 7.92 (m, 3H), 7.82 (m, 4H), 7.51 (m, 2H), 7.43 (m, 3H), 6.74 (d, 1H), 6.62 (d, 1H), 6.45 (dt, 1H), 4.74 (dd, 2H), 2.09 (s 3H).

Method G': 3-[4-(1-Benzyl-1H-indazol-5-ylamino)-quinazolin-6-yl]-acrylic acid methyl ester (28) and 3-[4-(4-Phenoxy-phenylamino)-quinazolin-6-yl]-prop-2-en-1-ol (29). An identical procedure to that used to transform intermediate 26 into 27 was used to convert 4-phenoxyquinazoline intermediates 24 and 25 into their respective 4-arylaminoquinazoline derivatives 28 and 29 respectively.

Method H: {6-[3-(6-Amino-3-aza-bicyclo[3.1.0]hex-3-yl)-propenyl-quinazolin-4-yl}-(1-benzenesulfonyl-1H-indol-yl)-ammine (30).

A mixture of palladium acetate (6 mg, 0.027 mmol) and P(C$_6$H$_4$—m—SO$_3$Na)$_3$ (30 mg, 0.053 mmol) in water (0.3 mL) was stirred at room temperature for 1 hour, followed by the addition of allylic acetate 15 (150 mg, 0.30 mmol) and (1a,5a,6a)-6-t-butyloxycarbonylamino-3-azabicyclo[3.1.0] hexane (prepared as in Brighty, et al. Synlett 1996, pp.1097–1099.) (71 mg, 0.36 mmol) in CH$_3$CN (3 mL). The resulting reaction mixture was stirred at 50° C. for 1.5 hours, taken up in ethyl acetate (10 mL), and washed with aqueous NH$_4$Cl and water. The separated organic layer was dried over Na$_2$SO$_4$ and concentrated to provide a brown oil. Purification by preparative TLC (ethyl acetate elution) yielded 31 mg of yellow solid. The BOC-protected product obtained was dissolved in methanol (5 mL)and deprotected by passing HCl gas through the solution with stirring. After concentration and drylng under high vacuum, amine 30 was obtained as its HCl salt (18 mg, 11%): MS m/z (MH$^+$) 537.2; HPLC 4.423 min.

Method I: 4-[4-(4Phenoxy-phenylamino)-quinazolin-6-ylethynyl]-tetrahydro-pyran-4-ol hydrochloride (32).

4-(4-Chloro-quinazolin-6-ylethynyl)-tetrahydro-pyran-4-ol (31). A mixture of 4-ethynyl-4-hydroxytetrahydropyran (70 mg, 0.55 mmol), 4-chloro-6-iodoquinqzoline (145 mg, 0.50 mmol), bis(triphenylphosphine)palladium(II) chloride (24 mg, 7 mol %), copper (I) iodide (6.6 mg, 7 mol %), and diisopropylamine (56 mg, 0.55 mmol) in anhydrous THF (5 mL) was purged with N$_2$ and stirred for 2 hours under N$_2$ atmosphere. After dilution with ethyl acetate (30 mL), the mixture was washed with aqueous NH$_4$Cl, H$_2$O, and brine, dried over Na$_2$SO$_4$, and concentrated to give the product as yellow solid. Crystallization from ethyl acetate/hexane afforded 0.13 g (90%) of a tan solid: $^1$H NMR (CD$_3$OD) δ 1.88 (m, 2H), 2.04 (m, 2H), 3.73 (m, 2H), 3.91 (m, 2H), 8.04 (s, 1H), 8.05 (s, 1H), 8.36 (s, 1H), 9.00 (s, 1H).

4-[4-(4Phenoxy-phenylamino-quinazolin-6-ylethynyl]-tetrahydro-pyran-4-ol hydrochloride (32). A mixture of 4-(4-Chloro-quinazolin-6-ylethynyl)-tetrahydro-pyran-4-ol (43 mg, 0.15 mmoi) and 4-phenoxyaniline (28 mg, 0.15 mmol) in 2 mL of t-BuOH/1,2-dichloroethane (1:1) was heated at 90° C. with stirring in a reaction vial for 1 hour, The reaction was cooled, diluted with CH$_2$Cl$_2$ and the product was collected by filtration to provide 52 mg (73%) of 32 as a yellow solid: $^1$H NMR (CD$_3$OD) δ 1.86 (m, 2H), 2.02 (m, 2H), 3.74 (m, 2H), 3.92 (m, 2H), 7.05 (m, 4H), 7.15 (t, J=7.6 Hz, 1H), 7.38 (t, J=7.6 Hz, 2H), 7.69 (d. J=6.8 Hz, 2H), 7.81 (d, J=7.2 Hz, 1H), 8.07 (d, J=7.2 Hz, 1H), 8.75 (s, 2H); HPLC: 6.36 min.

Method J: (3-Methoxy-4-phenoxy-phenyl)-(6-piperidin-4-ylethynyl-quinazolin-4-yl)-amine 4-(4-Chloro-quinazolin-6-ylethynyl)-piperidine-1-carboxylic acid tert-butyl ester: A mixture of 4-ethynyl-piperidine-1-carboxylic acid tert-butyl ester (1.12 g, 5.35 mmol), 4-chloro-6-iodoquinazoline (1.35 g, 4.65 mmol), dichlorobis(triphenylphosphine) palladium(II) (0.16 g, 0.23 mmol), copper(I) iodide (0.044 g, 0.23 mmol), and diisopropylamine (0.47 g, 4.65 mmol) in anhydrous THF (20 mL) was stirred at room temperature under nitrogen for 2 hours. After concentration, the residue was dissolved in CH$_2$Cl$_2$ (100 mL), washed with aqueous NH$_4$Cl and brine, dried over sodium sulfate, and concentrated to give the crude product as brown oil. Purification by silica gel column using 20% EtOAc in hexane afforded 1.63 g (94%) of sticky, yellow oil: $^1$H NMR (CDCl$_3$) δ 1.45 (s, 9H), 1.67–1.75 (m, 2H), 1.87–1.92 (m, 2H), 2.84 (m, 1H), 3.20–3.26 (m, 2H), 3.78 (br d, 2H), 7.88 (dd, 1H), 7.97 (d, 1H), 8.26 (d, 1H), 9.00 (s, 1H).

(3-Methoxy-4-phenoxy-phenyl)-(6-piperidin-4-ylethynyl-quinazolin-4-yl)-amine A solution of 4-(4-chloro-quinazolin-6-ylethynyl)-piperidine-1-carboxylic acid tert-butyl ester (131 mg, 0.304 mmol) and 3-methoxy-4-phenoxyaniline hydrochloride (77 mg, 0.306 mmol) in $^t$BuOH/ClCH$_2$CH$_2$Cl (1.0/1.0 mL) was heated in a tightly capped reaction vial at 90 ° C. for 30 minutes. After cooling, the yellow mixture was diluted with MeOH and HCl gas was passed through the mixture for 10 minutes. After stirring for 2 hours, EtOAc was added to precipitate more solid which was collected by suction filtration, rinsed with EtOAc, and further dried to give 105 mg (66%) of yellow solid: $^1$H NMR (CD$_3$OD) δ 1.93–2.02 (m, 2H), 2.18–2.24 (m, 2H), 3.12–3.21 (m, 2H), 3.41–3.47 (m, 2H), 3.81 (s, 3H), 6.87 (d, 2H), 7.02 (t, 1H), 7.06 (d, 1H), 7.27 (t, 2H), 7.33 (dd, 1H), 7.56 (d, 1H), 7.80 (d, 1H), 8.06 (d, 1H), 8.79 (s, 1H), 8.83 (s, 1H); MS m/z (MH$^+$) 451.3.

Method K: (3-Methyl-4-phenoxy-phenyl)-[6-(1-propyl-piperidin-3-ylethynyl)-quinazolin-4-yl]-amine (3-Methyl-4-phenoxy-phenyl)-[6-(1-propyl-piperidin-3-ylethynyl)-quinazolin-4-yl]-amine: (3-Methyl-4-phenoxy-phenyl)-(6-piperidin-3-ylethynyl-quinazolin-4-yl)-amine (114 mg, 0.2 mmol) and propionaldehyde (116 mg, 2.0 mmol) were dissolved in MeOH/H$_2$O (5/0.5 mL) and the pH was adjusted to 5 with AcOH. The reaction was stirred at room temperature overnight and followed by the addition of NaBH$_3$CN (13 mg, 0.2 mmol) over a period of 1 hour. After stirring for another hour, the reaction was concentrated and the residue was partitioned between CH$_2$Cl$_2$ (30 mL) and saturated Na$_2$CO$_3$ (20 mL). The separated organic layer was dried over sodium sulfate and concentrated. Purification by preparative TLC using 10% MeOH in EtOAc gave the free base product which was converted to HCl salt to yield 42 mg (38%) of yellow solid: $^1$H NMR (CD$_3$OD) δ 1.03 (t, 3H), 1.78–1.87 (m, 4H), 2.01–2.08 (m, 2H), 2.28 (s, 3H), 2.96 (t, 1H), 3.07–3.19 (m, 3H), 3.31 (br, 1H), 3.59 (d, 1H), 3.80 (d, 1H), 6.94 (m, 3H), 7.09 (t, 1H), 7.34 (t, 2H), 7.53 (d, 1H), 7.63 (s, 1H), 7.80 (d, 1H), 8.05 (dd, 1H), 8.73 (s, 1H), 8.75 (s, 1H); MS m/z (MH$^+$) 477.1.

Method K': {6-[1-(2-Amino-ethyl)-piperidin-3-ylethynyl]-quinazolin-4-yl}-3-methyl4-phenoxy-phenyl)-amine {6-[1-(2-Amino-ethyl)-piperidin-3-ylethynyl]-quinazolin-4-yl}-(3-methyl-4-phenoxy-phenyl)-amine: (3-Methyl-4-phenoxy-phenyl)-(6-piperidin-3-ylethynyl-quinazolin-4-yl)-amine (114 mg, 0.2 mmol) and tert-butyl N-(2-oxoethyl)carbamate (320 mg, 2.0 mmol) were dissolved in MeOH/H$_2$O (5/0.5 mL) and the pH was adjusted to 5 with AcOH. The reaction was stirred at room temperature overnight and followed by the addition of NaBH$_3$CN (13 mg, 0.2 mmol) over a period of 1 hour. After stirring for another hour, the reaction was concentrated and the residue was partitioned between CH$_2$Cl$_2$ (30 mL) and saturated Na$_2$CO$_3$ (20 mL). The separated organic layer was dried over sodium sulfate and concentrated. Purification by silica gel column using 5% MeOH in EtOAc gave the free base which was dissolved in MeOH. HCl gas was passed through the solution for 5 min and the deprotected product precipitated as HCl salt The mixture was diluted with EtOAc and the solid was collected by suction filtraton, rinsed with EtOAc, and further dried to afford 83 mg (71%) of yellow solid: $^1$H NMR (CD$_3$OD) δ 1.71–1.82 (br, 2H), 2.0–2.12 (br, 2H), 2.27 (s, 3H), 3.00 (t, 1H), 3.03–3.19 (br, 2H), 3.40 (br, 1H), 3.50 (s, 2H), 3.62 (br d, 1H), 3.70 (m, 1H), 3.89 (br d, 1H), 6.93 (m, 3H), 7.08 (t, 1H), 7.33 (t, 2H), 7.52 (d, 1H), 7.64 (s, 1H), 7.79 (d, 1H), 8.05 (d, 1H), 8.75 (s, 1H), 8.77 (s, 1H); MS m/z (MH$^+$) 476.1.

Method L: 3-{2-[4-(3-Methyl-4-phenoxy-phenylamino)-quinazolin-6-yl]-ethyl}-piperidin-3-ol:

3-{2-[4-(3-Methyl-4-phenoxy-phenylamino)-quinazolin-6-yl]-ethyl)-piperidin-3-ol: A mixture of 3-[4-(3-Methyl-4-phenoxy-phenylamino)-quinazolin-6-ylethynyl]-piperidin-3-ol dihydrochloride (100 mg, 0.19 mmol) and Pd/C (10%, 6 mg) was shaken in a Parr bottle with hydrogen at 50 psi overnight and filtered through a pad of Celite. The filtrate was concentrated to small volume and added dropwise into EtOAc with stirring. The solid was collected by suction filtration, rinsed with EtOAc, and further dried to yield 89 mg (89%) of yellow solid: $^1$H NMR (CO$_3$00) 5 1.69 (dt, 1H), 1.81(br d, 1H), 1.95 (t, 3H), 2.15 (m, 1H), 2.28 (t, 3H), 2.93 (t, 1H), 3.02 (m, 3H), 3.18 (d, 1H), 3.31(br, 1H), 6.94 (m, 3H), 7.08 (t, 1H), 7.34 (t, 2H), 7.55 (d, 1H), 7.66 (d, 1H), 7.78 (d, 1H), 8.02 (d, 1H), 8.58 (s, 1H), 8.73 (s, 1H); MS m/z (MH+) 455.2.

Method M: N-{3-[4-(3-Methyl-4-phenoxy-phenylamino)-quinazolin-6-yl]-prop-2-ynyl}-2-morpholin-4-yl-acetam 2-Chloro-N-[3-(4chloro-quinazolin-6-yl)-prop-2-ynyl]-acetamide: 2-Chloro-N-prop-2-ynyl-acetamide (385 mg; 2.93 mmol) and 4-chloro-6-iodoquinazoline (850 mg; 1 equiv.) were dissolved in dry THF and diisopropylamine (296 mg; 0.41 ml; 1 equiv.). To this mixture was added 0.04 equivalents of copper iodide (22 mg) and Pd(PPh$_3$)$_2$Cl$_2$ (82 mg). The reaction was stirred at room temperature under a nitrogen atmosphere overnight (~20 hrs). The solvent was then removed in vacuo and the residue dissolved in CH$_2$Cl$_2$. This solution was transferred to a separatory funnel and washed with 1× saturated NH$_4$Cl, brine, dried over Na$_2$SO$_4$ and the solvent removed in vacuo. The product was purified by silica gel chromatography eluting with 1:1 hexlEtOAc and collecting fractions with an Rf=0.25. This yielded the 2-Chloro-N-[3-(4-chloro-quinazolin-6-yl)-prop-2-ynyl]-acetamide as an off white solid (454 mg; 53%). $^1$H NMR (400 MHz; CDCl$_3$) δ 4.12 (2H, s), 4.40 (2H, d, J=5.2 Hz), 7.91–7.93 (1H, dd, J=2, 6.8 Hz), 8.00 (1H, d, J=8.4 Hz), 8.34 (1H, d, J=1.8 Hz), 9.03 (1H, s). Irms (M+): 294.0, 296.0, 298.1.

2-Chloro-N-{3-[4-(3-methyl-4-phenoxy-phenylamino)-quinazolin-yl]-prop-2-ynyl}-acetamide: A solution of 2Chloro-N-[3-(4-chloro-quinazolin-6-yl)-prop-2-ynyl]-acetamide (50 mg; 0.17 mmol) and 3-methyl-4-phenoxyaniline (36 mg; 0.9 equiv.) in 1,2-dichloroethane (1 ml) and t-butanol (1 ml) was heated at 87° C. for 30 minutes. The mixture was then cooled to room temperature and diluted with ethyl acetate to further facilitate precipitation. The solution was then filtered to give the coupled product as a yellow powder (73 mg; 90%). 2.28 (3H, s), 4.10 (2H, s), 4.30 (2H, s), 6.93 (3H, d), 7.09 (1H, t), 7.34 (2H, t), 7.50–7.53 (1H, dd, J=2.6, 6 Hz), 7.63 (1H, d, J=2.4 Hz), 7.78 (1H, d, J=8 Hz), 8.06–8.08 (1H, dd, J=1.4, 7.2 Hz), 8.68 (1H, d, J=1.2 Hz), 8.75 (1H, s). lrms(M+): 457.0, 4.59.1; (M−): 455.7, 419.6

N-{3-[4-(3-Methyl-4-phenoxy-phenylamino)-quinazolin-6-yl]-prop-2-ynyl}-2-morpholin-4-yl-acetamide: To a solution of 2-Chloro-N-{3-[4-(3-methyl-4-phenoxy-phenylamino)-quinazolin-6-yl]-prop-2-ynyl}-acetamide (63 mg; 0.12 mmol) in toluene (10 ml) was added 3 equivalents of morpholine (31 mg) and the mixture heated at reflux overnight. The reaction was cooled to room temperature and the morpholine salts were filtered out and the solvent removed from the filtrate. The residue was redissolved in CH$_2$Cl$_2$ with a small amount of methanol and HCl gas was bubbled through the solution for 2–3 minutes, The solution was then concentrated to 2–3 ml, diluted with ethyl acetate and filtered to obtain N-{3-[4-(3-Methyl-4-phenoxy-phenylamino)-quinazolin-6-yl]-prop-2-ynyl}-2-morpholin-4-yl-acetamide as a yellow/brown solid (65 mg; 94%). $^1$H NMR (400 MHz; CD$_3$OD) δ 2.27 (3H, s), 3.21 (2H, m), 3.56 (2H, m), 3.87 (2H, m), 4.04 (2H, m), 4.09 (2H, s), 4.36 (2H, s), 6.93 (3H, d, J=8.4), 7.09 (1H, t, J=7.4 Hz), 7.34 (2H, t, J=8 Hz), 7.54 (1H, dd), 7.65 (1H, s), 7.82 (1H, d, J=8.8 Hz), 8.06 (1H, d, J=8.4 Hz), 8.76 (1H, s), 8.80 (1H, s). Irms(M+): 508.0; (M−): 506.0.

Method N: (3-Methyl-4-phenoxy-phenyl)-(6-piperidin-4-ylethynyl-pyridor[3,4-d]pyrimidin-4-yl)-amine 4,6-Dichloro-pyrido[3,4-d]pyrimidine: DMF (0.1 ml) was added to 6chloro-3H-pyrido[3,4-d]pyrimidin-4-one (1.82 g, 10 mmol) followed by dropwise addition of thionyl chloride (10 ml). The flask was fitted with a condenser and a drylng tube and the contents heated to reflux for ~20 minutes whereupon the solids dissolved. The heating was continued for a further 1 h and then cooled. Toluene was added to wash the sides of the flask and the solvents were evaporated in vacuo. Azeotroping with toluene was repeated twice and the crude so obtained was taken through to the next step.

(6-Chloro-pyrido[3,4-d]pyrimidin-4-yl)-(3-methyl-4-phenoxy-phenyl)-amine: The 4,6-dichloro-pyrido[3,4-d]pyrimidine obtained from the previous reaction was taken up in dioxane (50 ml), the 3-methyl 4-phenoxy aniline hydrochloride (2.8 g, 12 mmol) was added and the contents heated to an external bath temperature of -80 oC for 3 hours, whereupon yellow precipitation occurred. Further dioxane (20 ml) was added and the contents heated at ~75° C. for 12 hours. The solution was then filtered and the yellow solid placed under vacuum to provide the desired (6-chloro-pyrido[3,4-d]pyrimidin-4-yl)-(3-methyl-4-phenoxy-phenyl)-amine hydrochloride (3.6 g, ~100%). $^1$H NMR (CD$_3$OD; 400 MHz) δ 9.05 (s, 1H), 8.87 (s, 1H), 8.64 (s, 1H), 7.69 (d, J=2.5 Hz, 1H), 7.58 (dd, J=8.7, 2.5 Hz, 1H),7.35 (dd, J=8.7, 7.5 Hz, 2H), 7.10 (t, J=7.2 Hz, 1H), 6.94 (d, J=8.7 Hz, 3H), 2.29 (s, 3H). MS m/z (MH+): 363.2

(3-Methyl-4-phenoxy-phenyl)-(6-piperidin-4-ylethynyl-pyrido[3,4-d]pyrimidin-4-yl)-amine: A flame dried pear shaped flask was charged with the (6-chloro-pyrido[3,4-d]pyrimidin-4-yl)-(3-methyl-4-phenoxy-phenyl)-amine hydrochloride (200 mg, 0.5 mmol), the 4-ethynyl-piperidine-1-carboxylic acid tert-butyl ester (314 mg, 1.5 mmol), Pd(PhCN)$_2$Cl$_2$ (19 mg, 0.05 mmol), 1,4-bis(diphenylphosphino)butane (32 mg, 0.075 mmol) and CuI (4.8 mg, 0.025 mmol). Dioxane (5 ml) was added and to this stirred suspension under Ar was added diisopropylamine (0.32 ml, 2.28 mmol) whereupon a lot of the solid dissolved. The flask (fitted with a condenser) was then placed in a preheated oil-bath and heated at a bath temperature of 104° C. for 14 hours at which point LC/MS indicated disappearance of starting material. The reaction mixture was then filtered through a plug of silica, concentrated and chromatographed using a gradient elution of 20–80% EtOAc-hexanes to give the desired coupled product as a solid (165 mg, 62%). The solid was taken up in CH$_2$Cl$_2$ (and sparing amounts of MeOH to help in dissolution), HCl (g) was bubbled through, followed by addtition of ether whereupon solid precipiated out which was filtered and placed under vacuo to give the desired (3-methyl-4-phenoxy-phenyl)-(6-piperidin-4-ylethynyl-pyrido[3,4-d]pyrmidin-4-yl)-amine as a dihydrochloride salt. $^1$H NMR (CDCl$_3$; 400 MHz) δ 9.12 (s, 1H), 8.85(s, 1H), 8.68 (s, 1H), 7.70 (d, J=2.5 Hz, 1H), 7.58 (dd, J=8.7, 2.5 Hz, 1H),7.34 (dd, J=8.3, 7.5 Hz, 2H), 7.10 (app t, J=7.2 Hz, 1H), 6.94 (d, J=8.7 Hz, 3H), 3.42 (m, 2H), 3.19 (m, 3H), 2.29 (s, 3H), 2.22 (m, 2H), 2.0 (m, 2H). MS m/z (MH+): 436.3.

Method O: 4-Aminomethyl-1-[4-(3-methyl-4-phenoxy-phenylamino)-quinazolin-6-yl]-pent-1-yn-3-ol 5-(4-Chloro-quinazolin-ylethynyl)-4,4-dimethyl-oxazolidin-2-one: A mixture of 4,4-Dimethyl-5-ethynyl-2-oxazolidinone (1.10 g, 7.90 mmol), 4chloro-6-iodoquinazoline (1.63 g, 5.60 mmol), dichlorobis(triphenylphosphine)palladium(II) (200 mg, 0.28 mmol), copper iodide (53 mg, 0.28 mmol), and diisopropylamine (0.57 g, 5.60 mmol) in anhydrous THF (30 mL) was stirred at room temperature under nitrogen for 4 hours. After concentration, the residue was dissolved in CH$_2$Cl$_2$ (80 mL), washed with aqueous NH$_4$Cl and brine, dried over sodium sulfate, and concentrated to give the crude product as brown oil. Purification by silica gel column using 50–70% EtOAc in hexane afforded 1.22 g (72%) of yellow solid: $^1$H NMR (CDCl$_3$) δ 1.49 (s, 3H), 1.53 (s, 3H), 5.14 (s, 1H), 5.57 (brs, 1H), 7.95 (dd, 1H), 8.04 (d, 1H, J=8.8 Hz), 8.38 (d, 1H, J=2.0 Hz), 9.05 (s, 1H).

4-Amino-4-methyl-1-[4-(3-methyl-4-phenoxy-phenylamino)-quinazolin-6-yl]-pent-1-yn-3-ol: A solution of 5-(4-Chloro-quinazolin-6-ylethynyl)-4,4-dimethyl-oxazolidin-2-one (151 mg, 0.5 mmol) and 3-methyl-4-phenoxyaniline hydrochloride (130 mg, 0.55 mmol) in $^t$BuOH/ClCH$_2$CH$_2$Cl (1:1, 2.0 mL) was heated in a tightly capped reaction vial at 90 ° C. for 30 minutes. After cooling, the yellow mixture was diluted with EtOAc to precipitate more solid which was collected by suction filtration, rinsed with EtOAc, and further dried to give 215 mg (86%) of yellow solid. This material (215 mg, 0.43 mmol) was immediately combined with KOH (0.51 g, 9.0 mmol) in MeOH/H$_2$O (9/3 mL) and refluxed for 20 hours. After cooling, the reaction was neutralized with 0.60 g (10.0 mmol) of AcOH and concentrated. The residue was suspended in CH$_2$Cl$_2$ and purified on a silica gel column using 20% MeOH in CH$_2$Cl$_2$. The purified free base was converted to HCl salt to afford 46 mg (22%) of yellow solid: $^1$H NMR (CD$_3$OD) δ 1.49 (s, 3H), 1.52 (s, 3H), 2.28 (s, 3H), 4.64 (s, 1H), 6.93 (m, 3H), 7.09 (t, 1H), 7.34 (m, 2H), 7.55 (dd, 1H), 7.65 (d, 1H), 7.83 (d, 1H), 8.13 (dd, 1H), 8.77 (S, 1H), 8.87 (s, 1H); MS m/z (MH+) 439.2.

The following examples were prepared using the methods described above. In the Table below, the term "min" refers to minutes. Example numbers in the following table do not correspond to compound numbers referred to in the preceding experimental section.

TABLE

| Example | Method to Prepare | IUPAC name | LRMS (MH+) | HPLC Retention time (min) |
|---|---|---|---|---|
| 1 | I | 2-Methyl-4-[4-(4-phenoxy-phenylamino)-quinazolin-8-yl]-but-3-yn-2-ol | 396.1 | 6.88 |
| 2 | G' | 3-[4-(4-Phenoxy-phenylamino)-quinazolin-6-yl]-(E)-prop-2-en-1-ol | 370.1 | 6.06 |
| 3 | B | (6-Cyclobutyl-quinazolin-4-yl)-(4-phenoxy-phenyl)-amine | 368.2 | 8.35 |
| 4 | B | (6-Cyclopropyl-quinazolin-4-yl)-(4 phenoxy-phenyl)-amine | 354.2 | 7.62 |
| 5 | I | 1-Methoxy-2-methyl-4[4-(4-phenoxy-phenylamino)-quinazolin-6-yl]-but-3-yn-2-ol | 426.1 | 6.66 |
| 6 | I | 4-[4-(4-Phenoxy-phenylamino)-quinazolin-6-yl]-2-pyridin-4-yl-but-3-yn-2-ol | 459.0 | 6.56 |
| 7 | I | 1-[4-(4-Phenoxy-phenylamino)-quinazolin-6-ylethynyl]-cyctohexanol | 436.1 | 7.80 |
| 8 | G | N-Methyl-3-[4-(4-phenoxy-phenylamino)-quinazolin-6-yl] acrylamide | 397.2 | 5.81 |
| 9 | G' | 3-[4-(4-Benzyl-phenylamino)-quinazolin-6-yl]-(E)-prop-2-en-1-ol | 368.2 | 6.20 |
| 10 | G' | N,N-Diethyl-3-[6-(3-hydroxy-(E)-propenyl)-quinazolin-4-ylaminol]-benzamide | 377.2 | 4.28 |
| 11 | I | 4-[4-(4-Benzyloxy-phenylamino)-quinazolin-6-ylethynyl]-1-methyl-piperidin4-ol | 465.1 | 4.88 |
| 12 | I | 4-[4-(1-Benzenesulfonyl-1H-indol-5-ylamino)-quinazolin-6-ylethynyl]-1-methyl-piperidin-4-ol | 538.2, 445.0 | 4.86 |
| 13 | I | 4-[4-(4-Benzyl-phenylamino)-quinazolin-6-ylethynyl]-1-methyl-piperidin-4-ol | 449.2, 356.2 | 5.11 |
| 14 | I | 1-Methyl-4-[4-(4-phenoxy-phenylamino)-quinazolin-6-ylethynyl]-piperidin-4-ol | 451.2, 143.2 | 4.89 |
| 15 | B | 3-(6-Cyclobutyl-quinazolin-4-ylamino)-N,N-diethyl-benzamide | 375.3 | 6.24 |
| 16 | B | (4-Benzyl-phenyl)-(6-cyctobutyl-quinazolin-4-yl-amine | 366.3 | 8.49 |
| 17 | B | (6-Cyclobutyl-quinazolin-4-yl)-(1H-indol-5-yl-amine | 315.3 | 5.63 |
| 18 | B | (4-Benzyloxy-phenyl)-(6-cyclobutyl-quinazolin-4-yl)-amine | 382.2 | 7.98 |
| 19 | G' | 3-[4-(1H-Indol-5-ylamino)-quinazolin-6-yl]-(E)-prop-2-en-1-ol | 317.3 | 3.66 |
| 20 | G' | 3-[4-(4-Benzyloxy-phenylamino)-quinazolin-6-yl]-(E)-prop-2-en-1-ol | 384.3 | 5.85 |

TABLE-continued

| Example | Method to Prepare | IUPAC name | LRMS (MH+) | HPLC Retention time (min) |
|---|---|---|---|---|
| 21 | I | 4-[4-(4-Phenoxy-phenylamino)-quinazolin-6-ylethynyl]-tetrahydro-pyran-4-ol | 438.1 | 6.34 |
| 22 | I | 4-[4-(1-Benzenesulfonyl-1H-indol-5-ylamino)-quinazolin-6-yl]-2-methyl-but-3-yn-2-ol | 483.2 | 6.55 |
| 23 | I | 4-[4-(1H-Indol-5-ylamino)-quinazolin-6-yl]-2-methyl-but-3-yn-2-ol | 343.2 | 4.61 |
| 24 | I | 4-[4-(4-Benzyl-phenylamino)-quinazolin-6-yl]-2-methyl-but-3-yn-2-ol | 394.2 | 7.06 |
| 25 | C | 3-[4-(4-Phenoxy-phenylamino)-quinazolin-6-yl]-cyclobutanecarboxylic acid ethyl ester | 440.2 | 7.93/7.83 |
| 26 | B | (1-Benzenesulfonyl-1H-indol-5-yl)-(6-cyctobutyl-quinazolin-4-yl)-amine | 455.2 | 7.80 |
| 27 | I | 4-[4-(4-Phenoxy-phenylamino)-quinazolin-6-yl]-2-pyridin-3-yl-but-3-yn-2-ol | 459.2 | 6.64 |
| 28 | I | 4-[4-(1-Benzenesulfonyl-1H-indol-5-ylamino)-quinazolin-6-yl]-2-pyridin-3-yl-but-3-yn-2-ol | 546.2 | 6.27 |
| 29 | G' | 3-[4-(1-Benzenesulfonyl-1H-indol-5-ylamino)-quinazolin-6-yl]-(E)-prop-2-en-1-ol | 457.2 | 5.80 |
| 30 | G' | 3-[4-(1-Benzyl-1H-indol-5-ylamino)-quinazolin-6-yl]-(E)-prop-2-en-1-ol | 407.3 | 5.72 |
| 31 | G' | 3-[4-(1-Benzyl-1H-indazol-5-ylamino)-quinazolin-6-yl]-(E)-prop-2-en-1-ol | 408.2 | 5.15 |
| 32 | I | 4-[4-(1-Benzyl-1H-indol-5-ylamino)-quinazolin-6-ylethynyl]-1-methyl-piperidin-4-ol | 488.2 | 4.84 |
| 33 | I | 4-[4-(4-Benzyl-phenylamino)-quinazolin-6-ylethynyl]-tetrahydro-pyran-4-ol | 525.1 | 6.11 |
| 34 | I | 4-[4-(1-Benzenesulfonyl-1H-indol-5-ylamino)-quinazolin-6-ylethynyl]-tetrahydro-pyran-4-ol | 436.2 | 6.56 |
| 35 | A | (1-Benzenesulfonyl-1H-indol-5-yl)-[6-(3-imidazol-1-yl-prop-1-ynyl)-quinazolin-4-yl]-amine | 505.2 | 5.80 |
| 36 | I | 5-Methoxy-3,5-dimethyl-1-[4-(4-phenoxy-phenylamino)-quinazolin-6-yl]-hex-1-yn-3-ol | 468.3 | 8.01 |
| 37 | I | 1-[4-(4-Benzyl-phenylamino)-quinazolin-6-yl]-5-methoxy-3,5-dimethyl-hex-1-yn-3-ol | 466.3 | 8.21 |
| 38 | I | 1-(4-(1-Benzenesulfonyl-1H-indol-5-ylamino)-quinazolin-6-yl]-5-methoxy-3,5-dimethyl-hex-1-yn-3-ol | 555.2 | 7.55 |
| 39 | I | 4-[4-(4-Benzyl-phenylamino)-quinazolin-6-yl]-2-pyridin-3-yl-but-3-yn-2-ol | 457.4 | 6.79 |
| 40 | I | 4-[4-(4-Benzyl-phenylamino)-quinazolin-6-yl]-2-pyridin-4-yl-but-3-yn-2-ol | 457.3 | 6.71 |
| 41 | A | (1-Benzenesulfonyl-1H-indol-5-yl)-[6-(3-dimethylamino-prop-1-ynyl)-quinazolin-4-yl]-amine | 482.2 | 5.16 |
| 42 | G | Acetic acid 3-[4-(1-benzenesulfonyl-1H-indol-5-ylamino)-quinazolin-6-yl]-(E)-allyl ester | 499.2 | 7.01 |
| 43 | C | 3-[4-(1-Benzenesulfonyl-1H-indol-5-ylamino)-quinazolin-6-yl]-cyclobutanecarboxylic acid ethyl ester | 527.2 | 7.54/7.64 |
| 44 | I | 1-Methyl-4-{4-[1-(propane-2-sulfonyl)-1H-indol-5-ylamino]-quinazolin-6-ylethynyl}-piperidin-4-ol | 504.3 | 4.41 |
| 45 | H | {6-[3-(6-Amino-3-aza-bicyclo[3.1.0]hex-3-yl(1a,5a,6a))-propenyl]-quinazolin-4-yl}-(1-benzenesulfonyl-1H-indol-5-yl)-amine | 537.2 | 4.42 |
| 46 | I | 2-Methyl-4-{4-[1-(propane-2-sulfonyl)-1H-indol-5-ylamino]-quinazolin-6-yl}-but-3-yn-2-ol | 449.2 | 6.11 |
| 47 | I | 4-[4-(4-Benzyloxy-phenylamino)-quinazolin-6-yl]-2-methyl-but-3-yn-2-ol | 410.3 | 6.63 |
| 48 | I | N,N-Diethyl-3-[6-(3-hydroxy-3-methyl-but-1-ynyl)-quinazolin-4-ylamino]-benzamide | 403.3 | 5.06 |
| 49 | I | 4-[4-(1-Benzenesulfonyl-1H-indol-5-ylamino)-quinazolin-6-yl]-2pyridin-4-yl-but-3-yn-2-ol | 546.3 | 6.26 |
| 50 | D | {3-[4-(1-Benzenesulfonyl-1H-indol-5-ylamino)-quinazolin-6-yl]-cyclobutyl}-methanol | 485.2 | 5.97 |
| 51 | A | (1-Benzenesulfonyl-1H-indol-5-yl)-[6-[3-(2-methoxy-ethylamino)-prop-1-ynyl]-quinazolin-4-yl]-amine | 512.2 | 5.11 |
| 52 | A | (1-Benzenesulfonyl-1H-indol-5-yl)-[6-[3-(2-piperidin-1-yl-ethylamino)-prop-1-ynyl]-quinazolin-4-yl]-amine | 563.2 | 5.23 |
| 53 | E | {3-[4-(1-Benzenesulfonyl-1H-indol-5-ylamino)-quinazolin-6-yl]-cyclobutyl}-pyrrolidin-1-yl-methanone | 552.2 | 6.45/6.64 |
| 54 | A | (1-Benzenesulfonyl-1H-indol-5-yl)-[6-(3-morpholin-4-yl-prop-1-ynyl)-quinazolin-4-yl]-amine | 524.2 | 6.45 |
| 55 | A | (1-Benzenesulfonyl-1H-indol-5-yl)-[6-[3-(1,1-dioxo-1&-thiomorpholin-4-yl)-prop-1-ynyl]-quinazolin-4-yl]-amine | 572.2 | 6.36 |
| 56 | A | (1-Benzenesulfonyl-1H-indol-5-yl)-[6-(3-methylamino-prop-1-ynyl)-quinazolin-4-yl]-amine | 468.2 | 4.89 |
| 57 | A | (1-Benzenesulfonyl-1H-indol-5-yl)-[6-[3-(2-morpholin-4-yl-ethylamino)-prop-1-ynyl]-quinazolin-4-yl]-amine | 567.2 | 5.05 |
| 58 | A | (1-Benzenesulfonyl-1H-indol-5-yl)-[6-{3-[4-methyl-piperazin-1-yl)-propylamino]-prop-1-ynyl}-quinazolin 4-yl]-amine | 594.2 | 4.41 |
| 59 | A | (1-Benzenesulfonyl-1H-indol-5-yl)-[6-(3-pyrrolidin-1-yl-prop-1-ynyl)-quinazolin-4-yl]-amine | 508.3 | 5.21 |
| 60 | I | 4-[4-(1-Benzyl-1H-indazol-5-ylamino)-quinazolin-6-ylethynyl]-tetrahydro-pyran-4-ol | 476.2 | 5.55 |
| 61 | I | 4-[4-(1-Benzyl-1H-indol-5-ylamino)-quinazolin-6-ylethynyl]-tetrahydro-pyran-4-ol | 475.2 | 6.16 |
| 62 | I | 4-[4-(1-Cyclopropylmethyl-1H-indol-5-ylamino)-quinazolin-ylethynyl]-tetrahydro-pyran-4-ol | 439.3 | 5.82 |
| 63 | I | 4-[4-(1-Ethanesulfonyl-1H-indol-5-ylamino)-quinazolin-6-ylethynyl]-tetrahydro-pyran-4-ol | 477.2 | 5.34 |
| 64 | I | 4-[4-(1-Methanesulfonyl-1H-indol-5-ylamino)-quinazolin-6-ylethynyl]-tetrahydro-pyran-4-ol | 463.2 | 4.99 |
| 65 | G' | 3-[4-(1-Benzyl-1H-indazol-5-ylamino)-quinazolin-6-yl]-(E)-acrylic acid methyl ester | 436.2 | 6.59 |
| 66 | I | 1-[4-(1-Benzyl-1H-indol-5-ylamino)-quinazolin-6-ylethynyl]-cyclohexanol | 473.3 | 7.51 |
| 67 | I | 1-[4-(1-Benzenesulfonyl-1H-indol-5-ylamino)-quinazolin-6-ylethynyl]-cyclohexanol | 523.3 | 7.37 |
| 68 | I | 4-[4-(1-Benzenesulfonyl-1H-indol-5-ylamino)-quinazolin-6-yl]-1-methoxy-2-methyl-but-3-yn-2-ol | 513.3 | 6.37 |
| 69 | I | 4-[4-(1-Benzyl-1H-indol-5-ylamino)-quinazolin-6-yl]-1-methoxy-2-methyl-but-3-yn-2-ol | 463.3 | 6.43 |

| Example | Method to Prepare | IUPAC name | LRMS (MH+) | HPLC Retention time (min) |
|---|---|---|---|---|
| 70 | I | 4-[4-(1-Benzyl-1H-indol-5-ylamino)-quinazolin-6-yl]-2-pyridin-3-yl-but-3-yn-2-ol | 496.2 | 6.38 |
| 71 | J | 4-[4-(1-Benzenesulfonyl-1H-indol-5-ylamino)-quinazolin-6-ylethynyl]-piperidin-4-ol | 524.2 | 4.78 |
| 72 | J | (1-Benzenesulfonyl-1H-indol-5-yl)-(6-piperidin-4-ylethynyl-quinazolin-4-yl)-amine | 508.1 | 5.67 |
| 73 | J | [6-(4-Amino-tetrahydro-pyran-4-ylethynyl)-quinazolin-4-yl]-(1-benzenesulfonyl-1H-indol-5-yl)-amine | 524.3 | 5.00 |
| 74 | I | 4-[4-(4-Benzyloxy-phenylamino)-quinazolin-6-ylethynyl]-tetrahydro-pyran-4-ol | 452.3 | 6.26 |
| 75 | I | 4-{4-[3-Methyl-4-(pyridin-2-ylmethoxy)-phenylamino]-quinazolin-6-ylethynyl}-tetrahydro-pyran-4-ol | 467.3 | 5.24 |
| 76 | I | 1-Methyl-4-{4-[3-methyl-4-(pyridin-2-ylmethoxy)-phenylamino]-quinazolin-6-ylethynyl}-piperidin-4-ol | 480.3 | 4.07 |
| 77 | J | 3-[4-(1-Benzenesulfonyl-1H-indol-5-ylamino)-quinazolin-6-ylethynyl]-piperidin-3-ol | 524.2 | 5.6 |
| 78 | I | 1-Cyclopropyl-3-{4-[1-(propane-2-sulfonyl)-1H-indol-5-ylamino]-quinazolin-6-yl}-prop-2-yn-1-ol | 461.1 | 6.23 |
| 79 | I | 1-Cyclopropyl-3-[4-(4-phenoxy-phenylamino)-quinazolin-6-yl]-prop-2-yn-1-ol | 408.2 | 7.00 |
| 80 | I | 4-Methyl-1-[4-(4-phenoxy-phenylamino)-quinazolin-6-yl]-pent-1-yn-3-ol | 410.3 | 7.48 |
| 81 | I | 1-[4-(1-Benzenesulfonyl-1H-indol-5-ylamino)-quinazolin-6-yl]4-methyl-pent-1-yn-3-ol | 497.2 | 7.09 |
| 82 | I | 1-[4-(1-Benzyl-1H-indazol-5-ylamino)-quinazolin-6-yl]4-methyl-pent-1-yn-3-ol | 448.3 | 6.58 |
| 83 | I | 4-Methyl-1-{4-[1-(propane-2-sulfonyl)-1H-indol-5-ylamino]-quinazolin-6-yl}-pent-1-yn-3-ol | 463.2 | 6.69 |
| 84 | I | 1-[4-(4-Benzyloxy-phenylamino)-quinazolin-6-yl]4-methyl-pent-1-yn-3-ol | 424.2 | 7.31 |
| 85 | I | 4-[4-(4-Phenoxy-phenylamino)-quinazolin-6-ylethynyl]-piperidin-4-ol | 437.2 | 4.81 |
| 86 | I | 4-{4-[4-(1-Phenyl-ethoxy)-phenylamino]-quinazolin-6-ylethynyl}-tetrahydro-pyran-4-ol | 466.2 | 6.46 |
| 87 | I | 1-[4-(1-Benzyl-1H-indazol-5-ylamino)-quinazolin-6-yl]-4,4-dimethyl-pent-1-yn-3-ol | 462.3 | 7.00 |
| 88 | I | 4,4-Dimethyl-1-[4-(4-phenoxy-phenylamino)-quinazolin-6-yl]-pent-1-yn-3-ol | 424.2 | 7.89 |
| 89 | I | 4,4-Dimethyl-1-(4-[1-(propane-2-sulfonyl)-1H-indol-5-ylamino]-quinazolin-6-yl)-pent-1-yn-3-ol | 477.2 | 7.12 |
| 90 | I | 1-[4-(1-Benzenesulfonyl-1H-indol-5-ylamino)-quinazolin-6-yl]-4,4-dimethyl-pent-1-yn-3-ol | 511.2 | 7.51 |
| 91 | I | 1-[4-(4-Benzyloxy-phenylamino)-quinazolin-6-yl]4,4-dimethyl-pent-1-yn-3-ol | 438.2 | 7.74 |
| 92 | I | 4,4-Dimethyl-1-{4-[4-(1-phenyl-ethoxy)-phenylamino]-quinazolin-6-yl}-pent-1-yn-3-ol | 452.3 | 7.95 |
| 93 | J | 3-[4-(1-Benzyl-1H-indazol-5-ylamino)-quinazolin-6-ylethynyl]-piperidin-3-ol | 475.2 | 4.42 |
| 94 | J | N,N-Diethyl-3-[6-(3-hydroxy-piperidin-3-ylethynyl)-quinazolin-4-ylamino]-benzamide | 444.3 | 3.74 |
| 95 | J | 3-[4-(4-Phenoxy-phenylamino)-quinazolin-6-ylethynyl]-piperidin-3-ol | 437.2 | 4.97 |
| 96 | J | 3-[4-(4-Benzyloxy-phenylamino)-quinazolin-6-ylethynyl]-piperidin-3-ol | 451.3 | 4.94 |
| 97 | J | 3-[4-(3-Chloro-4-phenoxy-phenylamino)-quinazolin-6-ylethynyl]-piperidin-3-ol | 471.2 | 5.38 |
| 98 | J | 3-[4-(4-Benzyl-phenylamino)-quinazolin-6-ylethynyl]-piperidin-3-ol | 435.2 | 5.16 |
| 99 | J | 3-[4-(1H-Indol-5-ylamino)-quinazolin-6-ylethynyl]-piperidin-3-ol | 384.2 | 3.22 |
| 100 | I | 3-[4-(1-Benzenesulfonyl-1H-indol-5-ylamino)-quinazolin-6-yl]-1-cyclobutyl-prop-2-yn-1-ol | 509.1 | 7.21 |
| 101 | I | 1-Cyclobutyl-3-{4-[1-(propane-2-sulfonyl)-1H-indol-5-ylamino]-quinazolin-6-yl}-prop-2-yn-1-ol | 475.2 | 6.81 |
| 102 | I | 3-[4-(3-Chloro4-phenoxy-phenylamino)-quinazolin-6-yl]-1-cyclobutyl-prop-2-yn-1-ol | 456.2 | 8.11 |
| 103 | I | 1-Cyclobutyl-3-(4-(3-methyl-4-phenoxy-phenylamino)-quinazolin-6-yl]-prop-2-yn-1-ol | 436.2 | 7.95 |
| 104 | I | 3-[4-(1-Benzyl-1H-indazol-5-ylamino)-quinazolin-6-yl]-1-cyclobutyl-prop-2-yn-1-ol | 460.2 | 6.69 |
| 105 | I | 1-Cyclobutyl-3-[4-(4-phenoxy-phenylamino)-quinazolin-6-yl]-prop-2-yn-1-ol | 422.2 | 7.59 |
| 106 | J | 3-[4-(3-Methyl-4-phenoxy-phenylamino)-quinazolin-6-yl]-1-pyrrolidin-2-yl-prop-2-yn-1-ol | 451.2 | 5.26 |
| 107 | I | 3-[4-(1-Benzenesulfonyl-1H-indol-5-ylamino)-quinazolin-6-ylethynyl)-1-methyl-piperidin-3-ol | 538.2 | 4.92 |
| 108 | J | 3-[4-(3-Methyl-4-phenoxy-phenylamino)-quinazolin-6-ylethynyl]-pyrrolidin-3-ol | 437.2 | 5.08 |
| 109 | J | 3-[4-(1-Benzyl-1H-indazol-5-ylamino)-quinazolin-6-yl]-1-pyrrolidin-2-yl-prop-2-yn-1-ol | 474.2 | 5.00 |
| 110 | I | 5-[4-(4-Benzyl-phenylamino)-quinazolin-6-ylethynyl]-4,4-dimethyl oxazolidin-2-one | 449.2 | 7.03 |
| 111 | I | 4,4-Dimethyl-5-[4-(3-methyl-4-phenoxy-phenylamino)-quinazolin-6-ylethynyl]-oxazolidin-2-one | 465.2 | 7.17 |
| 112 | I | 5-[4-(3-Chloro-4-phenoxy-phenylamino)-quinazolin-6-ylethynyl]-4,4-dimethyl-oxazolidin-2-one | 485.1 | 7.34 |
| 113 | I | 5-[4-(1-Benzyl-1H-indazol-5-ylamino)-quinazolin-6-ylethynyl]-4,4-dimethyl oxazolidin-2-one | 489.2 | 6.00 |
| 114 | I | 3-[4-(1-Benzyl-1H-indazol-5-ylamino)-quinazolin-6-ylethynyl]-4,4-dimethyl-oxazolidin-2-one | 488.2 | 6.58 |
| 115 | I | 5-[4-(1-Benzenesulfonyl-1H-indol-5-ylamino)-quinazolin-6-ylethynyl]-4,4 dimethyl-oxazolidin-2-one | 538.1 | 6.21 |
| 116 | J | 3-[4-(3-Chloro-4-phenoxy-phenylamino)-quinazolin-6-ylethynyl] pyrrolidin-3-ol | 457.1 | 5.27 |
| 117 | J | 3-[4-(1-Benzyl-1H-indazol-5-ylamino)-quinazolin-6-ylethynyl]-pyrrolidin-3-ol | 461.2 | 4.31 |
| 118 | J | 3-{4-[1-(Propane-2-sulfonyl)-1H-indol-5-ylamino]-quinazolin-6-ylethynyl}-pyrrolidin-3-ol | 476.1 | 4.35 |
| 119 | J | 3-[4-(3-Benzyloxy-phenylamino)-quinazolin-6-ylethynyl]-pyrrolidin-3-ol | 437.2 | 4.85 |

TABLE-continued

| Example | Method to Prepare | IUPAC name | LRMS (MH+) | HPLC Retention time (min) |
|---|---|---|---|---|
| 120 | J | 3-[4-(3-Phenoxy-phenylamino)-quinazolin-6-ylethynyl]-pyrrolidin-3-ol | 423.2 | 4.87 |
| 121 | J | 3-[4-(1-Benzyl-1H-indol-5-ylamino)-quinazolin-6-ylethynyl]-pyrrolidin-3-ol | 460.0 | 4.81 |
| 123 | J | 3-[4-(1-Benzenesulfonyl-1H-indol-5-ylamino)-quinazolin-6-ylethynyl]-pyrrolidin-3-ol | 510.2 | 4.82 |
| 124 | J | 3-[4-(1-Benzyl-1H-indol-5-ylamino)-quinazolin-6-ylethynyl]-piperidin-3-ol | 474.2 | 4.92 |
| 125 | J | 3-{4-[3-Methyl-4-(pyridin-2-ylmethoxy)-phenylamino]-quinazolin-6-ylethynyl}-piperidin-3-ol | 466.2 | 4.14 |
| 126 | J | 3-{4-(1-(Propane-2-sulfonyl)-1H-indol-5-ylamino)-quinazolin-6-ylethynyl}-piperidin-3-ol | 490.1 | 4.46 |
| 127 | J | 3-[4-(4-Phenoxy-phenylamino)-quinazolin-6-yl]-1-pyrrolidin-2-yl-prop-2-yn-1-ol | 437.2 | 5.08 |
| 128 | J | 3-[4-(1-Benzyl-1H-indazol-5-ylamino)-quinazolin-6-yl]-1-pyrrolidin-2-yl-prop-2-yn-1-ol | 475.2 | 4.45 |
| 129 | J | 3-{4-[1-(Propane-2-sulfonyl)-1H-indol-5-ylamino]-quinazolin-6-yl}-1-pyrrolidin-2-yl-prop-2-yn-1-ol | 490.2 | 4.52 |
| 130 | J | 3-(4-4-Benzyloxy-phenylamino)-quinazolin-6-yl]-1-pyrrolidin-2-yl-prop-2-yn-1-ol | 451.2 | 4.99 |
| 131 | J | 3-[4-(1-Benzenesulfonyl-1H-indol-5-ylamino)-quinazolin-6-yl]-1-pyrrolidin-2-yl-prop-2-yn-1-ol | 524.2 | 4.94 |
| 132 | O | 4-Amino-1-[4-(3-chloro-4-phenoxy-phenylamino)-quinazolin-6-yl]-4-methyl-pent-1-yn-3-ol | 459.1 | 5.41 |
| 133 | J | 3-(4-(4-Fluoro-4-phenoxy-phenylamino)-quinazolin-6-ylethynyl]-piperidin-3-ol | 455.2 | 5.19 |
| 134 | J | 3-[4-(4-Phenoxy-3-trifluoromethyl-phenylamino)-quinazolin-6-ylethynyl]-piperidin-3-ol | 505.1 | 5.61 |
| 135 | J | 4-Amino-1-[4-(1-benzenesulfonyl-1H-indol-5-ylamino)-quinazolin-6-yl]-pent-1-yn-3-ol | 498.1 | 4.82 |
| 136 | J | 3-{4-[4-(3-Methoxy-phenoxy)-3-methyl-phenylamino]-quinazolin-6-ylethynyl}-piperidin-3-ol | 481.2 | 5.15 |
| 137 | J | 3-[4-(3-Methyl-4-m-tolyloxy-phenylamino)-quinazolin-6-ylethynyl]-piperidin-3-ol | 465.1 | 5.56 |
| 138 | J | 3-{4-[4-(2-Methoxy-phenoxy)-3-methyl-phenylamino]-quinazolin-6-ylethynyl}-piperidin-3-ol | 481.1 | 4.94 |
| 139 | J | 3-[4-(3-Methyl-4-o-tolyloxy-phenylamino)-quinazolin-6-ylethynyl]-piperidin-3-ol | 465.2 | 5.50 |
| 140 | L | 3-{2-[4-(3-Methyl-4-phenoxy-phenylamino)-quinazolin-6-yl]-ethyl}-piperidin-3-ol | 455.2 | 4.93 |
| 141 | J | 3-{4-[3-Chloro-4-(pyridin-2-ylmethoxy)-phenylamino]-quinazolin-6-ylethynyl}-piperidin-3-ol | 486.0 | 4.38 |
| 142 | J | 3-[4-(5-Methyl-6-phenoxy-pyridin-3-ylamino)-quinazolin-6-ylethynyl]-piperidin-3-ol | 452.0 | 4.70 |
| 143 | L | 3-{2-[4-(4-Benzyl-phenylamino)-quinazolin-6-yl]-ethyl}-piperidin-3-ol | 439.2 | 4.81 |
| 144 | I | 5-[4-(3-Methoxy-4-phenoxy-phenylamino)-quinazolin-6-ylethynyl]-4,4-dimethyl-oxazolidin-2-one | 481.2 | 6.64 |
| 145 | I | 1-Methyl-3-[4-(3-methyl-4-phenoxy-phenylamino)-quinazolin-6-ylethynyl]-piperidin-3-ol | 465.2 | 5.34 |
| 146 | L | 3-{2-[4-(1H-Indol-5-ylamino)-quinazolin-6-yl]-ethyl}-piperidin-3-ol | 388.3 | 2.86 |
| 147 | I | 3-[4-(3-Methoxy-4-phenoxy-phenylamino)-quinazolin-6-ylethynyl]-1-methyl-piperidin-3-ol | 481.1 | 4.96 |
| 148 | I | 3-(4-(3-Chloro-4-phenoxy-phenylamino)-quinazolin-6-ylethynyl]-1-methyl-piperidin-3-ol | 485.1 | 5.48 |
| 149 | J | Endo-α-3-[4-(3-Chloro-4-phenoxy phenylamino)-quinazolin-6-ylethynyl]-8-aza-bicyclo[3.2.1]octan-3-ol | 497.1 | 5.47 |
| 150 | J | Endo-α-3-[4-(3-Methoxy-4-phenoxy-phenylamino)-quinazolin-6-ylethynyl]-8-aza-bicyclo[3.2.1]octan-3-ol | 493.2 | 4.95 |
| 151 | J | Endo-α-3-(4-(3-Methyl-4-phenoxy-phenylamino)-quinazolin-6-ylethynyl]-8-aza-bicyclo[3.2.1]octan-3-ol | 477.2 | 5.29 |
| 152 | J | Exo-β-3-[4-(3-Chloro-4-phenoxy-phenylamino)-quinazolin-6-ylethynyl]-8-aza-bicyclo[3.2.1]octan-3-ol | 497.1 | 5.35 |
| 153 | J | Exo-β-3-[4-(3-Methoxy-4-phenoxy-phenylamino)-quinazolin-6-ylethynyl]-8-aza-bicyclo[3.2.1]octan-3-ol | 493.2 | 4.86 |
| 154 | J | Exo-β-3-(4-(3-Methyl-4-phenoxy-phenylamino)-quinazolin-6-ylethynyl]-8-aza-bicyclo[3.2.1]octan-3-ol | 477.2 | 5.21 |
| 155 | J | Exo-β-3-[4-(4-Phenoxy-phenylamino)-quinazolin-6-ylethynyl]-8-aza-bicyclo[3.2.1]octan-3-ol | 463.2 | 4.96 |
| 156 | J | (−)-3-[4-(3-Methyl-4-phenoxy-phenylamino)-quinazolin-6-ylethynyl]-piperidin-3-ol | 451.2 | 5.22 |
| 157 | J | (+)-3-(4-(3-Methyl-4-phenoxy-phenylamino)quinazolin-6-ylethynyl]-piperidin-3-ol | 451.2 | 5.22 |
| 158 | J | Endo-α-3-[4-(4-Phenoxy-phenylamino)-quinazolin-6-ylethynyl]-8-aza-bicyclo[3.2.1]octan-3-ol | 463.2 | 5.02 |
| 159 | J | 4-[4-(3-Methoxy-4-phenoxy-phenylamino)-quinazolin-6-ylethynyl]-piperidin-4-ol | 467.2 | 4.77 |
| 160 | J | 4-(4-(3-Chloro-4-phenoxy-phenylamino)-quinazolin-8-ylethynyl]-piperidin-4-ol | 471.1 | 5.26 |
| 161 | J | 4-[4-(3-Methyl-4-phenoxy-phenylamino)-quinazolin-6-ylethynyl]-piperidin-4-ol | 451.2 | 5.09 |
| 162 | I | 4-[4-(1-Benzenesulfonyl-1H-indol-5-ylamino)-quinazolin-7-ylethynyl]-tetrahydro-pyran-4-ol | 525.1 | 6.02 |
| 163 | I | 4-[4-(4-Phenoxy-phenylamino) quinazolin-7-ylethynyl]-tetrahydro-pyran-4-ol | 438.1 | 6.25 |
| 164 | J | 1-(3-Aza-bicyclo[3.1.0]hex-6-yl(1α, 5α, 6α))-3-[4-(3-methoxy-4-phenoxy-phenylamino)-quinazolin-6-yl]-prop-2-yn-1-ol | 479.1 | 5.73 |
| 165 | J | 1-(3-Aza-bicyclo[3.1.0]hex-6-yl(1α,5α, 6α))-3-[4-(3-methyl-4-phenoxy-phenylamino)-quinazolin-6-yl]-prop-2-yn-1-ol | 463.1 | 5.16 |
| 166 | J | 1-(3-Aza-bicyclo[3.1.0]hex-6-yl(1α, 5α, 6α))-3-[4-(4-phenoxy-phenyl-amino)-quinazolin-6-yl]-prop-2-yn-1-ol | 449.0 | 4.89 |
| 167 | J | 3-[4-(4-Phenoxy-phenylamino) quinazolin-7-ylethynyl]-piperidin-3-ol | 437.2 | 5.09 |
| 168 | J | 3-[4-(3-Methoxy-4-phenoxy-phenylamino)-quinazolin-7-ylethynyl]-piperidin-3-ol | 467.2 | 4.97 |
| 169 | J | 3-[4-(3-Chloro-4-phenoxy-phenylamino)-quinazolin-7-ylethynyl]-piperidin-3-ol | 471.1 | 5.48 |

TABLE-continued

| Example | Method to Prepare | IUPAC name | LRMS (MH+) | HPLC Retention time (min) |
|---|---|---|---|---|
| 170 | J | 3-[4-(3-Methyl-4-phenoxy-phenylamino)-quinazolin-7-ylethynyl]-piperidin-3-ol | 451.2 | 5.35 |
| 171 | O | 4-Amino-1-[4-(3-methoxy-4-phenoxy-phenylamino)-quinazolin-6-yl]-4-methyl-pent-1-yn-3-ol | 455.2 | 4.91 |
| 172 | O | 4-Amino-4-methyl-1-[4-(3-methyl-4-phenoxy-phenylamino)-quinazolin-6-yl]-pent-1-yn-3-ol | 439.2 | 5.26 |
| 173 | J | 3-[4-(3-Ethynyl-phenylamino)-quinazolin-6-ylethynyl]-piperidin-3-ol | 369.2 | 4.11 |
| 174 | J | 3-[4-(3-Chloro-4-fluoro-phenylamino)-quinazolin-6-ylethynyl]-piperidin-3-ol | 397.1 | 4.43 |
| 175 | J | [6-(4-Amino-tetrahydro-pyran-4-ylethynyl)-quinazolinA-yl]-(3-methyl-4-phenoxy-phenyl)-amine | 451.2 | 5.43 |
| 176 | J | [6-(4-Amino-tetrahydro-pyran-4-ylethynyl)-quinazolinA-yl]-(4-phenoxy-phenyl)-amine | 437.2 | 5.15 |
| 177 | J | [6-(4-Amino-tetrahydro-pyran-4-ylethynyl)-quinazolin-4-yl]-(3-methoxy-4-phenoxy-phenyl)-amine | 467.2 | 5.00 |
| 178 | J | (3-Methoxy-4-phenoxy-phenyl)-(6-piperidin-2-ylethynyl-quinazolin-4-yl)-amine | 451.0 | 5.25 |
| 179 | J | (3-Methyl-4-phenoxy-phenyl)-(6-piperidin-2-ylethynyl-quinazolin-4-yl)-amine | 435.0 | 5.71 |
| 180 | J | (4-Phenoxy-phenyl)-(6-piperidin-2-ylethynyl-quinazolin-4-yl)-amine | 421.2 | 5.32 |
| 181 | J | (3-Chloro-4-phenoxy-phenyl)-(6-piperidin-2-ylethynyl-quinazolin-4-yl)-amine | 455.0 | 5.84 |
| 182 | J | 3-[4-(4-Phenoxy-phenylamino)-quinazolin-6-yl]-1-piperidin-2-yl-prop-2-yn-1-ol | 451.2 | 5.16 |
| 183 | J | 3-[4-(3-Methyl-4-phenoxy-phenylamino)-quinazolin-6-yl]-1-piperidin-2-yl-prop-2-yn-1-ol | 465.2 | 5.44 |
| 184 | J | 3-[4-(3-Chloro-4-phenoxy-phenylamino)-quinazolin-6-yl]-1-piperidin-2-yl-prop-2-yn-1-ol | 485.1 | 5.58 |
| 185 | J | 3-[4-(3-Methoxy-4-phenoxy-phenylamino)-quinazolin-6-yl]-1-piperidin-2-yl-prop-2-yn-1-ol | 481.2 | 5.05 |
| 186 | J | (4-Phenoxy-phenyl)-(6-piperidin-3-ylethynyl-quinazolin-4-yl)-amine | 421.2 | 5.27 |
| 187 | J | (3-Methoxy-4-phenoxy-phenyl)-(6-piperidin-3-ylethynyl-quinazolin-4-yl)amine | 451.2 | 5.21 |
| 188 | J | (3-Chloro-4-phenoxy-phenyl)-(6-piperidin-3-ylethynyl-quinazolin-4-yl)-amine | 455.0 | 5.79 |
| 189 | J | 3-[4-(4-Phenoxy-phenylamino)-quinazolin-6-yl]-1-piperidin-3-yl-prop-2-yn-1-ol | 451.0 | 5.00 |
| 190 | J | 3-[4-(3-Methyl-4-phenoxy phenylamino)-quinazolin-6-yl]-1-piperidin-3-yl-prop-2-yn-1-ol | 465.0 | 5.26 |
| 191 | J | 3-[4-(3-Methoxy-4-phenoxy-phenylamino)-quinazolin-6-yl]-1-piperidin-3-yl-prop-2-yn-1-ol | 481.0 | 4.86 |
| 192 | J | 3-[4-(3-Chloro-4-phenoxy-phenylamino)-quinazolin-6-yl]-1 piperidin-3-yl-prop-2-yn-1-ol | 485.0 | 5.34 |
| 193 | I | 1-Methyl-4-[4-(3-methyl-4-phenoxy-phenylamino)-quinazolin-6-ylethynyl]-piperidin-4-ol | 465.0 | 5.18 |
| 194 | I | 4-[4-(3-Chloro-4-phenoxy-phenylamino)-quinazoline-ylethynyl]-1-methyl-piperidin-4-ol | 485.0 | 5.34 |
| 195 | I | 4-[4-(3-Methoxy-4-phenoxy-phenylamino)-quinazolin-6-ylethynyl]-1-methyl-piperidin-4-ol | 481.0 | 4.81 |
| 196 | I | N,N-Diethyl-3-[6-(4-hydroxy-tetrahydro-pyran-4-ylethynyl)-quinazolin-4-ylamino]-benzamide | 445.3 | 4.66 |
| 197 | A | (3-(3-[4-(1-Benzenesulfonyl-1H-indol-5-ylamino)-quinazolin-6-yl]-prop-2-ynyl]-3-aza-bicyclo[3.1.0]hex-6-yl)-methanol | 550.3 | 5.38 |
| 198 | I | 4-{4-[1-(Propane-2-sulfonyl)-1H-indol-5-ylamino]-quinazolin-6-ylethynyl}-tetrahydro-pyran-4-ol | 491.2 | 5.66 |
| 199 | I | 4-[4-(1H-Indol-5-ylamino)-quinazolin-6-ylethynyl]-tetrahydro-pyran-4-ol | 385.2 | 4.22 |
| 200 | A | 1-Methyl-3-[4-(4-phenoxy-phenylamino)-quinazolin-6-ylethynyl]-piperidin-3-ol | 451.3 | 5.04 |
| 201 | J | 3-[4-(3-Chloro-4-phenoxy-phenylamino)-quinazolin-6-yl]-1-pyrrolidin-2-yl-prop-2-yn-1-ol | 471.0 | 5.40 |
| 202 | I | 1-[4-(1-Benzenesulfonyl-1H-indol-5-ylamino)-quinazolin-6-yl]-pent-1-yn-3-ol | 430.1 | 7.57 |
| 203 | I | 1-{4-[1-(Propane-2-sulfonyl)-1H-indol-5-ylamino]-quinazolin-6-yl}-pent-1-yn-3-ol | 449.2 | 6.28 |
| 204 | I | 1-[4-(3-Chloro-4-phenoxy-phenylamino)-quinazolin-8-yl]-pent-1-yn-3-ol | 430.1 | 7.57 |
| 205 | I | 1-[4-(3-Methyl-4-phenoxy phenylamino)-quinazolin-6-yl]-pent-1-yn-3-ol | 410.2 | 7.39 |
| 206 | I | 1-[4-(1-Benzyl-1H-indazol-5-ylamino)-quinazolin-6-yl]-pent-1-yn-3-ol | 434.2 | 6.16 |
| 207 | I | 1-[4-(4-Phenoxy-phenylamino)-quinazolin-6-yl]-pent-1-yn-3-ol | 396.2 | 7.04 |
| 208 | I | 3-{4-[4-(3-Fluoro-phenoxy)-3-methyl-phenylamino]-quinazolin-6-ylethynyl}-piperidin-3-ol | 469.1 | 5.32 |
| 209 | J | 3-{4-[4-(4-Methoxy-phenoxy)-3-methyl-phenylamino]-quinazolin-6-ylethynyl}-piperidin-3-ol | 481.2 | 5.10 |
| 210 | J | 4-Amino-1-[4-(3-methyl-4-phenoxy-phenylamino)-quinazolin-6-yl]-pent-1-yn-3-ol | 425.2 | 5.13 |
| 211 | J | 4-Amino-1-[4-(4-phenoxy-phenylamino)-quinazolin-6-yl]-pent-1-yn-3-ol | 410.3 | 4.86 |
| 212 | J | 4-Amino-1-[4-(3-chloro-4-phenoxy-phenylamino)-quinazolin-6-yl]-pent-1-yn-3-ol | 445.2 | 5.27 |
| 213 | J | 4-Amino-1-{4-[1-(propane-2-sulfonyl) 1H-indol-5-ylamino]-quinazolin-6-yl}-pent-1-yn-3-ol | 464.1 | 4.37 |
| 214 | J | 4-Amino-1-{4-[4-(3-fluoro-phenoxy)-3-methyl-phenylamino]-quinazolin-6-yl}-pent-1-yn-3-ol | 443.2 | 5.25 |
| 215 | J | 3-{4-[4-(4-Fluoro-phenoxy)-3-methyl-phenylamino]-quinazolin-6-ylethynyl}-piperidin-3-ol | 469.2 | 5.28 |
| 216 | J | 3-{4-[4-(2-Fluoro-phenoxy)-3-methyl-phenylamino]-quinazolin-6-ylethylnyl}-piperidin-3-ol | 469.2 | 5.22 |
| 217 | J | 3-[4-(3-Methoxy-4-phenoxy-phenylamino)-quinazolin-6-ylethynyl]-piperidin-3-ol | 467.2 | 4.85 |
| 218 | J | 3-{4-[1-(3-Fluoro-benzyl)-1H-indazol-5-ylamino]-quinazolin-6-ylethynyl}-piperidin-3-ol | 493.2 | 4.23 |

TABLE-continued

| Example | Method to Prepare | IUPAC name | LRMS (MH+) | HPLC Retention time (min) |
|---|---|---|---|---|
| 219 | J | 3-{4-[1-(3-Methoxy-benzyl)-1H-indazol-5-ylamino]-quinazolin-6-ylethynyl}-piperidin-3-ol | 505.11 | 4.41 |
| 220 | J | 3-{4-[1-(3-Methyl-benzyl)-1H-indazol-5-ylamino]-quinazolin-6-ylethynyl}-piperidin-3-ol | 489.2 | 4.70 |
| 221 | J | 3-{4-[1-(2-Fluoro-benzyl)-1H-indazol-5-ylamino]-quinazolin-6-ylethynyl}-piperidin-3-ol | 493.2 | 4.47 |
| 222 | J | 2-Chloro-N,N-diethyl-4-[6-(3-hydroxy-piperidin-3-ylethynyl)-quinazolin-4-ylamino]-benzamide | 478.2 | 4.08 |
| 223 | J | 3-[4-(3-Bromo-4-phenoxy-phenylamino)-quinazolin-6-ylethynyl]-piperidin-3-ol | 516.0 | 5.41 |
| 224 | J | 3-[4-(3,5-Dichloro-4-phenoxy-phenylamino)-quinazolin-6-ylethynyl]-piperidin-3-ol | 506.1 | 5.64 |
| 225 | J | 3-[4-(3-Methyl-4-phenylsulfanyl-phenylamino)-quinazolin-6-ylethynyl]-piperidin-3-ol | 467.2 | 5.64 |
| 226 | J | 3-[4-(3-Methoxy-4-phenoxy-phenylamino)-quinazolin-6-ylethynyl]-pyrrolidin-3-ol | 453.2 | 4.76 |
| 227 | J | 4-Amino-1-[4-(3-methoxy-4-phenoxy-phenylamino)-quinazolin-6-yl]-pent-1-yn-3-ol | 441.2 | 4.78 |
| 228 | J | 1-[4-(3-Methoxy-4-phenoxy-phenylamino)-quinazolin-6-yl]-pent-1-yn-3-ol | 426.2 | 6.83 |
| 229 | J | 3-[4-(4-Benzenesulfinyl-3-methyl-phenylamino)-quinazolin-6-ylethynyl]-piperidin-3-ol | 483.1 | 4.08 |
| 230 | J | 3-[4-(4-Benzenesulfonyl-phenylamino)-quinazolin-6-ylethynyl]-piperidin-3-ol | 485.1 | 4.49 |
| 231 | J | 3-[4-(4-Benzenesulfinyl-phenylamino)-quinazolin-6-ylethynyl]-piperidin-3-ol | 469.1 | 3.89 |
| 232 | J | 3-[4-(4-Benzenesulfonyl-3-methyl-phenylamino)-quinazolin-6-ylethynyl]-piperidin-3-ol | 499.1 | 4.65 |
| 233 | J | 3-[4-(4-Cyclopentyloxy-3-methyl-phenylamino)-quinazolin-6-ylethynyl]-Piperidin-3-ol | 443.2 | 5.30 |
| 234 | J | 3-[4-(4-Cyclobutoxy-3-methyl-phenylamino)-quinazolin-6-ylethynyl]-piperidin-3-ol | 429.2 | 4.97 |
| 235 | J | 5-[6-(3-Hydroxy-piperidin-3-ylethynyl)-quinazolin-4-ylamino]-2-phenoxy-benzonitrile | 462.2 | 4.86 |
| 236 | J | 3-[4-(4-Cyclohexyloxy-3-methyl-phenylamino)-quinazolin-6-ylethynyl]-piperidin-3-ol | 457.3 | 5.62 |
| 237 | J | 3-[4-(4-Phenylamino-phenylamino)-quinazolin-6-ylethynyl]-piperidin-3-ol | 436.2 | 4.58 |
| 238 | J | 3-[4-(3-Phenyl-1H-indazol-6-ylamino)-quinazolin-6-ylethynyl]-piperidin-3-ol | 461.2 | 3.86 |
| 239 | I | 4-[4-(3-Methyl-4-phenoxy-phenylamino)-quinazolin-6-yl]-2-methyl-but-3-yn-2-ol | 410.2 | 7.22 |
| 240 | I | 4-[4-(3-Chloro-4-phenoxy-phenylamino)-quinazolin-6-yl]-2-methyl-but-3-yn-2-ol | 430.1 | 7.39 |
| 241 | I | 4-[4-(3-Methoxy-4-phenoxy-phenylamino)-quinazolin-6-yl]-2-methyl-but-3-yn-2-ol | 426.2 | 6.67 |
| 242 | I | [6-(3-Methyl-but-1-ynyl)-quinazolin-4-yl]-(3-methyl-4-phenoxy-phenyl)-amine | 394.2 | 9.08 |
| 243 | I | (3-Methoxy-4-phenoxy-phenyl)-[6-(3-methyl-but-1-ynyl)-quinazolin-4-yl]-amine | 410.2 | 8.47 |
| 244 | I | (3-Chloro-4-phenoxy-phenyl)-[6-(3-methyl-but-1-ynyl)-quinazolin-4-yl]-amine | 414.1 | 9.21 |
| 245 | J | 3-[4-(4-Benzyl-3-methyl-phenylamino)-quinazolin-6-ylethynyl]-pipendin-3-ol | 449.2 | 5.37 |
| 246 | J | [6-(3-Amino-3-methyl-but-1-ynyl)-quinazolin-4-yl]-(3-methyl-4-phenoxy-phenyl)-amine | 395.2 | 5.13 |
| 247 | J | [6-(3-Amino-3-methyl-but-1-ynyl)-quinazolin-4-yl]-(4-phenoxy-phenyl)-amine | 409.2 | 5.45 |
| 248 | J | [6-(3-Amino-3-methyl-but-1-ynyl)-quinazolin-4-yl]-(3-methoxy-4-phenoxy-phenyl)-amine | 425.2 | 5.04 |
| 249 | J | [6-(3-Amino-3-methyl-but-1-ynyl)-quinazolin-4-yl]-(3-chloro-4-phenoxy-phenyl)-amine | 429.1 | 5.56 |
| 250 | J | [6-(3-Amino-prop-1-ynyl)-quinazolin-4-yl]-(4-phenoxy-phenyl)-amine | 367.2 | 4.78 |
| 251 | J | [6-(3-Amino-prop-1-ynyl)-quinazolin-4-yl]-(3-methyl-4-phenoxy-phenyl)-amine | 381.2 | 5.09 |
| 252 | J | [6-(3-Amino-prop-1-ynyl)-quinazolin-4-yl]-(3-methoxy-4-phenoxy-phenyl)-amine | 397.2 | 4.72 |
| 253 | J | [6-(3-Amino-prop-1-ynyl)-quinazolin-4-yl]-(3-chloro-4-phenoxy-phenyl)-amine | 401.1 | 5.28 |
| 254 | J | [6-(3-Methylamino-prop-1-ynyl)-quinazolin-4-yl]-(4-phenoxy-phenyl)-amine | 381.2 | 5.05 |
| 255 | J | [6-(3-Methylamino-prop-1-ynyl)-quinazolin-4-yl]-(3-methyl-4-phenoxy-phenyl)-amine | 395.2 | 5.32 |
| 256 | J | (3-Methoxy-4-phenoxy-phenyl)-[6-(3-methylamine-prop-1-ynyl)-quinazolin-4-yl]-amine | 411.2 | 4.87 |
| 257 | J | (3-Chloro-4-phenoxy-phenyl)-[6-(3-methylamino-prop-1-ynyl)-quinazolin-4-yl]-amine | 415.1 | 5.45 |
| 258 | A | [6-(3-Dimethylamino-prop-1-ynyl)-quinazolin-4-yl]-(3-methyl-4-phenoxy-phenyl)-amine | 409.3 | 5.94 |
| 259 | J | 3-[4-(3-Ethyl-4-phenoxy-phenylamino)-quinazolin-6-ylethynyl]-piperidin-3-ol | 465.2 | 5.54 |
| 260 | J | 3-[4-(3-Methyl-4-p-tolyloxy-phenylamino)-quinazolin-6-ylethynyl]-piperidin-3-ol | 465.2 | 5.52 |
| 261 | J | 3-[4-(3-Hydroxy-4-phenoxy-phenylamino)-quinazolin-6-ylethynyl]-piperidin-3-ol | 453.1 | 4.34 |
| 262 | J | 2-Amino-4-[4-(3-methyl-4-phenoxy-phenylamino)-quinazolin-6-yl]-but-3-yn-1-ol | 411.2 | 4.95 |
| 263 | J | 2-Amino-4-[4-(3-methoxy-4-phenoxy-phenylamino)-quinazolin-6-yl]-but-3-yn-1-ol | 427.1 | 4.60 |
| 264 | J | 3-[4-(3-Ethoxy-4-phenoxy-phenylamino)-quinazolin-6-ylethynyl]-piperidin-3-ol | 481.1 | 5.59 |
| 265 | J | 3-[4-(3-Isopropoxy-4-phenoxy-phenylamino)-quinazolin-6-ylethynyl]-piperidin-3-ol | 495.2 | 5.40 |
| 266 | J | 3-[4-(2-Fluoro-4-phenoxy-phenylamino)-quinazolin-6-ylethynyl]-piperidin-3-ol | 455.2 | 4.9 |
| 267 | J | 3-[4-(4-Fluoro-2-phenoxy-phenylamino)-quinazolin-6-ylethynyl]-piperidin-3-ol | 455.2 | 4.61 |

| Example | Method to Prepare | IUPAC name | LRMS (MH+) | HPLC Retention time (min) |
|---|---|---|---|---|
| 268 | J | 3-[4-(4-Pyridin-2-ylmethyl-phenylamino)-quinazolin-6-ylethynyl]-piperidin-3-ol | 436.2 | 3.59 |
| 269 | J | 2-Amino-1-[4-(3-methyl-4-phenoxy-phenylamino)-quinazolin-6-ylethynyl]-cyclohexanol | 465.1 | 5.45 |
| 270 | J | 2-Amino-1-[4-(3-methoxy-4-phenoxy-phenylamino)-quinazolin-6-ylethynyl]-cyclohexanol | 481.2 | 5.10 |
| 271 | J | 1-Methylamino-4-[4-(3-methyl-4-phenoxy-phenylamino)-quinazolin-6-yl]-but-3-yn-2-ol | 425.2 | 5.08 |
| 272 | J | 4-[4-Methoxy-4-phenoxy-phenylamino)-quinazolin-6-yl]-1-methylamino-but-3-yn-2-ol | 441.2 | 4.76 |
| 273 | A' | (3-Methyl-4-phenoxy-phenyl)-[6-(3-piperazin-1-yl-prop-1-ynyl)-quinazolin-4-yl]-amine | 450.0 | 5.25 |
| 274 | A | (3-Methyl-4-phenoxy-phenyl)-[6-(3-pyrrolidin-1-yl-prop-1-ynyl)-quinazolin-4-yl]-amine | 435.0 | 5.95 |
| 275 | A' | (3-Methoxy-4-phenoxy-phenyl)-[6-(3-piperazin-1-yl-prop-1-ynyl)-quinazolin-4-ayl]-amine | 466.3 | 4.95 |
| 276 | I | 3-[4-(3-Methyl-4-phenoxy-phenylamino)-quinazolin-6-ylethynyl]-1-aza-bicyclo[2.2.2]octan-3-ol | 477.2 | 5.31 |
| 277 | J | 3-{4-[4-(2,6-Difluoro-phenoxy)-3-methyl-phenylamino]-quinazolin-6-ylethynyl}-piperidin-3-ol | 487.0 | 5.22 |
| 278 | A' | {6-[3-(6-Amino-3-aza-bicyclo[3.1.0]hex-3-yl(1α, 5α, 6α))-prop-1-ynyl]-quinazolin-4-yl}-(3-methyl-4-phenoxy-phenyl)-amine | 462.3 | 5.38 |
| 279 | A | (3-Methyl-4-phenoxy-phenyl)-[6-(3-morhpolin-4-yl-prop-1-ynyl)-quinazolin-4-yl]-amine | 451.0 | 7.27 |
| 280 | A | (3-{3-[4-(3-Methyl-4-phenoxy-phenylamino)-quinazolin-6-yl]-prop-2-ynyl}-3-aza-bicyclo(3.1.0)hex-6-yl(1α, 5α, 6α))-methanol | 477.3 | 5.70 |
| 281 | A' | (3-Methyl-4-phenoxy-phenyl)-{6-[3-(2-methyl-piperazin-1-yl)-prop-1-ynyl]-quinazolin-4-yl}-amine | 464.1 | 5.49 |
| 282 | A' | {6-[3-(2,6-Dimethyl-piperazin-1-yl)-prop-1-ynyl]-quinazolin-4-yl}-(3-methyl-4-phenoxy-phenyl)-amine | 478.3 | 5.57 |
| 283 | A | (3-Methyl-4-phenoxy-phenyl)-{6-[3-(4-methyl-piperazin-1-yl)-prop-1-ynyl]-quinazolin-4-yl}-amine | 464.0 | 5.60 |
| 284 | A | 1-{3-[4-(3-Methyl-4-phenoxy-phenylamino)-quinazolin-6-yl]-prop-2-ynyl}-piperidin-4-ol | 465.0 | 5.45 |
| 285 | A | 1-{3-[4-(3-Methyl-4-phenoxy-phenylamino)-quinazolin-6-yl]-prop-2-ynyl}-pyrrolidin-3-ol | 451.3 | 5.38 |
| 286 | K | (3-Methyl-4-phenoxy-phenyl)-[6-(1-methyl-piperidin-3-ylethynyl)-quinazolin-4-yl]-amine | 449.5 | 5.86 |
| 287 | A | (1-{3-[4-(3-Methyl-4-phenoxy-phenylamino)-quinazolin-6-yl]-prop-2-ynyl}-pyrrolidin-2-yl)-methanol | 465.3 | 5.51 |
| 288 | A | (1-{3-[4-(3-Methyl-4-phenoxy-phenylamino)-quinazolin-6-yl]-prop-2-ynyl}-piperidin-2-yl)-methanol | 479.1 | 5.58 |
| 289 | A | (1-{3-[4-(3-Methyl-4-phenoxy-phenylamino)-quinazolin-6-yl]-prop-2-ynyl}-piperidin-3-yl)-methanol | 478.9 | 5.59 |
| 290 | A | 2-(Methyl-{3-[4-(3-methyl-4-phenoxy-phenylamino)-quinazolin-6-yl]-prop-2-ynyl}-amino)-ethanol | 439.1 | 5.45 |
| 291 | A' | 3-Methyl-2-3-{4-(3-methyl-4-phenoxy-phenylamino)-quinazolin-6-yl]-prop-2-ynylamino}-butan-1-ol | 467.4 | 5.72 |
| 292 | A | (3-Methyl-4-phenoxy-phenyl)-[6-(2-piperidin-3-yl-ethyl)-quinazolin-4-yl]-amine | 439.3 | 5.33 |
| 293 | A | 4-[4-(3-Methyl-4-phenoxy phenylamino)-quinazolin-6-ylethynyl]-tetrahydro-pyran-4-ol | 452.1 | 6.76 |
| 294 | A | 4-[4-(3-Chloro-4-phenoxy-phenylamino)-quinazolin-6-ylethynyl]-tetrahydro-pyran-4-ol | 471.9 | 6.94 |
| 295 | K | 4-[4-(3-Methoxy-4-phenoxy-phenylamino)-quinazolin-6-ylethynyl]-tetrahydro-pyran-4-ol | 467.9 | 6.23 |
| 296 | A | 4-Methyl-2-{3-[4-(3-methyl-4-phenoxy-phenylamino)-quinazolin-6-yl]-prop-2-ynylamino}-pentan-1-ol | 481.0 | 5.99 |
| 297 | A' | 3-{3-[4-(3-Methyl-4-phenoxy-phenylamino)-quinazolin-6-yl]-prop-2-ynylamino}-propane-1,2-diol | 495.0 | 4.94 |
| 298 | A | 1-{3-[4-(3-Methy-4-phenoxy-phenylamino)-quinazolin-6-yl]-prop-2-ynyl}-pyrrolidine-2-carboxylic acid methyl ester | 493.3 | 7.90 |
| 299 | K | (3-Methyl-4-phenoxy-phenyl)-[6-(1-propyl-piperidin-3-ylethynyl)-quinazolin-4-yl]-amine | 477.1 | 6.24 |
| 300 | A' | {6-[3-(4-Amino-piperidin-1-yl)-prop-1-ynyl]-quinazolin-4-yl}-(3-methyl-4-phenoxy-phenyl)-amine | 464.3 | 5.10 |
| 301 | K' | {6-[1-(2-Amino-ethyl)-piperidin-3-ylethynyl]-quinazolin-4-yl}-(3-methyl-4-phenoxy-phenyl)-amine | 478.1 | 5.84 |
| 302 | A | 1-{3-[4-(3-Methoxy-4-phenoxy-phenylamino)-quinazolin-6-yl]-prop-2-ynyl}-pyrrolidine-2-carboxylic acid methyl ester | 509.0 | 7.37 |
| 303 | A | (1-{3-[4-(3-Methyl-4-phenoxy-phenylamino)-quinazolin-6-yl]-prop-2-ynyl}-piperidin-4-yl)-methanol | 479.3 | 5.40 |
| 304 | A | (1-{-3-[4-(3-Methoxy-4-phenoxy-phenylamino)-quinazolin-6-yl]-prop-2-ynyl}-piperidin-4-yl)-methanol | 495.3 | 4.99 |
| 305 | A | {6-[3-(4,4-Dimethoxy-piperidin-1-yl)-prop-1-ynyl]-quinazolin-4-yl}-(3-methyl-4-phenoxy-phenyl)-amine | 509.2 | 7.33 |
| 306 | A | {6-[3-(3-Dimethylamino-pyrrolidin-1-yl)-prop-1-ynyl]-quinazolin-4-yl}-(3-methyl-4-phenoxy-phenyl)-amine | 478.3 | 5.85 |
| 307 | A | 2-(1-{3-[4-(3-Methyl-4-phenoxy-phenylamino)-quinazolin-6-yl]-prop-2-ynyl}-piperidin-4-yl)-ethanol | 493.1 | 5.50 |
| 308 | K' | {6-[1-(2-Amino-propyl)-piperidin-3-ylethynyl]-quinazolin-4-yl}-(3-methyl-4-phenoxy-phenyl)-amine | 492.4 | 6.28 |
| 309 | K | 2-3-[4-(3-Methyl-4-phenoxy-phenylamino)-quinazolin-6-ylethynyl]-piperidin-1-yl}-ethanol | 479.3 | 5.66 |
| 310 | J | 3-[4-(4-Bromo-2-[fluoro-phenylamino)-quinazolin-6-ylethynyl]-piperidin-3-ol | 442.9, 440.9 | 4.26 |
| 311 | J | 3-[4-(4-Bromo-2,6-difluoro-phenylamino)-quinazolin-6-ylethynyl]-piperidin-3-ol | 460.9, 459.1 | 4.24 |
| 312 | K | {6-[1-(2-Methoxy-ethyl)-piperidin-3-ylethynyl]quinazolin-4-yl}-(3-methyl-4-phenoxy-phenyl)-amine | 493.1 | 6.05 |
| 314 | J | 6-Hydroxymethyl-3-[4-(3-methyl-4-phenoxy-phenylamino)-quinazolin-6-ylethynyl]-piperidin-3-ol | 424.2 | 8.64 |
| 315 | A' | {6-[3-(2,5-Diaza-bicyclo[2.2.1]hept-2-yl)-prop-1-ynyl]-quinazolin-4-yl}-(3-methoxy-4-phenoxy-phenyl)-amine | 478.2 | 4.92 |

TABLE-continued

| Example | Method to Prepare | IUPAC name | LRMS (MH+) | HPLC Retention time (min) |
|---|---|---|---|---|
| 316 | A | {6-[3-(6-Dimethylamino-3-aza-bicyclo[3.1.0]hex-3-yl(1α, 5α, 6α))-prop-1-ynyl]-quinazolin-4-yl}-(3-methoxy-4-phenoxy-phenyl)-amine | 506.1 | 5.28 |
| 317 | J | 5-Hydroxy-5-[4-(3-methyl-4-phenoxy-phenylamino)-quinazolin-6-ylethynyl]-piperidine-2-carboxylic acid amide | 494.0 | 5.11 |
| 318 | A | 2-(4-{3-[4-(3-Methyl-4-phenoxy-phenylamino)-quinazolin-6-yl]-prop-2-ynyl}-piperazin-1-yl)-ethanol | 494.4 | 5.17 |
| 319 | A | 2-(4-(3-(4-(3-Methoxy-4-phenoxy-phenylamino)-quinazolin-6-yl]-prop-2-ynyl}-piperazin-1-yl)-ethanol | 510.1 | 4.89 |
| 320 | J | 3-Hydroxymethyl-4-[4-(3-methyl-4-phenoxy-phenylamino)-quinazolin-6-ylethynyl]-piperidin-4-ol | 481.0 | 4.94 |
| 321 | J | 3-Hydroxymethyl-4-(4-(3-methoxy-4-phenoxy-phenylamino)-quinazolin-6-ylethynyl]-piperidin-4-ol | 497.0 | 4.63 |
| 322 | A | 1-(3-(4-(3-Methyl-4-phenoxy-phenylamino)-quinazolin-6-yl]-prop-2-ynyl}-piperidin-4-one | 463.1 | 7.17 |
| 323 | J | (3-Methyl-4-phenoxy-phenyl)-(6-(3-thiomorpholin4-yl-prop-1-ynyl)-quinazolin-4-yl]-amine | 467.3 | 8.06 |
| 324 | J | 5-Hydroxymethyl-3-(4-(3-methyl-4-phenoxy-phenylamino)-quinazolin-6-ylethynyl]-pyrrolidin-3-ol | 466.9 | 5.04 |
| 325 | J | 5-Hydroxymethyl-3-(4-(3-methoxy4-phenoxy-phenylamino)-quinazolin-6-ylethynyl]-pyrrolidin-3-ol | 482.9 | 4.72 |
| 326 | A | 1-(3-(4-(3-Methyl-4-phenoxy-phenylamino)-quinazolin-6-yl]-prop-2-ynyl}-piperidin-4-one oxime | 478.3 | 6.43 |
| 327 | J | 2-Hydroxymethyl-3-(4-(3-methyl-4-phenoxy-phenylamino)-quinazolin-6-ylethynyl]-tetrahydro-pyran-3-ol | 482.0 | 6.13 |
| 328 | A | 4-{3-(4-(3-Methyl-4-phenoxy-phenylamino)-quinazolin-6-yl]-prop-2-ynyl}-piperazine-1-carboxylic acid ethyl ester | 522.1 | 7.78 |
| 329 | A | 4-{3-[4-(3-Methoxy-4-phenoxy-phenylamino)-quinazolin-6-yl]-prop-2-ynyl}-piperazine-1-carboxylic acid ethyl ester | 538.3 | 7.16 |
| 330 | J | 4-Hydroxy-4-(4-(3-methoxy-4-phenoxy-phenylamino)-quinazolin-6-ylethynyl]-pyrrolidine-2-carboxylic acid amide | 496.1 | 4.70 |
| 331 | J | 4-[4-(3-Chloro-4-phenoxy-phenylamino)-quinazolin-6-ylethynyl]-4-hydroxy-pyrrolidine-2-carboxylic acid amide | 500.2 | 5.21 |
| 332 | J | 4-Hydroxy-4-(4-(3-methyl-4-phenoxy-phenylamino)-quinazolin-6-ylethynyl]-pyrrolidine-2-carboxylic acid amide | 480.3 | 5.03 |
| 333 | A | N-{3-[4-(3-Methyl-4-phenoxy-phenylamino)-quinazolin-6-yl]-prop-2-ynyl}-methanesulfonamide | 459.0 | 6.85 |
| 334 | A | 1-(4-3-[4-(3-Methyl-4-phenoxy-phenylamino)-quinazolin-8-yl]-prop-2-ynyl}-piperazin-1-yl)-ethanone | 492.3 | 6.39 |
| 335 | I | 4-Hydroxy-4-(4-(3-methyl-4-phenoxy-phenylamino)-quinazolin-6-ylethynyl]-tetrahydro-pyran-2-carboxylic acid amide | 495.3 | 5.90 |
| 336 | J | 4-Hydroxy4-[4-(3-methoxy-4-phenoxy-phenylamino)-quinazolin-6 ylethynyl]-tetrahydro-pyran-2-carboxylic acid amide | 511.1 | 5.49 |
| 337 | J | 4-[4-(3-Chloro-4-phenoxy-phenylamino)-quinazolin-8-ylethynyl]-4-hydroxy-tetrahydro-pyran-2 carboxylic acid amide | 515.2 | 6.09 |
| 338 | A | N-{3-[4-(3-Methoxy-4-phenoxy-phenylamino)-quinazolin-8-yl]-prop-2-ynyl}-methanesulfonamide | 475.1 | 6.40 |
| 339 | A | {6-[3-(4-Methanesulfonyl-piperazin-1-yl)-prop-1-ynyl]-quinazolin-4-yl}-(3-methyl-4-phenoxy-phenyl)-amine | 528.1 | 7.08 |
| 340 | A | 4-{3-[4-(3-Methyl-4-phenoxy-phenylamino)-quinazolin-8-yl]-prop-2 ynyl}-piperazine-1-carboxylic acid methylamide | 507.3 | 6.12 |
| 341 | A | 4-{3-[4-(3-Methoxy-4-phenoxy-phenylamino)-quinazolin-8-yl]-prop-2 ynyl}-piperazine-1-carboxylic acid methylamide | 523.2 | 5.64 |
| 342 | A | {6-[3-(4-Methanesulfonyl-piperazin-1-yl)-prop-1-ynyl]-quinazolin-4-yl}-(3-methoxy-4-phenoxy-phenyl)-amine | 544.1 | 6.54 |
| 343 | J | 2-Hydroxymethyl-4-[4-(3-methyl-4-phenoxy-phenylamino)-quinazolin-8-ylethynyl]-tetrahydro-pyran-4-ol | 482.3 | 5.85 |
| 344 | J | 2-Hydroxymethyl-4-[4-(3-methoxy-4-phenoxy-phenylamino)-quinazolin-8-ylethynyl]-tetrahydro-pyran-4-ol | 498.3 | 5.43 |
| 345 | J | 4-[4-(3-Chloro-4-phenoxy-phenylamino)-quinazolin-8-ylethynyl]-2-hydroxymethyl-tetrahydro-pyran-4-ol | 502.2 | 6.04 |
| 346 | A | {6-[3-(1,1-Dioxo-1&-isothiazolidin-2-yl)-prop-1-ynyl]-quinazolin-4-yl}-(3-methyl-4-phenoxy-phenyl)-amine | 485.3 | 7.30 |
| 347 | A | {6-[3-(1,1-Dioxo-1&-isothiazolidin-2-yl)-prop-1-ynyl]-quinazolin-4-yl}-(3-methoxy-4-phenoxy-phenyl)-amine | 501.3 | 6.69 |
| 348 | I | N-{3-[4-(4-Phenoxy-phenylamino)-quinazolin-8-yl]-prop-2-ynyl}-acetamide | 409.0 | 6.03 |
| 349 | I | N-{3-[4-(3-Chloro-4-phenoxy-phenylamino)-quinazolin-8-yl]-prop-2-ynyl}-acetamide | 442.9 | 6.55 |
| 350 | A | {6-[3-(1,1-Dioxo-1&-thiomorpholin-4-yl)-prop-1-ynyl]-quinazolin-4-yl}-(3-methoxy-4-phenoxy-phenyl)-amine | 515.2 | 6.40 |
| 351 | A | 4-{3-[4-(3-Methyl-4-phenoxy-phenylamino)-quinazolin-6-yl]-prop-2-ynylamino}-piperidine-1-carboxylic acid ethyl ester | 536.6 | 6.04 |
| 352 | A | 4-{3-[4-(3-Methoxy-4-phenoxy-phenylamino)-quinazolin-6-yl]-prop-2-ynylamino}-piperidine-1-carboxylic acid ethyl ester | 552.3 | 5.97 |
| 353 | J | N-{3-[4-(3-Methyl-4-phenoxy-phenylamino)-quinazolin-6-yl]-prop-2-ynyl}-isobutyramide | 451.3 | 7.09 |
| 354 | J | [4-(2-Fluoro-phenoxy-)-3-methyl-phenyl]-(6-piperidin-3-ylethynyl-quinazolin-4-yl)-amine | 453.4 | 5.55 |
| 355 | J | [4-(3-Fluoro-phenoxy-)-3-methyl-phenyl]-(6-piperidin-3-ylethynyl-quinazolin-4-yl)-amine | 453.4 | 5.75 |
| 356 | I | N-Methyl-N-[3-[4-(4-phenoxy-phenylamino)-quinazolin-6-yl]-prop-2-ynyl}-acetamide | 423.3 | 6.53 |
| 357 | A | N-Methyl-N-[3-(4-(3-methyl-4-phenoxy-phenylamino)-quinazolin-6-yl]-prop-2-ynyl}-acetamide | 437.3 | 6.86 |
| 358 | I | N-{3-[4-(3-Chloro-4-phenoxy-phenylamino)-quinazolin-6-yl]-prop-2-ynyl}-N-methyl-acetamide | 457.3 | 7.05 |

TABLE-continued

| Example | Method to Prepare | IUPAC name | LRMS (MH+) | HPLC Retention time (min) |
|---|---|---|---|---|
| 359 | I | 2,2-Dimethyl-N-{3-[4-(3-methyl-4-phenoxy-phenylamino)-quinazolin-6-yl]-prop-2-ynyl}-propionamide | 465.0 | 7.57 |
| 360 | J | (3-Methyl-4-phenoxy-phenyl)-(6-pyrrolidin-3-ylethynyl-quinazolin-4-yl)-amine | 421.3 | 5.43 |
| 361 | J | [4-(2-Fluoro-phenoxy-)-3-methyl-phenyl]-(6-pyrrolidin-3-ylethynyl-quinazolin-4-yl)-amine | 439.0 | 5.39 |
| 362 | J | (3-Chloro-4-phenoxy-phenyl)-(6-pyrrolidin-3-ylethynyl-quinazolin-4-yl)-amine | 441.0 | 5.61 |
| 363 | J | (3-Methoxy-4-phenoxy-phenyl)-(6-pyrolidin-3-ylethynyl-quinazolin-4-yl)-amine | 437.1 | 5.06 |
| 364 | I | 2-Chloro-N-[3-(4-(3-methyl-4-phenoxy-phenylamino)-quinazolin-8-yl]-prop-2-ynyl]-acetamide | 457.0 | 7.00 |
| 365 | I | Cyclopropanecarboxylic acid {3-[4-(3-methyl-4-phenoxy-phenylamino)-quinazolin-6-yl]-prop-2-ynyl}-amide | 449.1 | 6.97 |
| 366 | I | N-{3-(4-(3-Methyl-4-phenoxy-phenylamino)-quinazolin-6-yl]-prop-2-ynyl}-propionamide | 437.1 | 6.74 |
| 367 | I | 2-Methoxy-N-{3-[4-(3-methyl-4-phenoxy-phenylamino)-quinazolin-6-yl]-prop-2-ynyl}-acetamide | 453.2 | 6.69 |
| 368 | M | N-{3-[4-(3-Methyl-4-phenoxy-phenylamino)-quinazolin-6-yl]-prop-2-ynyl}-2-morpholin4-yl-acetamide | 508.0 | 6.49 |
| 369 | A' | 1-{3-[4-(3-Methyl-4-phenoxy-phenylamino)-quinazolin-6-yl]-prop-2-ynyl}-piperazine-2-carboxylic acid methyl ester | 508.0 | 5.66 |
| 370 | A | 4-{3-[4-(3-Methyl-4-phenoxy-phenylamino)-quinazolin-6-yl]-prop-2-ynyl}-piperazine-1-carboxylic acid amide | 493.5 | 5.87 |
| 371 | J | (-)-(3-Methyl-4-phenoxy-phenyl)-(6-piperidin-3(S)-ylethynyl-quinazolin-4-yl)-amine | 435.1 | 5.61 |
| 372 | A' | 4-Aminomethyl-1-{3-[4-(3-methyl-4-phenoxy-phenylamino)-quinazolin-6-yl]-prop-2-ynyl}-pyrrolidin-3-ol | 480.3 | 4.95 |
| 373 | J | 4-Hydroxy-4-[4-(3-methyl-4-phenoxy-phenylamino)-quinazolin-6-ylethynyl]-pyrrolidine-2-carboxylic acid methylamide | 494.0 | 5.18 |
| 374 | N | (3-Methyl-4-phenoxy-phenyl)-(6-piperidin-3-ylethynyl-pyrido[3,4-d]pyrimidin-4-yl)-amine | 436.3 | 5.40 |
| 375 | N | (3-Methyl-4-phenoxy-phenyl)-(6-piperidin-4-ylethynyl-pyrido(3,4-d]pyrimidin4-yl)-amine | 436.3 | 5.32 |
| 376 | J | (3-Methoxy-4-phenoxy-phenyl)-(6-piperidin-4-ylethynyl-quinazolin-4-yl)-amine | 451.3 | 5.17 |
| 377 | J | (3-Chloro-4-phenoxy-phenyl)-(6-piperidin-4-ylethynyl-quinazolin-4-yl)-amine | 455.0 | 5.73 |
| 378 | J | (3-Methyl-4-phenoxy-phenyl)-(6-piperidin-4-ylethynyl-quinazolin-4-yl)-amine | 435.1 | 5.56 |
| 379 | A | 3(S)-[4-(3-Methyl-4-phenoxy-phenylamino)-quinazolin-6-ylethynyl]-piperidin-1-carboxylic acid methylamide | 492.3 | 7.15 |
| 380 | I | 3(S)-[4-(3-Methoxy-4-phenoxy-phenylamino)-quinazolin-6-ylethynyl]-piperidine-1-carboxylic acid methylamide | 509.4 | 6.65 |
| 381 | I | N-{1,1-Dimethyl-3-[4-(3-methyl-4-phenoxy-phenylamino)-quinazolin-6-yl]-prop-2-ynyl]-2,2,2-trifluoro-acetamide | 505.0 | 8.15 |
| 382 | J | (+)-(3-Methyl-4-phenoxy-phenyl)-(6-piperidin-3(R)-ylethynyl-quinazolin-4-yl)-amine | 435.3 | 5.61 |
| 383 | I | N-{1,1-Dimethyl-3-[4-(3-methyl-4-phenoxy-phenylamino)-quinazolin-6 yl]-prop-2-ynyl}-acetamide | 451.2 | 7.00 |
| 384 | I | N-{3-[4-(3-Chloro-4-phenoxy-phenylamino)-quinazolin-6-yl]-1,1-dimethyl-prop-2-ynyl}-acetamide | 471.1 | 7.22 |
| 385 | J | [4-(2-Chloro-phenoxy-)-3-methyl-phenyl]-(6-piperidin-3-ylethynyl-quinazolin-4-yl)-amine | 469.0 | 5.97 |
| 386 | J | [4-(2-Methoxy-phenoxy-)-3-methyl phenyl]-(6-piperidin-3-ylethynyl-quinazolin-4-yl)-amine | 465.1 | 5.31 |
| 387 | J | [3-Methyl-4-(2-trifluoromethyl-phenoxy-)-phenyl]-(6-piperidin-3-ylethynyl-quinazolin-4-yl)-amine | 503.0 | 6.17 |
| 388 | J | [4-(2-Ethyl-phenoxy-)-3-methyl-phenyl]-(6-piperidin-3-ylethynyl-quinazolin-4-yl)-amine | 463.0 | 6.38 |
| 389 | J | (6-Azetidin-3-ylethynyl-quinazolin-4-yl)-(3-methyl-4-phenoxy-phenyl)-amine | 407.3 | 5.31 |
| 390 | I | N-{1-Methyl-3-[4-(3-chloro-4-phenoxy-phenylamino)-quinazolin-6-yl]-prop-2-ynyl}-acetamide | 456.9 | 6.84 |
| 391 | I | N-{1-Methyl-3-[4-(3-methyl-4-phenoxy-phenylamino)-quinazolin-6-yl]-prop-2-ynyl}-acetamide | 437.1 | 6.65 |
| 392 | I | N-{3-[4-(3-Methyl-4-phenoxy-phenylamino)-quinazolin-6-yl]-prop-2 ynyl}-acetamide | 422.8 | 6.36 |

Utilizing method I and the appropriate starting materials (prepared according to odology known in the art), the following compounds (and pharmaceutically acceptable and solvates thereof), which are part of the present invention, may be prepared:

1-{3-[4-(3-Methyl-4-phenoxy-phenylamino)-quinazolin-6-ylethynyl]-azetidin-1-yl}-ethanone 1-{3-[4-(3-Methoxy-4-phenoxy-phenylamino)-quinazolin-6-ylethynyl]-azetidin-1-yl}-ethanone 1-{3-[4-(3-Chloro-4-phenoxy-phenylamino)-quinazolin-6-ylethynyl]-azetidin-1-yl}-ethanone

[6-(1-Methanesulfonyl-azetidin-3-ylethynyl)-quinazolin-4-yl]-(3-methyl-4-phenoxy-phenyl)-amine

[6-(1-Methanesulfonyl-azetidin-3-ylethynyl)-quinazolin-4-yl]-(3-methoxy-4-phenoxy-phenyl)-amine

[6-(1-Methanesulfonyl-azetidin-3-ylethynyl)-quinazolin-4-yl]-(3-chloro-4-phenoxy-phenyl)-amine

[6-(1-Methanesulfonyl-pyrrolidin-3-ylethynyl)-quinazolin-4-yl]-(3-methyl-4-phenoxy-phenyl)-amine

[6-(1-Methanesulfonyl-pyrrolidin-3-ylethynyl)-quinazolin-4-yl]-(3-methoxy-4-phenoxy-phenyl)-amine

[6-(1-Methanesulfonyl-pyrrolidin-3-ylethynyl)-quinazolin-4-yl]-(3-chloro4-phenoxy-phenyl)-amine 1-{3-[4-(3-Methyl-4-phenoxy-phenylamino)-quinazolin-6-ylethynyl]-pyrrolidin-1-yl}-ethanone 1-{3-[4-(3-Methoxy-4-phenoxy-phenylamino)-quinazolin-6-ylethynyl]-pyrrolidin-1-yl}-ethanone 1-{3-[4-(3-Chloro4-phenoxy-phenylamino)-quinazoin-6-ylethynyl]-pyrrolidin-1-yl}-ethanone
1-{3-[4-(3-Methyl-4-phenoxy-phenylamino)-quinazolin-6-ylethynyl]-piperdin-1-yl}-ethanone
1-{3-[4-(3-Methoxy-4-phenoxy-phenylamino)-quinazolin-6-ylethynyl]-piperidin-1-yl}-ethanone
1-{3-[4-(3-Chloro-4-phenoxy-phenylamino)-quinazolin-6-ylethynyl]-piperidin-1-yl}-ethanone
[6-(1-Methanesulfonyl-piperidin-3-ylethynyl)-quinazolin-4-yl}-(3-methyl-4-phenoxy-phenyl)-amine
[6-(1-Methanesulfonyl-piperidin-3-ylethynyl)-quinazolin-4-yl]-(3-methoxy-4-phenoxy-phenyl)-amine
[6-(1-Methanesulfonyl-piperidin-3-ylethynyl)-quinazolin-4-yl}-(3-chloro-4-phenoxy-phenyl)-amine
5-[4-(3-Methyl-4-phenoxy-phenylamino)-quinazolin-6-ylethynyl]-piperidin-2-one
5-[4-(3-Methoxy-4-phenoxy-phenylamino)-quinazolin-6-ylethynyl]-piperidin-2-one
5-[4-(3-Chloro4-phenoxy-phanylamino)-quinazolin-6-ylethynyl]-piperidin-2-one
4-[4-(3-Methyl-4-phenoxy-phenylamino)-quinazolin-4-ylethynyl]-pyrolidin-2-one
4-[4-(3-Methoxy 4phenoxy-phenylamino)-quinazolin-6-ylethynyl]-pyrrolidin-2-one
4-[4-(3-Chloro4-phenoxy-phenylamino)-quinazolin-6-ylethynyl]-pyrrolidin-2-one
1-{2-[4-(3-Methyl-4-phenoxy-phenylamino)-quinazolin-6-ylethynyl]-morpholin-4-yl}-ethanone
1-{2-[4-(3-Methoxy-4-phenoxy-phenylamino)-quinazolin-6-ylethynyl]-morpholin-4-yl}-ethanone
1-{2-[4-(3-Chloro-4-phenoxy-phenylamino)-quinazolin-ylethynyl]-morpholin-4-yl}-ethanone
[6-(4-Methanesulfonyl-morpholin-2-ylethynyl)-quinazolin-4-yl]-(3-methyl-4-phenoxy-phenyl)-amine
[6-(4-Methanesulfonyl-morpholin-2-ylethynyl)-quinazolin-4-yl]-(3-methoxy-4-phenoxy-phenyl)-amine
[6-(4-Methanesulfonyl-morpholin-2-ylethynyl)-quinazolin-4-yl]-(3-chloro4-phenoxy-phenyl)-amine
6-[4-(3-Methyl-4-phenoxy-phenylamino)-quinazolin-6-ylethynyl]-morpholin-3-one
6-[4-(3-Methoxy-4-phenoxy-phenylamino)-quinazolin-6-ylethynyl]-morpholin-3-one
6-[4-(3-Chloro-4-phenoxy-phenylamino)-quinazolin-6-ylethynyl]-morpholin-3-one
5-[4-(3-Methyl-4-phenoxy-phenylamino)-quinazolin-6-ylethynyl]-piperazin-2-one
5-[4-(3-Methoxy-4-phenoxy-phenylamino)-quinazolin-6-ylethynyl]-piperazin-2-one
5-[4-(3-Chloro-4-phenoxy-phenylamino)-quinazolin-6-ylethynyl]-piperazin-2-one
6-[4-(3-Methyl-4-phenoxy-phenylamino)-quinazolin-6-ylethynyl]-piperazin-2-one
6-[4-(3-Methoxy-4-phenoxy-phenylamino)-quinazolin-6-ylethynyl]-piperazin-2-one
6-[4-(3Chloro-4-phenoxy-phenylamino)-quinazolin-6-ylethynyl]-piperazin-2-one
1-{5-[4-(3-Methyl-4-phenoxy-phenylamino)-quinazolin-6-ylethynyl]-3,4-dihydro-2H-pyridin-1-yl)-ethanone
1-{5-[4-(3-Methoxy-4-phenoxy-phenylamino)-quinazolin-6-ylethynyl]-3,4-dihydro-2H-pyridin-1-yl)-ethanone
1-{5-[4-(3-Chloro-4-phenoxy-phenylamino)-quinazolin-6-ylethynyl]-3,4-dihydro-2H-pyridin-1-yl)ethanone
[6-(1-Methanesulfonyl-1,4,5,6-tetrahydro-pyridin-3-ylethynyl)-quinazolin-4-yl]-(3-methyl-4-phenoxy-phenyl)-amine
[6-(1-Methanesulfonyl-1,4,5,6-tetrahydro-pyridin-3-ylethynyl)-quinazolin-4-yl]-(3-methoxy-4-phenoxy-phenyl)-amine
[6-(1-Methanesulfonyl-1,4,5,6-tetrahydro-pyridin-3-ylethynyl)-quinazolin-4-yl]-(3-chloro-4-phenoxy-phenyl)-amine
1-{5-[4-(3-Methyl-4-phenoxy-phenylamino)-quinazolin-6-ylethynyl]-3,6-dihydro-2H-pyridin-1-yl}-ethanone
1-{5-[4-(3-Methoxy-4-phenoxy-phenylamino)-quinazolin-6-ylethynyl]-3,6-dihydro-2H-pyridin-1-yl}ethanone
1-{5-[4-(3-Chloro4-phenoxy-phenylamino)-quinazolin-6-ylethynyl]-3,6-dihydro-2H-pyridin-1-yl}petanone
[6-(1-Methanesulfonyl-1,2,5,6-tetrahydo-pyridin-3-ylethynyl)-quinazolin-4-yl]-(3-methyl-4-phenoxy-phenyl)-amine
[6-(1-Methanesulfonyl-1 2,5,6-tetrahydro-pyridin-3-ylethynyl)-quinazolin-4-yl]-(3-methoxy-4-phenoxy-phenyl)-amine
[6-(1-Methanesulfonyl-1,2,5,6-tetrahydro-pyridin-3-ylethynyl)-quinazolin-4-yl]-(3-chloro-4-phenoxy-phenyl)-amine
1-{4-[4-(3-Methylphenoxy-phenylamino)-quinazolin-6-ylethynyl]-3,6-dihydro-2H-pyridin-1-yl}ethanone
1-{4-[4-(3-Methoxy-4-phenoxy-phenylamino)-quinazolin-6-ylethynyl]-3,6-dihydro-2H-pyridin-1-yl}-ethanone
1-{4-[4-(3-Chloro4-phenoxy-phenylamino)-quinazolin-6-ylethynyl]-3,6-dihydro-2H-pyridin-1-yl}-ethanone
[6-(1-Methanesulfonyl-1,2,3,6-tetrahydro-pyridin-4-ylethynyl)-quinazolin-4-yl]-(3-methyl-4-phenoxy-phenyl)-amine
[6-(1-Methanesulfonyl-1,2,3,6-tetrahydro-pyridin-4-ylethynyl)-quinazolin-4-yl]-(3-methoxy-4-phenoxy-phenyl)-amine
[6-(1-Methanesulfonyl-1,2,3,6-tetrahydro-pyridin-4-ylethynyl)-quinazolin-4-yl]-(3-chloro-4-phenoxy-phenyl)-amine
N-{1,1-Dimethyl-3-[4-(3-methyl-4-phenoxy-phenylamino)-quinazolin-6-yl]-prop-2-ynyl}-acetamide
N-{1,1-Dimethyl-3-[4-(3-methoxy-4-phenoxy-phenylamino)-quinazolin-6-yl]-prop-2-ynyl}-acetamide
N-{1,1-Dimethyl-3-[4-(3-chloro4-phenoxy-phenylamino)-quinazolin-6-yl]-prop-2-ynyl}-acetamide
N-{1,1-Dimethyl-3-[4-(3-methyl-4-phenoxy-phenylamino)-quinazolin-6-yl]-prop-2-ynyl}-methanesulfonamide
N-{1,1-Dimethyl-3-[4-(3-methoxy-4-phenoxy-phenylamino)-quinazolin-6-yl]-prop-2-ynyl}-methanesulfonamide
N-{1,1-Dimethyl-3-[4-(3-chloro4-phenoxy-phenylamino)-quinazolin-6-yl]-prop-2-ynyl}-methanesulfonamide
N-{1-Methyl-3-[4-(3-methyl-4-phenoxy-phenylamino)-quinazolin-6-yl]-prop-2-ynyl}-acetamide N-{1-Methyl-3-[4-(3-methoxy-4-phenoxy-phenylamino)-quinazolin-6-yl]-prop-2-ynyl}-acetamide N-{1-Methyl-3-[4-(3-chloro-4-phenoxy-phenylamino)-quinazolin-6-yl]-prop-2-ynyl}-acetamide N-{1-Methyl-3-[4-(3-methyl-4-phenoxy-phenylamino)-quinazolin-6-yl]-prop-2-ynyl}-methanesulfonamide N-{1-Methyl-3-[4-(3-methoxy-54-phenoxy-phenylamino)-quinazolin 6-yl]-prop-2-ynyl}-methanesulfonamide N-{1-Methyl-3-[4-(3-chloro-4-phenoxy-phenylamino)-quinazolin-6-yl]-prop-2-ynyl}-methanesulfonamide 1-{3-[4-(3-Methyl-4-phenoxy-phenylamino)-quinazolin-6-yl]-prop-2-ynyl}-piperidin-2-one 1-{3-[4-(3-Methoxy-4-phenoxy-phenylamino)-quinazolin-6-yl]-prop-2-ynyl}-piperidin-2-one 1-{3-[4-(3-Chloro-4-phenoxy-phenylamino)-quinazolin 6-yl]-prop-2-ynyl}-piperidin-2-one 1-{3-[4-(3-Methyl-4-phenoxy-phenylamino)-quinazolin-6-yl]-prop-2-ynyl}-pyrrolidin-2-one 1-{3-[4-(3-Methoxy-4-phenoxy-phenylamino)-quinazolin-6-yl]-prop-2-ynyl}-pyrrolidin-2-one 1-{3-[4-(3-Chloro4-phenoxy-phenylamino)-quinazolin-6-yl]-prop-2-ynyl}-pyrrolidin-2-one Utilizing method J and the appropriate starting materials (prepared according to methodology known in the art), the following compounds (and pharmaceutically acceptable salts and solvates thereof, which are part of the present invention, may be prepared:

(7-Methoxy-6-piperidin-3-ylethynyl-quinazolin-4-yl)-(3-methyl-4-phenoxy-phenyl)-amine (3-Chloro-4-phenoxy-phenyl)-(7-methoxy-6-piperidin-3-ylethynyl-quinazolin-4-yl)-amine (3-Methoxy-4-phenoxy-phenyl)-(7-methoxy-6-piperidin-3-ylethynyl-quinazolin-4-yl)-amine

[7-(2-Methoxy-ethoxy)-6-piperidin-3-ylethynyl-quinazolin-4-yl]-(3-methyl-4-phenoxy-phenyl)-amine (3-Chloro-4-phenoxy-phenyl)-[7-(2-methoxyethoxy)-6-piperidin-3-ylethynyl-quinazolin-4-yl]-amine

[7-(2-Methoxy-ethoxy)-[6-piperidin-3-ylethynyl-quinazolin-4-yl]-(3-methoxy-4-phenoxy-phenyl)-amine 3-[7-(2-Methoxy-ethoxy)-4-(3-methyl-4-phenoxy-phenylamino)-quinazolin-6-ylethynyl]-piperidin-3-ol 3-[7-(2-Methoxy-ethoxy)-4-(3-chloro-4-phenoxy-phenylamino)-quinazolin-6-ylethynyl]-piperidin-3-ol 3-[7-(2-Methoxy-ethoxy)-4-(3-methoxy-4-phenoxy-phenylamino)-quinazolin-6-ylethynyl]-piperidin-3-ol 3-[7-Methoxy-4-(3-methyl-4-phenoxy-phenylamino)-quinazolin-6-ylethynyl]-piperidin-3-ol 3-[7-Methoxy-4-(3-chloro-4-phenoxy-phenylamino) quinazolin-6-ylethynyl]-piperidin-3-ol 3-[7-Methoxy-4-(3-methoxy-4-phenoxy-phenylamino)-quinazolin-6-ylethynyl]-piperidin-3-ol (6-Azetidine-3-ylethynyl-quinazolin-4-yl)-3-methoxy-4-phenoxy-phenyl)-amine (3-Methyl-4-phenoxy-phenyl)-(6-morpholin-2-ylethynyl-quinazolin-4-yl)-amine (3-Methoxy-4-phenoxy-phenyl)-(6-morpholin-2-ylethynyl-quinazolin-4-yl)-amine (3-Chloro4-phenoxy-phenyl)-(6-morpholin-2-ylethynyl-quinazolin-4-yl)-amine (3-Methyl-4-phenoxy-phenyl)-[6-(1,4,5,6-tetrahydro-pyridin-3-ylethynyl)-quinazolin-4-yl]-amine (3-Methoxy-4-phenoxy-phenyl)-[6-(1,4,5,6-tetrahydro-pyridin-3-ylethynyl)-quinazolin-4-yl]-amine (3-Chloro-4-phenoxy-phenyl)-[6-(1,4,5,6-tetrahydro-pyridin-3-ylethynyl)-quinazolin-4-yl]-amine (3-Methyl-4-phenoxy-phenyl)-[6-(1,2,5,6-tetrahydro-pyridin-3-ylethynyl)-quinazolin-4-yl]-amine (3-Methoxy-4-phenoxy-phenyl)-[6-(1,2,5,6-tetrahydro-pyridin-3-ylethynyl)-quinazolin-4-yl]-amine (3-Chloro-4-phenoxy-phenyl)-[6-(1,2,5,6-tetrahydro-pyridin-3-ylethynyl)-quinazolin-4-yl]-amine (3-Methyl-4-phenoxy-phenyl)-[6-(1,2,3,6-tetrahydro-pyridin-4-ylethynyl)-quinazolin-4-yl]-amine (3-Methoxy-4-phenoxy-phenyl)-[6-(1,2,3,6-tetrahydro-pyridin-4-ylethynyl)-quinazolin-4-yl]-amine (3-Chloro-4-phenoxy-phenyl)-[6-(1,2,3,6-tetrahydro-pyridin-4-ylethynyl)-quinazolin-4-yl]-amine

[6-(3-Amino-3-methyl-but-1-ynyl)-quinazolin-4-yl]-(3-methyl-4-phenoxy-phenyl)-amine

[6-(3-Amino-3-methyl-but-1-ynyl)-quinazolin-4-yl]-(3-methoxy-4-phenoxy-phenyl)-amine

[6-(3-Amino-3-methyl-but-1-ynyl)-quinazolin-4-yl]-(3chloro4-phenoxy-phenyl)-amine

[6-(3-Amino-but-1-ynyl)-quinazolin-4-yl]-(3-methyl-4-phenoxy-phenyl)-amine

[6-(3-Amino-but-1-ynyl)-quinazolin-4-yl]-(3-methyl-4-phenoxy-phenyl)-amine

[6-(3-Amino-but-1-ynyl)-quinazolin-4-yl]-(3-methyl-4-phenoxy-phenyl)-amine

What is claimed is:

1. A compound of the formula 1

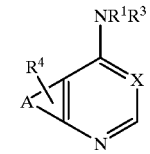

or a pharmaceutically acceptable salt or solvate thereof, wherein:

X is N;

A represents a fused 6-membered carbon ring, the fused ring containing a total of 3 double bonds inclusive of the bond in the pyrimidine ring to which it is fused and wherein said A moiety is optionally substituted with 1 to 3 $R^5$ groups;

each $R^1$ and $R^2$ is independently H or $C_1$–$C_6$ alkyl;

$R^3$ is —$(CR^1R^2)_m$—$R^8$ wherein m is 0 or 1;

or $R^1$ and $R^3$ are taken together to form a group of the formula

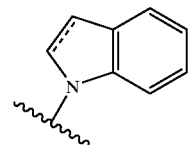

wherein said group is optionally substituted with 1 to 3 R5 groups;

$R^4$ is —$(CR^1R^2)_m$—C≡C—$(CR^1R^2)_t R^9$, —$(CR^1R^2)_m$—C═C—$(CR^1R^2)_t$—$R^9$, —C═$NOR^{12}$, or —$X^1$—$R^{12}$ wherein m is an integer from 0 to 3, t is an integer from 0 to 5, and $X^1$ is a divalent group derived from azetidine, oxetane or a $C_3$–$C_4$ carbocyclic group;

or $R^4$ is —$(CR^1R^2)_m$—C≡C—$(CR^1R^2)_k R^{13}$ or —$(CR^1R^2)_m$—C═C—$(CR^1R^2)_k R^{13}$ wherein k is an integer from 1 to 3 and m is an integer from 0 to 3;

or $R^4$ is —$(CR^1R^2)_t R^9$, wherein t is an integer from 0 to 5 and the attachment point to $R^9$ is through a carbon atom of the $R^9$ group;

each $R^5$ is independently selected from halo, hydroxy, —$NR^1R^2$, $C_1$–$C_6$ alkyl, trifluoromethyl, $C_1$–$C_6$ alkoxy, trifluoromethoxy, —$C(O)R^6$, —$CO_2R^6$, —$NR^6C(O)R^1$, —$C(O)NR^6R^7$, —$SO_2NR^6R^7$, —$NR^6C(O)NR^7R^1$, and —$NR^6C(O)OR^7$;

each $R^6$ and $R^7$ is independently selected from H, $C_1$–$C_6$ alkyl, —$(CR^1R^2)_t(C_6$–$C_{10}$ aryl), and —$(CR^1R^2)_t$(4–10 membered heterocyclic), wherein t is an integer from 0 to 5, 1 or 2 ring carbon atoms of the heterocyclic group are optionally substituted with an oxo (═O) moiety, and the alkyl, aryl and heterocyclic moieties of the foregoing $R^6$ and $R^7$ groups are optionally substituted with 1 to 3 substituents independently selected from halo, cyano, nitro, —$NR^1R^2$, trifluoromethyl, trifluoromethoxy, $C_1$–$C_6$ alkyl, $C_2$–$C_6$ alkenyl, $C_2$–$C_6$ alkynyl, hydroxy, and $C_1$–$C_6$ alkoxy;

$R^8$ is independently selected from —$(CR^1R^2)_t(C_6$–$C_{10}$ aryl) and —$(CR^1R^2)_t$(4–10 membered heterocyclic), wherein t is an integer from 0 to 5, 1 or 2 ring carbon atoms of the heterocyclic group are optionally substituted with an oxo (═O) moiety, and each of the foregoing $R^8$ groups is optionally substituted with 1 to 5 $R^{10}$ groups;

$R^9$ is a non-aromatic mono-cyclic ring, a fused or bridged bicyclic ring, or a spirocyclic ring, wherein said ring contains from 3 to 12 carbon atoms in which from 0 to 3 carbon atoms are optionally replaced with a hetero moiety independently selected from N, O, $S(O)_j$ wherein j is an integer from 0 to 2, and —$NR^{12}$, provided that two O atoms, two $S(O)_j$ moieties, an O atom and a $S(O)_j$ moiety, an N atom and an S atom, or an N atom and an O atom are not attached directly to each other within said ring, and wherein the carbon atoms of said ring are optionally substituted with 1 to 2 $R^{11}$ groups;

each $R^{10}$ is independently selected from halo, cyano, nitro, trifluoromethoxy, trifluoromethyl, azido, hydroxy, $C_1$–$C_6$ alkoxy, $C_1$–$C_{10}$ alkyl, $C_2$–$C_6$ alkenyl, $C_2$–$C_6$ alkynyl, —$C(O)R^6$, —$C(O)OR^6$, —$OC(O)R^6$, —$NR^6C(O)R^7$, —$NR^6C(O)NR^1R^7$, —$NR^6C(O)OR^7$, —$C(O)NR^6R^7$, —$NR^6R^7$, —$NR^6OR^7$, —$SO_2NR^6R^7$, —$S(O)_j(C_1$–$C_6$ alkyl) wherein j is an integer from 0 to 2, —$(CR^1R^2)_t(C_6$–$C_{10}$ aryl), —$(CR^1R^2)_t$(4–10 membered heterocyclic), —$(CR^1R^2)_q C(O)(CR^1R^2)_t(C_6$–$C_{10}$ aryl), —$(CR^1R^2)_q C(O)(CR^1R^2)_t$(4–10 membered heterocyclic), —$(CR^1R^2)_t O(CR^1R^2)_q(C_6$–$C_{10}$ aryl), —$(CR^1R^2)_t O(CR^1R^2)_q$(4–10 membered heterocyclic), —$(CR^1R^2)_q S(O)_j(CR^1R^2)_t(C_6$–$C_{10}$ aryl), and —$(CR^1R^2)_q S(O)_j(CR^1R^2)_t$(4–10 membered heterocyclic), wherein j is 0, 1 or 2, q and t are each independently an integer from 0 to 5, 1 or 2 ring carbon atoms of the heterocyclic moieties of the foregoing $R^{10}$ groups are optionally substituted with an oxo (═O) moiety, and the alkyl, alkenyl, alkynyl, aryl and heterocyclic moieties of the foregoing $R^{10}$ groups are optionally substituted with 1 to 3 substituents independently selected from halo, cyano, nitro, trifluoromethyl, trifluoromethoxy, azido, —$OR^6$, —$C(O)R^6$, —$C(O)OR^6$, —$OC(O)R^6$, —$NR^6C(O)R^7$, —$C(O)NR^6R^7$, —$NR^6R^7$, —$NR^6OR^7$, $C_1$–$C_6$ alkyl, $C_2$–$C_6$ alkenyl, $C_2$–$C_6$ alkynyl, —$(CR^1R^2)_t(C_6$–$C_{10}$ aryl), and —$(CR^1R^2)_t$(4–10 membered heterocyclic), wherein t is an integer from 0 to 5;

each $R^{11}$ is independently selected from —$R^{12}$, —$OR^1$, —$NR^1R^2$, —$NR^6C(O)R^7$, —$NR^6C(O)NR^7R^1$, —$NR^6C(O)OR^7$, and —$NR^6SO_2NR^7R^1$, or $R^{11}$ replaces two hydrogen atoms on a carbon to form an oxo (C═O) group;

$R^{12}$ is $R^6$, —$C(O)R^6$ or —$SO_2R^6$, —$C(O)NR^6R^7$, —$SO_2NR^6R^7$, or —$CO_2R^6$;

$R^{13}$ is —$NR^1R^{12}$ or —$OR^{12}$;

and wherein any of the above-mentioned substituents comprising a $CH_3$ (methyl), $CH_2$ (methylene), or CH (methine) group which is not attached to a halogeno, SO or $SO_2$ group or to a N, O or S atom optionally bears on said group a substituent selected from hydroxy, halo, $C_1$–$C_4$ alkyl, $C_1$–$C_4$ alkoxy and —$NR^1R^2$.

2. A compound according to claim 1 wherein $R^4$ is —$(CR^1R^2)_m$—C≡C—$(CR^1R^2)_t R^9$ wherein m is an integer from 0 to 3 and t is an integer from 0 to 5.

3. A compound according to claim 1 wherein $R^4$ is —$(CR^1R^2)_m$—C═C—$(CR^1R^2)_t$—$R^9$ wherein m is an integer from 0 to 3 and t is an integer from 0 to 5.

4. A compound according to claim 1 wherein $R^4$ is —$(CR^1R^2)_m$—C≡C—$(CR^1R^2)_k R^{13}$ or —$(CR^1R^2)_m$—C═C—$(CR^1R^2)_k R^{13}$ wherein m is an integer from 0–3 and k is an integer from 1 to 3.

5. A compound according to claim 1 wherein $R^4$ is —C═$NOR^{12}$, or —$X^1$—$R^{12}$ wherein $X^1$ is a divalent group derived from azetidine, oxetane or a $C_3$–$C_4$ carbocyclic group; or $R^4$ is —$(CR^1R^2)_t R^9$, wherein the attachment point to $R^9$ is through a carbon atom of $R^9$.

6. A compound according to claim 2 wherein $R^8$ is selected from —$(CR^1R^2)_t$(phenyl), —$(CR^1R^2)_t$(pyridyl), —$(CR^1R^2)_t$(pyrimidinyl), —$(CR^1R^2)_t$(indolyl), —$(CR^1R^2)_t$(indazolyl) and —$(CR^1R^2)_t$(benzimidazolyl), wherein t is an integer from 0 to 5, and each of the foregoing $R^8$ groups is optionally substituted with 1 to 5 $R^{10}$ groups.

7. A compound according to claim 3 wherein $R^8$ is selected from —$(CR^1R^2)_t$(phenyl), —$(CR^1R^2)_t$(pyridyl), —$(CR^1R^2)_t$(pyrimidinyl), —$(CR^1R^2)_t$(indolyl), —$(CR^1R^2)_t$(indazolyl) and —$(CR^1R^2)_t$(benzimidazolyl), wherein t is an integer from 0 to 5, and each of the foregoing $R^8$ groups is optionally substituted with 1 to 5 $R^{10}$ groups.

8. A compound according to claim 4 wherein $R^8$ is selected from —$(CR^1R^2)_t$(phenyl), —$(CR^1R^2)_t$(pyridyl), —$(CR^1R^2)_t$(pyrimidinyl), —$(CR^1R^2)_t$(indolyl), —$(CR^1R^2)_t$(indazolyl) and —$(CR^1R^2)_t$(benzimidazolyl), wherein t is an integer from 0 to 5, and each of the foregoing $R^8$ groups is optionally substituted with 1 to 5 $R^{10}$ groups.

9. A compound according to claim 3 wherein $R^8$ is selected from —$(CR^1R^2)_t$(phenyl), —$(CR^1R^2)_t$(pyridyl), —$(CR^1R^2)_t$(pyrimidinyl), —$(CR^1R^2)_t$(indolyl), —$(CR^1R^2)_t$(indazolyl) and —$(CR^1R^2)_t$(benzimidazolyl), wherein t is an integer from 0 to 5, and each of the foregoing $R^8$ groups is optionally substituted with 1 to 5 $R^{10}$ groups.

10. A compound according to claim 6 wherein the m variable in the $R^4$ group is 0, t in the $R^8$ group is an integer between 0 and 2, and $R^9$ is a 4 to 10 membered heterocyclic group having 1 to 3 hetero moieties as indicated in claim 1 wherein said $R^9$ is optionally substituted with 1 to 2 $R^{11}$ groups.

11. A compound according to claim 8 wherein $R^4$ is —$(CR^1R^2)_m$—C≡C—$(CR^1R^2)_k R^{13}$ wherein m is 0 and k is an integer from 1 or 2.

12. A compound according to claim 9 wherein $R^4$ is —$(CR^1R^2)_t R^9$, wherein the attachment point to $R^9$ is through a carbon atom of $R^9$; t is an integer from 0 to 2, and $R^9$ is a 4–10 membered heterocyclic group having 1 to 3 hetero moieties as indicated in claim 1 wherein said $R^9$ is optionally substituted with 1 to 2 $R^{11}$ groups.

13. A compound according to claim 1 selected from the group consisting of:

Acetic acid 3-[4-(1-benzenesulfonyl-1H-indol-5-ylamino)-quinazolin-6-yl]-allyl ester;
(1-Benzenesulfonyl-1H-indol-5-yl)-{6-[3-(4-methyl-piperazin-1-yl)-prop-1-ynyl]-quinazolin-4-yl}amine;
(1-Benzenesulfonyl-1H-indol-5-yl)-[6-(3-pyrrolidin-1-yl-prop-1-ynyl)-quinazolin-4-yl]-amine;
4-[4-(1-Benzenesulfonyl-1H-indol-5-ylamino)-quinazolin-6-ylethynyl]-piperidin-4-ol;
(1-Benzenesulfonyl-1H-indol-5-yl)-(6-piperidin-4-ylethynyl-quinazolin-4-yl)-amine;
[6-(4-Amino-tetrahydro-pyran-4-ylethynyl)-quinazolin-4-yl]-(1-benzenesulfonyl-1H-indol-5-yl)-amine;
1-Methyl-4-{4-[3-methyl-4-(pyridin-2-ylmethoxy)-phenylamino]-quinazolin-6-ylethynyl}-piperidin-4-ol;
1-[4-(1-Benzenesulfonyl-1H-indol-5-ylamino)-quinazolin-6-yl]-4-methyl-pent-1-yn-3-ol;
4-{4-[4-(1-Phenyl-ethoxy)-phenylamino]-quinazolin-6-ylethynyl}-tetrahydro-pyran-4-ol;
1-[4-(1-Benzenesulfonyl-1H-indol-5-ylamino)-quinazolin-6-yl -4,4-dimethyl-pent-yn-3-ol;
4,4-Dimethyl-1-{4-[4-(1-phenyl-ethoxy)-phenylamino]-quinazolin-6-yl}-pent-1-yn-3-ol;
3-{4-[1-(Propane-2-sulfonyl)-1H-indol-5-ylamino]-quinazolin-6-ylethynyl)-piperidin-3-ol;
1-Methyl-3-[4(4-phenoxy-phenylamino)-quinazolin-6-ylethynyl]-piperidin-3-ol;
3-[4-(3-Methyl-4-phenoxy-phenylamino)-quinazolin-6-ylethynyl]- piperidin-3-ol,
3-[4-(3-Chloro4-phenoxy-phenylamino)-quinazolin-6-yl]-1-pyrrolidin-2-yl-prop-2-yn-1-ol;
5-[4-(1-Benzyl-1H-indazol-5-ylamino)-quinazolin-6-ylethynyl]-4,4-dimethyl-oxazolidin-2-one;
4-Amino-1-[4-(3-chloro-4-phenoxy-phenylamino)-quinazolin-6-yl]- pent-1-yn-3-ol;
4-Amino-1-[4-(3-chloro-4-phenoxy-phenylamino)-quinazolin-6-yl]-4-methyl-pent-1-yn-3-ol;
3-{2-[4-(3-Methyl-4-phenoxy-phenylamino)-quinazolin-6-yl]-ethyl}-piperidin-3-ol;

and the pharmaceutically acceptable salts and solvates of the foregoing compounds.

14. A compound according to claim 1 selected from the group consisting of:

(+)-(3-Methyl-4-phenoxy-phenyl)-(6-piperidin-3(R)-ylethynyl-quinazolin-4-yl)-amine;
(−)-(3-Methyl-4-phenoxy-phenyl)-(6-piperidin-3(S)-ylethynyl-quinazolin-4-yl)-amine;
3-(S)-[4-(3-Methyl-4-phenoxy-phenylamino)-quinazolin-6-ylethynyl]-piperidine-1-carboxylic acid methylamide;
3-(S)-[4-(3-Methoxy-4-phenoxy-phenylamino)-quinazolin-6-ylethynyl]-piperidine-1-carboxylic acid methylamide;
(3-Methyl-4-phenoxy-phenyl)-(6-pyrrolidin-3-ylethynyl-quinazolin-4-yl)-amine;
3-[4-(5-Methyl-6-phenoxy-pyridin-3-ylamino)-quinazolin-6-ylethynyl]-piperidin-3-ol;
(−)-3-[4-(3-Methyl-4-phenoxy-phenylamino)-quinazolin-6-ylethynyl]-piperidin-3-ol;
(+)-3-[4-(3-Methyl-4-phenoxy-phenylamino)-quinazolin-6-ylethynyl]-piperidin-3-ol;
4-[4-(3-Methyl-4-phenoxy-phenylamino)-quinazolin-6-ylethynyl]-tetrahydro-pyran4-ol;
{6-[1-(2-Methoxy-ethyl)-piperidin-3-ylethynyl]-quinazolin-4-yl}-(3-methyl-4-phenoxy-phenyl)-amine;
[4-(2-Fluoro-phenoxy)-3-methyl-phenyl]-(6-piperidin-3-ylethynyl-quinazolin-4-yl)-amine,
[4-(3-Fluoro-phenoxy)-3-methyl-phenyl]-(6-piperidin-3-ylethynyl-quinazolin-4-yl)-amine;
(6-Azetidine-3-ylethynyl-quinazolin-4-yl)-(3-methyl-4-phenoxy-phenyl)-amine;
3-{4-[4-(2-Fluoro-phenoxy)-3-methyl-phenylamino]-quinazolin-6-ylethynyl}-piperidin-3-ol;
3-{4-[4-(3-Fluoro-phenoxy)-3-methyl-phenylamino]-quinazolin-6-ylethynyl}-piperidin-3-ol;
4-[4-(3-Methyl-4-phenoxy-phenylamino)-quinazolin-6-ylethynyl]-piperidin-4-ol;
(3-Chloro-4-phenoxy-phenyl)-(6-piperidin-3-ylethynyl-quinazolin-4-yl)-amine;
3-[4-(3-Methyl-4-phenoxy-phenylamino)-quinazolin-6-ylethynyl]-8-aza-bicyclo[3.2.1]octan-3-ol;
(3-Chloro-4-phenoxy-phenyl)-(6-piperidin-4-ylethynyl-quinazolin-4-yl)-amine;
3-[4-(3-Methyl-4-phenoxy-phenylamino)-quinazolin-6-ylethynyl]-pyrrolidin-3-ol;
3-[4-(3-Methyl-4-phenoxy-phenylamino)-quinazolin-7-ylethynyl]-piperidin-3ol;

and the pharmaceutically acceptable salts and solvates of the foregoing compounds.

15. A compound according to claim 1 selected from the group consisting of:

N-{3-[4-(3-Chloro-4-phenoxy-phenylamino)-quinazolin-6-yl]-prop-2-ynyl}-acetamide;
N-{3-[4-(3-Methyl-4-phenoxy-phenylamino)-quinazolin-6-yl]-prop-2-ynyl}-acetamide:
(3-{3-[4-(3-Methyl-4-phenoxy-phenylamino)-quinazolin-6-yl]-prop-2-ynyl}-3-aza-bicyclo[3.1.0]hex-6-yl)-methanol;
4-{3-[4-(3-Methoxy-4-phenoxy-phenylamino)-quinazolin-6-yl]-prop-2-ynyl}-piperazine-1-carboxylic acid methylamide;
{6-[3-(1,1-Dioxo-1-thiomorpholin-4-yl)-prop-1-ynyl]-quinazolin-4-yl}-(3-methyl-4-phenoxy-phenyl)-amine;
1-{3-[4-(3-Methyl-4-phenoxy-phenylamino)-quinazolin-6-yl]-prop-2-ynyl}-piperidin-4-ol;
N-{1-Methyl-3-[4-(3-methyl-4-phenoxy-phenylamino)-quinazolin-6-yl]-prop-2-ynyl}-acetamide;
N-{3-[4-(3-Chloro-4-phenoxy-phenylamino)-quinazolin-6-yl]-1-methyl-prop-2-ynyl}-acetamide;
N-{1,1-Dimethyl-3-[4-(3-methyl-4-phenoxy-phenylamino)-quinazolin-6-yl]-prop-2-ynyl}-acetamide;
4-[4-(1-Benzenesulfonyl-1H-indol-5-ylamino)-quinazolin-6-ylethynyl]-1-methyl-piperidin-4-ol;
3-[4-(1-Benzenesulfonyl-1H-indol-5-ylamino)-quinazolin-6-ylethynyl]-piperidin-3-ol;

3-[4-(3-Bromo-4-phenoxy-phenylamino)-quinazolin-6-ylethynyl]-piperidin-3-ol;

3-[4-(4-Benzenesulfonyl-3-methyl-phenylamino)-quinazolin-6-ylethynyl]-piperidin-3-ol;

3-[4-(4-Cyclohexyloxy-3-methyl-phenylamino)-quinazolin-6-ylethynyl]-piperidin-3-ol;

2-Methyl-4-[4-(3-methyl-4-phenoxy-phenylamino)-quinazolin-6-yl]-but-3-yn-2-ol;

2-Amino-4-[4-(3-methyl-4-phenoxy-phenylamino)-quinazolin-6-yl]-but-3-yn-1-ol;

3-[4-3-Methyl-4-phenylsulfanyl-phenylamino)-quinazolin-6-ylethynyl]-piperidin-3-ol;

and the pharmaceutically acceptable salts and solvates of the foregoing compounds.

16. A compound according to claim 1 selected from the group consisting of:

3-[4-(3-Chloro-4-fluoro-phenylamino)-quinazolin-6-ylethynyl]-piperidin-3-ol;

3-[4-(3-Ethynyl-phenylamino)-quinazolin-6-ylethynyl]-piperidin-3-ol;

(3-Methyl-4-phenoxy-phenyl)-[6-(1-methyl-piperidin-3-ylethynyl)-quinazolin-4-yl]-amine;

(3-Methyl-4-phenoxy-phenyl)-[6-(2-piperidin-3-yl-ethyl)-quinazolin-4-yl]-amine;

3-{2-[4-(3-Methyl-4-phenoxy-phenylamino)-quinazolin-6-yl]-ethyl}-piperidin-3-ol;

3-[4-(4-Phenoxy-phenylamino)-quinazolin-6-ylethynyl]-piperidin-3-ol;

and the pharmaceutically acceptable salts and solvates of the foregoing compounds.

17. A method for the treatment of abnormal cell growth in a mammal comprising administering to said mammal an amount of a compound of claim 1 that is effective in treating abnormal cell growth.

18. A method according to claim 17 wherein said abnormal cell growth is cancer.

19. A method according to claim 18 wherein said cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes. carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

20. A pharmaceutical composition for the treatment of abnormal cell growth in a mammal comprising an amount of a compound of claim 1 that is effective in treating abnormal cell growth, and a pharmaceutically acceptable carrier.

21. A method of preparing a compound of claim 1 which comprises reacting a compound of the formula 11 with a compound of the formula 3

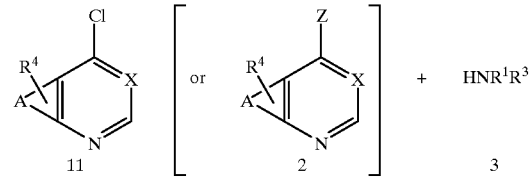

wherein A, X, $R^1$, $R^3$ and $R^4$ are as defined above.

* * * * *